United States Patent [19]
Baker et al.

[11] Patent Number: 6,100,293
[45] Date of Patent: Aug. 8, 2000

[54] TETRACYCLIC TRITERPENE DERIVATIVES WITH IMMUNOSUPPRESSANT ACTIVITY

[75] Inventors: Robert K. Baker, Cranford; Jianming Bao, Scotch Plains; Frank Kayser, Hoboken; Shouwu Miao, Edison; William H. Parsons, Belle Mead; Kathleen M. Rupprecht, Cranford, all of N.J.

[73] Assignee: Merck & Co., Inc., Rahway, N.J.

[21] Appl. No.: 09/164,906

[22] Filed: Oct. 1, 1998

Related U.S. Application Data

[60] Provisional application No. 60/061,933, Oct. 17, 1997.

[51] Int. Cl.$^7$ ........................ A61K 31/365; C07D 313/06
[52] U.S. Cl. .......................... 514/450; 549/268; 549/354; 549/60; 546/281.7; 514/337; 514/444
[58] Field of Search .................................. 514/337, 444, 514/450; 546/281.7; 549/60, 268, 354

[56] References Cited

U.S. PATENT DOCUMENTS

| | | | |
|---|---|---|---|
| 3,483,191 | 12/1969 | Krakower et al. | 260/239.57 |
| 4,453,967 | 6/1984 | Mori | 71/88 |
| 5,010,104 | 4/1991 | Oshima et al. | 514/510 |
| 5,599,950 | 2/1997 | Teng | 549/297 |
| 5,631,282 | 5/1997 | Goetz | 514/450 |
| 5,679,705 | 10/1997 | Baker et al. | 514/450 |
| 5,696,156 | 12/1997 | Baker et al. | 514/450 |

FOREIGN PATENT DOCUMENTS

| | | |
|---|---|---|
| WO 96/40688 | 12/1996 | WIPO . |
| WO 97/16068 | 5/1997 | WIPO . |
| WO 97/16182 | 5/1997 | WIPO . |
| WO 97/16437 | 5/1997 | WIPO . |
| WO 97/16438 | 5/1997 | WIPO . |
| WO 98/16532 | 4/1998 | WIPO . |

OTHER PUBLICATIONS

Abreu, et al., "A Nor–Triterpenoid From Lophanthera Lactescens", Phytochemistry, vol. 29(7), pp. 2257–2261, 1990.
Sabata, et al., "Tetranortriterpenoids and Related Substances. Part 19.1 Revised Structures od Atalantolide and Atalantin, Limonoids from the Root Bark of Atalantia Monophylla Correa (Rutaceae)", J. Chem. Soc. Perkin I, pp. 1876–1877, 1977.

*Primary Examiner*—Charanjit S. Aulakh
*Attorney, Agent, or Firm*—J. Antonio Garcia-Rivas; Mark R. Daniel

[57] ABSTRACT

The compounds of Formula I

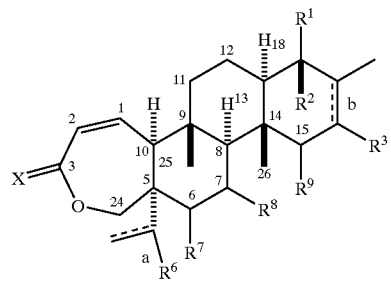

are useful as immunosuppressive agents.

14 Claims, No Drawings

TETRACYCLIC TRITERPENE DERIVATIVES WITH IMMUNOSUPPRESSANT ACTIVITY

RELATED APPLICATIONS

This application claims benefit of U.S. Provisional application Ser. No. 60/061,933, filed on Oct. 17, 1997.

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma.

Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A (CsA), which was approved by the US FDA in 1983 is currently the leading drug used to prevent rejection of transplanted organs. In 1993, FK-506 (Prograf) was approved by the US FDA for the prevention of rejection in liver transplantation. CsA and FK-506 act by inhibiting the body's immune system from mobilizing its vast arsenal of natural protecting agents to reject the transplant's foreign protein. In 1994, CsA was approved by the US FDA for the treatment of severe psoriasis and has been approved by European regulatory agencies for the treatment of atopic dermatitis. Though they are effective in fighting transplant rejection, CsA and FK-506 are known to cause several undesirable side effects including nephrotoxicity, neurotoxicity, and gastrointestinal discomfort.

Newer, safer drugs exhibiting less side effects are constantly being searched for in the field.

Four active components of *Spachea correa* were recently identified which inhibit thymidine uptake of T cells.

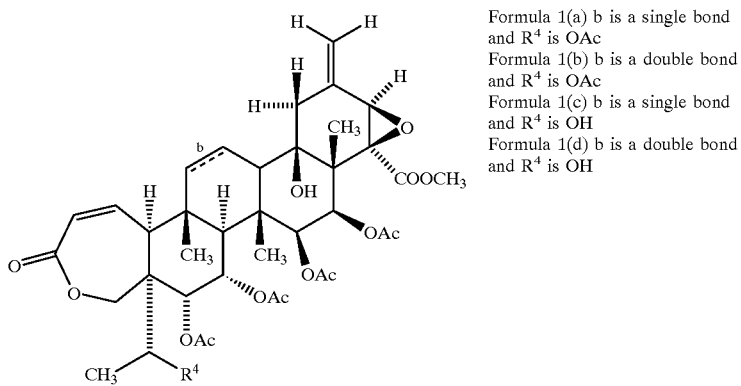

Formula 1(a) b is a single bond and $R^4$ is OAc
Formula 1(b) b is a double bond and $R^4$ is OAc
Formula 1(c) b is a single bond and $R^4$ is OH
Formula 1(d) b is a double bond and $R^4$ is OH These compounds are useful as immunosuppressive agents in animals, including man. The present invention describes newly developed immunosuppressive compounds derived from the compounds described in Formulae 1(a) through 1(d) and which have the relative stereochemistry depicted above.

SUMMARY OF THE INVENTION

This invention relates to a class of triterpene derivatives of the general structural Formula I

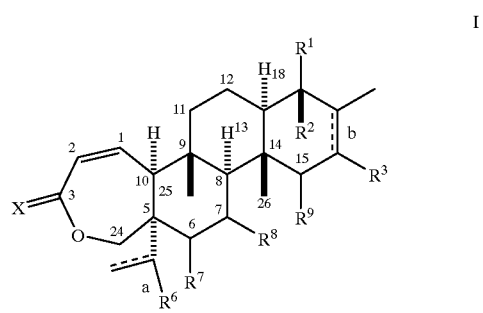

are useful as immunosuppressives.

As an immunosuppressive, the compounds of this invention are useful in the treatment of autoimmune diseases, the prevention of rejection of foreign organ transplants and/or related afflictions, diseases and illnesses. Also within the scope of this invention are pharmaceutical formulations comprising a compound of Formula I and a pharmaceutical carrier, as well as, pharmaceutical formulations comprising a compound of Formula I, and one or more immunosuppressive compounds and a pharmaceutical carrier.

DETAILED DESCRIPTION OF THE INVENTION

A. Scope of the Invention

The present invention is related to compounds of formula I, including but not limited to those specified in the examples, which are useful in a mammalian subject for the treatment and prevention of the resistance by transplantation of organs or tissue, graft-versus-host diseases brought about by medulla ossium transplantation; rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, bronchial asthma, allergic asthma, intrinsic asthma, extrinsic asthma and dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth; muscular dystrophy; Pyoderma and Sezary's syndrome, Addison's disease, ischemia-reperfusion injury of organs which occurs upon preservation, transplantation or ischemic disease, for example, thrombosis and cardiac infraction, endotoxinshock, pseudo-membranous colitis, colitis caused by drug or radiation, ischemic acute renal insufficiency, chronic renal insufficiency, toxinosis caused by lung-oxygen or drug, for example, paracort and bleomycins, lung cancer, pulmonary emphysema, cataracta, siderosis, retinitis, pigmentosa, senile macular degeneration, vitreal scarring, corneal alkali burn; dermatitis erythema multiforme, linear IgA ballous dermatitis and cement dermatitis, gingivitis, periodontitis, sepsis, pancreatitis, diseases caused by environmental pollution, aging, carcinogenis, metastasis of carcinoma and hypobaropathy; disease caused by histamine or leukotriene-$C_4$ release; Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmention of chemotherapeutic effect, preventing or treating activity of cytomegalovirus infection, HCMV infection, and antiinflammatory activity; and treatment of immunodepression or a disorder involving immunodepression, including AIDS, cancer, senile dementia, trauma, chronic bacterial infection, and certain central nervous system disorders.

More particularly, this invention relates to compounds of the general structural Formula I:

or a pharmaceutically acceptable salt, crystal form, or hydrate, wherein:

X is: O, S, NH, or H and $R^{10}$;

a and b are independently a single bond or a double bond, and represented by ═══ in the structure above;

n is: 0,1 or 2;

r is: 0 or 1;

s is: 0 or 1;

$R^1$ is:

(1) H, (2) =O, when $R^2$ is absent, (3) $(C_1–C_{10})$-alkyl, wherein alkyl is unsubstituted or substituted with one or two of the substituents selected from the group consisting of:
   (a) halo, wherein halo is fluoro, chloro, bromo, or iodo,
   (b) hydroxy,
   (c) oxo,
   (d) $(C_1–C_6)$-alkyloxy,
   (e) $(C_1–C_6)$-S(O)$_n$-,
   (f) aryl-$(C_1–C_6)$-alkyloxy,
   (g) cyano,
   (h) nitro,
   (i) vinyl,
   (j) $NR^4R^5$,
   (k) $NR^4COC_1–C_6$-alkyl,
   (l) CHO,
   (m) $CO_2H$,
   (n) $COC_1–C_6$-alkyl,
   (o) $CO_2C_1–C_6$-alkyl,
   (p) $CONR^4R^5$,
   (q) aryl, wherein aryl is defined as phenyl or naphthyl, unsubstituted or substituted with one, two or three of the substituents selected from the group consisting of:

(a') halo, as defined above,
(b') hydroxy,
(c') $(C_1-C_6)$-alkyl,
(d') $(C_1-C_4)$-perfluoroalkyl,
(e') $(C_1-C_6)$-alkenyl,
(f') $(C_1-C_6)$-alkynyl,
(g') $(C_1-C_6)$-alkyloxy,
(h') $(C_1-C_6)$-alkyl-S(O)$_n$-,
(i') phenyl,
(j') phenoxy,
(k') cyano,
(l') nitro,
(m') $CO_2H$,
(n') $COC_1-C_6$-alkyl,
(o') $CO_2C_1-C_6$-alkyl,
(p') $CONR^4R^5$,
(q') $NR^4R^5$,
(r') $NR^4COC_1-C_6$-alkyl,
(s') $(C_1-C_6)$-alkenyloxy, and
(t') benzyloxy;
(r) heteroaryl, wherein heteroaryl is defined as an unsubstituted, monosubstituted, or disubstituted five or six membered aromatic heterocycle containing from 1 to 3 heteroatoms selected from the group consisting of O, N and S and wherein the substituents are selected from the group consisting of:
(a') halo, as defined above,
(b') hydroxy,
(c') $(C_1-C_6)$-alkyl,
(d') $(C_1-C_4)$-perfluoroalkyl,
(e') $(C_1-C_6)$-alkenyl,
(f') $(C_1-C_6)$-alkynyl,
(g') $(C_1-C_6)$-alkyloxy,
(h') $(C_1-C_6)$-alkyl-S(O)$_n$-,
(i') phenyl,
(j') phenoxy,
(k') cyano,
(l') nitro,
(m') $CO_2H$,
(n') $COC_1-C_6$-alkyl,
(o') $CO_2C_1-C_6$-alkyl,
(p') $CONR^4R^5$,
(q') $NR^4R^5$,
(r') $NR^4COC_1-C_6$-alkyl,
(s') fused benzo, and
(t') fused pyridyl group,
(s) heterocyclyl, wherein heterocyclyl is defined as a cyclic, non-aromatic substituent containing from 1 to 3 heteroatoms selected from the group consisting of O, N, and S, said heterocycle being unsubstituted or substituted with one, two or three substituents selected from the group consisting of:
(a') halo, as defined above,
(b') hydroxy,
(c') $(C_1-C_6)$-alkyl,
(d') $(C_1-C_4)$-perfluoroalkyl,
(e') $(C_1-C_6)$-alkenyl,
(f') $(C_1-C_6)$-alkynyl,
(g') $(C_1-C_6)$-alkyloxy,
(h') $(C_1-C_6)$-alkyl-S(O)$_n$-,
(i') phenyl,
(j') phenoxy,
(k') cyano,
(l') nitro,
(m') $CO_2H$,
(n') $COC_1-C_6$-alkyl,
(o') $CO_2C_1-C_6$-alkyl,
(p') $CONR^4R^5$,
(q') $NR^4R^5$,
(r') NR4COC1–C6-alkyl,
(s') oxo,
(t') fused benzo, and
(u') fused pyridyl group;
(4) $(C_2-C_{10})$-alkenyl, wherein alkenyl is unsubstituted or substituted with one or two of the substituents selected from the group consisting of:
(a) halo, wherein halo is fluoro, chloro, bromo, or iodo,
(b) hydroxy,
(c) oxo,
(d) $(C_1-C_6)$-alkyloxy,
(e) $(C_1-C_6)$-S(O)$_n$-,
(f) phenyl-$(C_1-C_6)$-alkyloxy,
(g) cyano,
(h) nitro,
(i) vinyl,
(j) $NR^4R^5$,
(k) $NR^4COC_1-C_6$-alkyl,
(l) CHO,
(m) $CO_2H$,
(n) $COC_1-C_6$-alkyl,
(o) $CO_2C_1-C_6$-alkyl,
(p) $CONR^4R^5$,
(q) aryl, wherein aryl is as defined above,
(r) heteroaryl, wherein heteroaryl is as defined above, and
(s) heterocycle, wherein the heterocycle is as defined above,
(5) $(C_2-C_{10})$-alkynyl, wherein alkynyl is unsubstituted or substituted with one or two of the substituents selected from the group consisting of:
(a) halo, wherein halo is fluoro, chloro, bromo, or iodo,
(b) hydroxy,
(c) oxo,
(d) $(C_1-C_6)$-alkyloxy,
(e) $(C_1-C_6)$-S(O)$_n$-,
(f) phenyl-$(C_1-C_6)$-alkyloxy,
(g) cyano,
(h) nitro,
(i) vinyl,
(j) $NR^4R^5$,
(k) $NR^4COC_1-C_6$-alkyl,
(l) CHO,
(m) $CO_2H$,
(n) $COC_1-C_6$-alkyl,
(o) $CO_2C_1-C_6$-alkyl,
(p) $CONR^4R^5$,
(q) aryl, wherein aryl is as defined above,
(r) heteroaryl, wherein heteroaryl is as defined above,
(s) heterocycle, wherein heterocycle is as defined above, and
(t) $Si(R^4)_3$,
(6) an exo-methylene group, when $R^2$ is absent, or
(7) aryl, wherein aryl is defined as phenyl or naphthyl, unsubstituted or substituted with one, two or three of the substituents selected from the group consisting of:
(a') halo, as defined above,
(b') hydroxy,
(c') $(C_1-C_6)$-alkyl,
(d') $(C_1-C_4)$-perfluoroalkyl,
(e') $(C_1-C_6)$-alkenyl,
(f') $(C_1-C_6)$-alkynyl,
(g') $(C_1-C_6)$-alkyloxy,
(h') $(C_1-C_6)$-alkyl-S(O)$_n$-,
(i') phenyl, (j') phenoxy,
(k') cyano,
(l') nitro,
(m') $CO_2H$,
(n') $COC_1-C_6$-alkyl,
(o') $CO_2C_1-C_6$-alkyl,
(p') $CONR^4R^5$,
(q') $NR^4R^5$,
(r') $NR^4COC_1-C_6$-alkyl,
(s') $(C_1-C_6)$-alkenyloxy, and
(t') benzyloxy;

$R^2$ is:
(1) H,
   (2) absent when $R^1$ is oxo,
   (3) absent when $R^1$ is an exo-methylene group, or
   (4) OH, $R^3$ is:
(1) H, or
(2) $(C_1-C_{10})$-alkyl, wherein alkyl is unsubstituted or substituted with one or two of the substituents selected from the group consisting of:
   (a) halo, wherein halo is fluoro, chloro, bromo, iodo,
   (b) hydroxy,
   (c) oxo,
   (d) $(C_1-C_6)$-alkyloxy,
   (e) $(C_1-C_6)$-$S(O)_n$-,
   (f) aryl-$(C_1-C_6)$-alkyloxy,
   (g) cyano,
   (h) nitro,
   (i) vinyl,
   (j) $NR^4R^5$,
   (k) $NR^4COC_1-C_6$-alkyl,
   (l) CHO,
   (m) $CO_2H$,
   (n) $COC_1-C_6$-alkyl,
   (o) $CO_2C_1-C_6$-alkyl,
   (p) $CONR^4R^5$,
   (q) aryl, wherein aryl is defined as phenyl or naphthyl, unsubstituted or substituted with one, two or three of the substituents selected from the group consisting of:
      (a') halo, as defined above,
      (b') hydroxy,
      (c') $(C_1-C_6)$-alkyl,
      (d') $(C_1-C_4)$-perfluoroalkyl,
      (e') $(C_1-C_6)$-alkenyl,
      (f') $(C_1-C_6)$-alkynyl,
      (g') $(C_1-C_6)$-alkyloxy,
      (h') $(C_1-C_6)$-alkyl-$S(O)_n$-,
      (i') phenyl,
      (j') phenoxy,
      (k') cyano,
      (l') nitro,
      (m') $CO_2H$,
      (n') $COC_1-C_6$-alkyl,
      (o') $CO_2C_1-C_6$-alkyl,
      (p') $CONR^4R^5$,
      (g') $NR^4R^5$, and
      (r') $NR^4COC_1-C_6$-alkyl,
   (r) heteroaryl, wherein heteroaryl is defined as an unsubstituted, monosubstituted, or disubstituted five or six membered aromatic heterocycle containing from 1 to 3 heteroatoms selected from the group consisting of O, N and S and wherein the substituents are members selected from the group consisting of:
      (a') halo, as defined above,
      (b') hydroxy,
      (c') $(C_1-C_6)$-alkyl,
      (d') $(C_1-C_4)$-perfluoroalkyl,
      (e') $(C_1-C_6)$-alkenyl,
      (f') $(C_1-C_6)$-alkynyl,
      (g') $(C_1-C_6)$-alkyloxy,
      (h') $(C_1-C_6)$-alkyl-$S(O)_n$-,
      (i') phenyl,
      (j') phenoxy,
      (k') cyano,
      (l') nitro,
      (m') $CO_2H$,
      (n') $COC_1-C_6$-alkyl,
      (o') $CO_2C_1-C_6$-alkyl,
      (p') $CONR^4R^5$,
      (q') $NR^4R^5$,
      (r') $NR^4COC_1-C_6$-alkyl, and
      (s') fused benzo or pyridyl group,
   (s) heterocyclyl, wherein heterocyclyl is defined as a cyclic, non-aromatic substituent containing from 1 to 3 heteroatoms selected from the group consisting of O, N, and S, said heterocycle being unsubstituted or substituted with one, two or three substituents selected from the group consisting of:
      (a') halo, as defined above,
      (b') hydroxy,
      (c') $(C_1-C_6)$-alkyl,
      (d') $(C_1-C_4)$-perfluoroalkyl,
      (e') $(C_1-C_6)$-alkenyl,
      (f') $(C_1-C_6)$-alkynyl,
      (g') $(C_1-C_6)$-alkyloxy,
      (h') $(C_1-C_6)$-alkyl-$S(O)_n$-,
      (i') phenyl,
      (j') phenoxy,
      (k') cyano,
      (l') nitro,
      (m') $CO_2H$,
      (n') $COC_1-C_6$-alkyl,
      (o') $CO_2C_1-C_6$-alkyl,
      (p') $CONR^4R^5$,
      (q') $NR^4R^5$,
      (r') NR4COC1–C6-alkyl,
      (s') oxo,
      (t') fused benzo, and
      (u') fused pyridyl group;
   (t) $Si(R^4)_3$,
(3) $(C_2-C_{10})$-alkenyl, wherein alkenyl is unsubstituted or substituted with one or two of the substituents selected from the group consisting of:
   (a) halo, wherein halo is fluoro, chloro, bromo, or iodo,
   (b) hydroxy,
   (c) oxo,
   (d) $(C_1-C_6)$-alkyloxy,
   (e) $(C_1-C_6)$-$S(O)_n$-,
   (f) phenyl-$(C_1-C_6)$-alkyloxy,
   (g) cyano,
   (h) nitro,
   (i) vinyl,
   (j) $NR^4R^5$,
   (k) $NR^4COC_1-C_6$-alkyl,
   (l) CHO,
   (m) $CO_2H$,
   (n) $COC_1-C_6$-alkyl,
   (o) $CO_2C_1-C_6$-alkyl,
   (p) $CONR^4R^5$,
   (q) aryl, wherein aryl is as defined above,
   (r) heteroaryl, wherein heteroaryl is as defined above, and (s) heterocyclyl, wherein heterocyclyl is as defined above;
(4) $(C_2-C_{10})$-alkynyl, wherein alkynyl is unsubstituted or substituted with one or two of the substituents selected from the group consisting of:
(a) halo, wherein halo is fluoro, chloro, bromo, or iodo,
(b) hydroxy,
(c) oxo,
(d) $(C_1-C_6)$-alkyloxy,
(e) $(C_1-C_6)$-S(O)$_n$-,
(f) phenyl-$(C_1-C_6)$-alkyloxy,
(g) cyano,
(h) nitro,
(i) vinyl,
(j) $NR^4R^5$,
(k) $NR^4COC_1-C_6$-alkyl,
(l) CHO,
(m) $CO_2H$,
(n) $COC_1-C_6$-alkyl,
(o) $CO_2C_1-C_6$-alkyl,
(p) $CONR^4R^5$,
(q) aryl, wherein aryl is as defined above,
(r) heteroaryl, wherein heteroaryl is as defined above, and
(s) heterocyclyl, wherein heterocyclyl is as defined above; or
(5) cyano;
$R^4$ and $R^5$ are independently:
(1) hydrogen,
(2) $C_1-C_6$ alkyl, or
(3) aryl, wherein aryl is defined above,
$R^6$ is:
(1) hydrogen,
(2) oxo and a is a single bond,
(3) $O[(C=O)O_r]_sR^{11}$,
(4) $O[(C=O)O_r]_s$aryl, aryl as defined above,
(5) $O[(C=O)O_r]_s$heteroaryl, heteroaryl as defined above,
(6) $OC(=O)NR^{11}R^{12}$,
(7) $NR^{11}R^{12}$, or
(8) absent when a is a double bond;
$R^7$, $R^8$ and $R^9$ are independently selected from the group consisting of:
(1) hydrogen,
(2) oxo,
(3) $O[(C=O)O_r]_sR^{11}$,
(4) $O[(C=O)O_r]_s$aryl, aryl as defined above,
(5) $O[(C=O)O_r]_s$heteroaryl, heteroaryl as defined above,
(6) $OC(=O) NR^{11}R^{12}$, and
(7) $NR^{11}R^{12}$; and
$R^{10}$, $R^{11}$ and $R^{12}$ are independently chosen from the group consisting of:
(1) H, and
(2) $(C_1-C_6)$-alkyl, wherein alkyl is unsubstituted or substituted with one, two or three substituents selected from the group consisting of: Br, Cl, F, I, $(C_1-C_6)$-alkoxy, vinyl, cyano, oxo, nitro, hydroxy, CHO, $CO_2H$, $COC_1-C_6$-alkyl, $CO_2C_1-C_6$-alkyl, $CONR^4R^5$, $NR^4R^5$, $NR^4COC_1-C_6$-alkyl, aryl, wherein aryl is defined as phenyl or naphthyl, unsubstituted or substituted with one, two or three substituents selected from the group consisting of: Br, Cl, F, I, $(C_1-C_6)$-alkoxy, phenyl, phenoxy, cyano, oxo, nitro, hydroxy, CHO, $CO_2H$, $COC_1-C_6$-alkyl, $CO_2C_1-C_6$-alkyl, $CONR^4R^5$, $NR^4R^5$, $NR^4COC_1-C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, $(C_1-C_6)$-alkoxy, cyano, oxo, nitro, hydroxy, CHO, $CO_2H$, $COC_1-C_6$-alkyl, $CO_2C_1-C_6$-alkyl, $CONR^4R^5$, $NR^4R^5$, $NR^4COC_1-C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring.

A subembodiment of the invention are the compounds of Formula I wherein X is oxygen. Another subembodiment of the invention are the compounds of Formula I wherein X is H and $R^{10}$.

A preferred embodiment is the compound of structural Formula I:

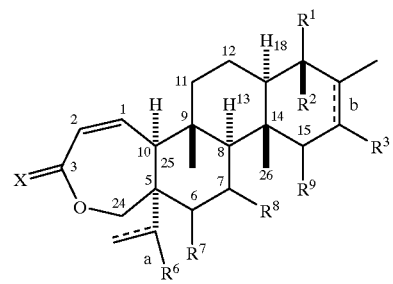

I or a pharmaceutically acceptable salt, crystal form, or hydrate, wherein:
X is: O or H and $R^{10}$;
$R^3$ is:
(1) H, or
(2) $(C_1-C_3)$-alkyl, wherein alkyl is unsubstituted or substituted with one or two of the substituents selected from the group consisting of:
(a) halo, wherein halo is fluoro, chloro, bromo, iodo,
(b) hydroxy,
(c) oxo,
(d) $(C_1-C_6)$-alkyloxy,
(e) $(C_1-C_6)$-S(O)$_n$-,
(f) aryl-$(C_1-C_6)$-alkyloxy,
(g) cyano,
(h) nitro,
(i) vinyl,
(j) $NR^4R^5$,
(k) $NR^4COC_1-C_6$-alkyl,
(l) CHO,
(m) $CO_2H$,
(n) $COC_1-C_6$-alkyl,
(o) $CO_2C_1-C_6$-alkyl,
(p) $CONR^4R^5$,
(q) aryl, wherein aryl is defined as phenyl or naphthyl, unsubstituted or substituted with one, two or three of the substituents selected from the group consisting of:
(a') halo, as defined above,
(b') hydroxy,
(c') $(C_1-C_6)$-alkyl, (d') $(C_1-C_4)$-perfluoroalkyl,
(e') $(C_1-C_6)$-alkenyl,
(f') $(C_1-C_6)$-alkynyl,
(g') $(C_1-C_6)$-alkyloxy,
(h') $(C_1-C_6)$-alkyl-$S(O)_n$-,
(i') phenyl,
(j') phenoxy,
(k') cyano,
(l') nitro,
(m') $CO_2H$,
(n') $COC_1-C_6$-alkyl,
(o') $CO_2C_1-C_6$-alkyl,
(p') $CONR^4R^5$,
(q') $NR^4R^5$, and
(r') $NR^4COC_1-C_6$-alkyl,
(r) $Si(R^4)_3$,
(3) $(C_2-C_3)$-alkenyl, wherein alkenyl is unsubstituted or substituted with one or two of the substituents selected from the group consisting of:
(a) halo, wherein halo is fluoro, chloro, bromo, or iodo,
(b) hydroxy,
(c) oxo,
(d) $(C_1-C_6)$-alkyloxy,
(e) $(C_1-C_6)$-$S(O)_n$-,
(f) phenyl-$(C_1-C_6)$-alkyloxy,
(g) cyano,
(h) nitro,
(i) vinyl,
(j) $NR^4R^5$,
(k) $NR^4COC_1-C_6$-alkyl,
(l) CHO,
(m) $CO_2H$,
(n) $COC_1-C_6$-alkyl,
(o) $CO_2C_1-C_6$-alkyl,
(p) $CONR^4R^5$,
(q) aryl, wherein aryl is as defined above,
(r) heteroaryl, wherein heteroaryl is as defined above, and
(s) heterocyclyl, wherein heterocyclyl is as defined above;
(4) $(C_2-C_3)$-alkynyl, wherein alkynyl is unsubstituted or substituted with one or two of the substituents selected from the group consisting of:
(a) halo, wherein halo is fluoro, chloro, bromo, or iodo,
(b) hydroxy,
(c) oxo,
(d) $(C_1-C_6)$-alkyloxy,
(e) $(C_1-C_6)$-$S(O)_n$-,
(f) phenyl-$(C_1-C_6)$-alkyloxy,
(g) cyano,
(h) nitro,
(i) vinyl,
(j) $NR^4R^5$,
(k) $NR^4COC_1-C_6$-alkyl,
(l) CHO,
(m) $CO_2H$,
(n) $COC_1-C_6$-alkyl,
(o) $CO_2C_1-C_6$-alkyl,
(p) $CONR^4R^5$,
(q) aryl, wherein aryl is as defined above,
(r) heteroaryl, wherein heteroaryl is as defined above, and
(s) heterocyclyl, wherein heterocyclyl is as defined above; or
(5) cyano;

$R^4$ and $R^5$ are independently:
(1) hydrogen,
(2) $C_1-C_3$ alkyl, or
(3) phenyl,
$R^6$ is:
(1) hydrogen,
(2) oxo and a is a single bond,
(3) $O(C=O)R^{11}$, or
(4) absent when a is a double bond;
$R^7$, $R^8$ and $R^9$ are independently selected from the group consisting of:
(1) hydrogen,
(2) oxo,
(3) $O(C=O)R^{11}$; and
$R^{10}$, $R^{11}$ and $R^{12}$ are independently chosen from the group consisting of:
a) H, and
b) $(C_1-C_3)$-alkyl.

Another preferred embodiment is the compound of structural Formula I:

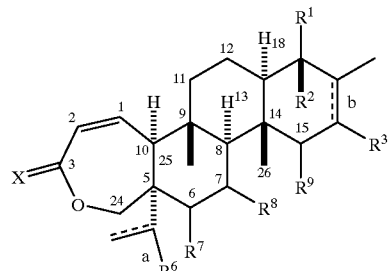

I or a pharmaceutically acceptable salt, crystal form, or hydrate, wherein:
X is O or H and $R^{10}$;
$R^1$ is:
(1) H,
(2) =O, when $R^2$ is absent,
(3) $(C_1-C_8)$-alkyl, wherein alkyl is unsubstituted or substituted with one or two of the substituents selected from the group consisting of:
(a) halo, wherein halo is fluoro, chloro, bromo, or iodo,
(b) hydroxy,
(c) oxo,
(d) $(C_1-C_3)$-alkyloxy,
(e) CHO,
(g) $CO(C_1-C_3)$-alkyl,
(i) aryl, wherein aryl is defined as phenyl or naphthyl, unsubstituted or substituted with one, two or three of the substituents selected from the group consisting of:
(a') halo, as defined above,
(b') hydroxy,
(c') $(C_1-C_6)$-alkyl,
(d') $(C_1-C_4)$-perfluoroalkyl,
(e') $(C_1-C_6)$-alkenyl,
(f') $(C_1-C_6)$-alkynyl,
(g') $(C_1-C_6)$-alkyloxy,
(h') $(C_1-C_6)$-alkyl-$S(O)_n$-,
(i') phenyl,
(j') phenoxy,
(k') cyano, (l') nitro,
(m') CO$_2$H,
(n') COC$_1$–C$_6$-alkyl,
(o') CO$_2$C$_1$–C$_6$-alkyl,
(p') CONR$^4$R$^5$,
(q') NR$^4$R$^5$,
(r') NR$^4$COC$_1$–C$_6$-alkyl,
(s') (C$_1$–C$_6$)-alkenyloxy, and
(t') benzyloxy;
(j) heteroaryl, wherein heteroaryl is defined as pyridyl or thienyl,
(4) (C$_2$–C$_6$)-alkenyl, wherein alkenyl is unsubstituted or substituted with aryl, wherein aryl is as defined above; and
(5) (C$_2$–C$_3$)-alkynyl, wherein alkynyl is unsubstituted or substituted with phenyl or Si(R$^4$)$_3$, or
(6) an exo-methylene group, when R$^2$ is absent;
R$^3$ is:
(1) H, or
(2) (C$_1$–C$_3$)-alkyl, wherein alkyl is unsubstituted or substituted with phenyl or Si(R$^4$)$_3$
(3) (C$_2$–C$_3$)-alkenyl, wherein alkenyl is unsubstituted or substituted with aryl, wherein aryl is defined as phenyl or naphthyl, unsubstituted or substituted with one, two or three of the substituents selected from the group consisting of:
(a') halo, as defined above,
(b') hydroxy,
(c') (C$_1$–C$_6$)-alkyl,
(d') (C$_1$–C$_4$)-perfluoroalkyl,
(e') (C$_1$–C$_6$)-alkenyl,
(f') (C$_1$–C$_6$)-alkynyl,
(g') (C$_1$–C$_6$)-alkyloxy,
(h') (C$_1$–C$_6$)-alkyl-S(O)$_n$-,
(i') phenyl,
(j') phenoxy,
(k') cyano,
(l') nitro,
(m') CO$_2$H,
(n') COC$_1$–C$_6$-alkyl,
(o') CO$_2$C$_1$–C$_6$-alkyl,
(p') CONR$^4$R$^5$,
(q') NR$^4$R$^5$,
(r') NR$^4$COC$_1$–C$_6$-alkyl,
(s') (C$_1$–C$_6$)-alkenyloxy, and
(t') benzyloxy;
(4) cyano;
R$^4$ and R$^5$ are independently:
(1) hydrogen,
(2) C$_1$–C$_3$ alkyl, or
(3) phenyl,
R$^6$ is:
(1) hydrogen,
(2) oxo and a is a single bond,
(3) O(C=O)R$^{11}$, or
(4) absent when a is a double bond;
R$^7$, R$^8$ and R$^9$ are independently selected from the group consisting of:
(1) hydrogen,
(2) oxo,
(3) O(C=O)R$^{11}$; and R$^{10}$, R$^{11}$ and R$^{12}$ are independently chosen from the group consisting of:
a) H, and
b) (C$_1$–C$_3$)-alkyl.

A most preferred embodiment is a compound selected from the group consisting of:

[5-S-5aα,7aα,8α,8β,11β,11aβ,11bα,12α,12α,13α,13aα]-13a-(1-R-acetoxyethyl)-8 -hydroxy-8-(2-(2-ethoxyphenyl)ethyl)-11,12,13-triacetoxy-5b,9,11a-trimethyl-1,3,5a,5b,6,7,7a,8,11,11a,11b,12,13,13a-tetradecahydrophenanthro [2,1-c]oxepin;

[5-S-5aα,7aα,8α,8β,11β,11aβ,11bα,12α,13α,13aα]-13a-(1-R-acetoxyethyl)-8 -hydroxy-8-(2-(2-n-butyloxyphenyl)ethyl)-11,12,13-triacetoxy-5 b,9,11a-trimethyl-1,3,5a,5b,6,7,7a,8,11,11a,11b,12,13,13a-tetradecahydrophenanthro [2,1-c]oxepin;

[5-S-5aα,5aα,7aα,8α,8β,11β,11aβ,11bβ,12β,13β,13aβ]-13a-(1-R-acetoxyethyl )-8-hydroxy-8-(2-(2-n-allyloxyphenyl)ethyl)-11,12,13-triacetoxy-5b,9,11a-trimethyl-1,3,5a,5b,6,7,7a,8,11,11a,11b,12,13,13a-tetradecahydrophenanthro [2,1-c]oxepin;

[5-S-5aα,5aα,7aα,8α,8β,11β11aβ,11bα,12α,13α,13aα]-13a-(1-R-acetoxyethyl)-8-hydroxy-8-(2-phenylethyl)-11,12,13-triacetoxy-5b,9,11a-trimethyl-1,3,5a,5b,6,7,7a,8,11,11a,11b,12,13,13a-tetradecahydrophenanthro[2,1-c]oxepin;

[5-S-5aα,5aα,7aα,8α,8β,11β,11aβ,11bα,12α,13α,13aα]-13a-(1-R-acetoxyethyl)-8-hydroxy-8-(but-3-en-1-yl)-11,12,13-triacetoxy-5b,9,11a-trimethyl-1, 3,5a,5b,6,7,7a,8,11,11a,11b,12,13,13a-tetradecahydrophenanthro[2,1-c]oxepin;

[5-S-5aα,5aα,7aα,8α,8β,11β,11aβ,11bα,12α,13α,13aα]-(1-R-acetoxyethyl)-8-hydroxy-8-(4,4-dimethylbut-3-en-1-yl)-11,12,13-triacetoxy-5b,9,11a-trimethyl-1,3,5a,5b,6,7,7a,8,11,11a,11b,12,13,13a-tetradecahydrophenanthro[2,1-c]oxepin;

[5-S-5aα,5aα,7aα,8α,8β,11β,11aβ,11bα,12α,13α,13aα]-13a-(1-R-acetoxyethyl)-8-hydroxy-8-(2-(2-methylphenyl)ethyl)-11,12,13-triacetoxy-5b,9,11a-trimethyl-1,3,5a,5b,6,7,7a,8,11,11a,11b,12,13,13a-tetradecahydrophenanthro [2,1-c]oxepin;

[5-S-5aα,5aα,7aα,8α,8β,11β,11aβ,11bα,12α,13α,13aα]-13a-(1-R-acetoxyethyl)-8-hydroxy-8-(2-(2-methoxyphenyl)ethyl)-11,12,13-triacetoxy-5 b,9,11a-trimethyl-1,3,5a,5b,6,7,7a,8,11,11a,11b,12,13,13a-tetradecahydrophenanthro[2,1-c]oxepin;

[5-s-5aα,5aα,7aα,8α,8β,11β,11aβ,11bα,12α,13α,13aα]-13a-(1-R-acetoxyethyl)-8-hydroxy-8-(S-2-(phenyl)propyl)-11,12,13-triacetoxy-5 b,9,11a-trimethyl-1,3,5a,5b,6,7,7a,8,11,11a,11b,12,13,13a-tetradecahydrophenanthro [2, 1-c]oxepin;

[5-S-5aa,5aa,7aa,8a,8b,11b,11ab,11ba,12a,13a,13aa]-13a-(1-R-acetoxyethyl)-8-hydroxy-8-(2-( phenyl)prop-2-enyl)-11,12,13-triacetoxy-5 b,9,11a-trimethyl-1,3,5a,5b,6,7,7a,8,11,11a,11b,12,13,13a-tetradecahydrophenanthro [2,1-c]oxepin;

[5-S-5aa,5aa,7aa,8a,8b,11b,11ab,11ba,12a,13a,13aa]-13a-(1-R-acetoxyethyl)-8-hydroxy-8-(R-2-phenylpropyl)-11,12,13-triacetoxy-5b,9,11a-trimethyl-1, 3,5a,5b,6,7,7a,8,11,11a,11b,12,13,13a-tetradecahydrophenanthro [2,1-c]oxepin;

[5-S-5aα,5aα,7aα,8α,8β,11β,11aβ,11bα,12α,13α,13aα]-13a-(1-R-acetoxyethyl)-8-hydroxy-8-(2-(phenyl)prop-2-enyl)-11,12,13-triacetoxy-5b,9,11a-trimethyl-1,3,5a,5b,6,7,7a,8,11,11a,11b,12,13,13a-tetradecahydrophenanthro [2,1-c]oxepin-3-one;

[5-S-5aa,5aa,7aa,8a,8b,11b,11ab,11ba,12a,13a,13aa]-13a-(1-R-acetoxyethyl)-8-hydroxy-8-(2-(2-methoxyphenyl)

prop-2-enyl)-11,12,13-triacetoxy-5b,9,11a-trimethyl-1,3,5a, 5b,6,7,7a,8,11,11a,11b,12,13,13a-tetradecahydrophenanthro [2, 1-c]oxepin;

[5-S-5aα,5aα,7aα,8α,8β,11β,11aβ,11bα,12α,13α, 13aα]-13a-(1-R-acetoxyethyl)-8-hydroxy-8-(2-(2-ethylmercaptophenyl)prop-2-enyl)-11, 12,13-triacetoxy-5b, 9,11a-trimethyl-1,3,5a,5b,6,7,7a,8,11,11a,11b, 12,13,13a-tetradecahydrophenanthro[2,1-c]oxepin;

[5-S-5aα,5aα,7aα,8α,8β,11β,11aβ,11bα,12α,13α, 13aα]-13a-(1-R-acetoxyethyl)-8-hydroxy-8-(2-(2-ethylphenyl)prop-2-enyl)-11,12,13-triacetoxy-5b,9,11a-trimethyl-1,3,5a,5b,6,7,7a,8,11,11a,11b,12,13,13a-tetradecahydrophenanthro [2,1-c]oxepin;

[5-S-5aα,5aα,7aα,8α,8β,11β,11aβ,11bα,12α,13α, 13aα]-13a-(1-R-acetoxyethyl)-8-hydroxy-8-(2-(2-methylmercaptophenyl)prop-2-enyl)-11, 12,13-triacetoxy-5b,9,11a-trimethyl-1,3,5a,5b,6,7,7a,8,11,11a,11b, 12,13, 13a-tetradecahydrophenanthro[2,1-c]oxepin;

[5-S-5aα,5aα,7aα,8α,8β,11β,11aβ,11bα,12α,13α, 13aα]-13a-(1-R-acetoxyethyl)-8-hydroxy-8-(2-(2-ethylmercaptophenyl)prop-2-enyl)-11, 12,13-triacetoxy-5b, 9,11a-trimethyl-1,3,5a,5b,6,7,7a,8,11,11a,11b, 12,13,13a-tetradecahydrophenanthro[2,1-c]oxepin-3-one;

[5-S-5aα,5aα,7aα,8α,8β,11β,11aβ,11bα,12α,13α, 13aα]-13a-(1-R-acetoxyethyl)-8-hydroxy-8-(2-(2-n-butylmercaptophenyl)prop-2-enyl)-11, 12,13-triacetoxy-5b, 9,11a-trimethyl-1,3,5a,5b,6,7,7a,8,11,11a,11b, 12,13,13a-tetradecahydrophenanthro[2,1-c]oxepin-3-one;

[5-S-5aα,5aα,7aα,8α,8β,11β,11aβ,11bα,12α,13α, 13aα]-13a-(1-R-acetoxyethyl)-8-hydroxy-8-(2-(2-vinylphenyl)prop-2-enyl)-11,12,13-triacetoxy-5b,9,11a-trimethyl-1,3,5a,5b,6,7,7a,8,11,11a,11b,12,13,13a-tetradecahydrophenanthro [2,1-c]oxepin-3-one; and

[5-S-5aα,5aα,7aα,8α,8β,11β,11bα,12α,13α,13aα]-13a-(1-R-acetoxyethyl)-8-hydroxy-8-(2-(S)-(-)-(2-ethylphenyl) propyl)-11,12,13-triacetoxy-5 b,9,11a-trimethyl-1,3,5a,5b, 6,7,7a,8,11,11a,11b,12,13,13a-tetradecahydrophenanthro [2,1-c]oxepin.

The compounds of the present invention have asymmetric centers and this invention includes all of the optical isomers and mixtures thereof.

In addition compounds with carbon-carbon double bonds may occur in Z- and E- forms with all isomeric forms of the compounds being included in the present invention.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy.

"Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethyl pentenyl, and the like, and includes E and Z forms, where applicable. "Halogen", as used herein, means fluoro, chloro, bromo and iodo.

The term "aryl" is defined as a phenyl or naphthyl ring which is optionally substituted with the substituents listed above at any available carbon atoms. The aryl may also be substituted with a fused 5-, 6-, or 7-membered ring containing one or two oxygens and the remaining ring atoms being carbon, the fused 5-, 6-, or 7-ring being selected from the group consisting of: dioxolanyl, dihydrofuranyl, dihydropyranyl, and dioxanyl.

The term "heteroaryl" as utilized herein, unless specifically defined otherwise, is intended to include the following: a 5 or 6-membered ring substituted with one, two or three heteroatoms selected from O, S, N, and is unsubstituted or substituted with one, two or three substituents selected from the group consisting of: Br, Cl, F, I, $(C_1-C_6)$-alkoxy, cyano, nitro, hydroxy, CHO, $CO_2H$, $COC_1-C_6$-alkyl, $CO_2C_1-C_6$-alkyl, $CONR^1R^2$, $NR^{11}R^{12}$, $NR^{11}COC_1-C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, pyrazinyl, pyridazinyl, pyridinyl, pyrimidinyl, and pyrrolyl which are substituted or unsubstituted as defined above.

In the compounds of Formula I, the heteroaryl group may be optionally substituted with the substituents listed above at any available carbon atom or nitrogen atom (if present), but compounds bearing certain substitutents, directly substituted to a nitrogen may be relatively unstable and are not preferred. The heteroaryl may also be fused to a second 5-, 6-, or 7-membered ring containing one or two oxygens such as: dioxolanyl, dihydrofuranyl, dihydropyranyl, and dioxanyl.

The term "heterocyclyl" as utilized herein, unless specifically defined otherwise, is intended to include a cyclic, non-aromatic substituents containing from 1 to 3 heteroatoms selected from the group consisting of O, N, and S, said heterocyclyl substituent being itself unsubstituted or substituted with one, two or three substituents selected from the group consisting of: Br, Cl, F, I, $(C_1-C_6)$-alkoxy, cyano, nitro, hydroxy, CHO, $CO_2H$, $COC_1-C_6$-alkyl, $CO_2C_1-C_6$-alkyl, $CONR^1R^2$, $NR^{11}R^{12}$, $NR^{11}COC_1-C_6$-alkyl. Representative heterocyclyl substituents include, but are not limited to the following: piperidinyl, morpholinyl, pyrrolidinyl, tetrahydrofuranyl, imidazolinyl, piperazinyl, pyrolidine-2-one, piperidine-2-one and the like.

Pharmaceutically acceptable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydroscopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

REACTION SCHEME A

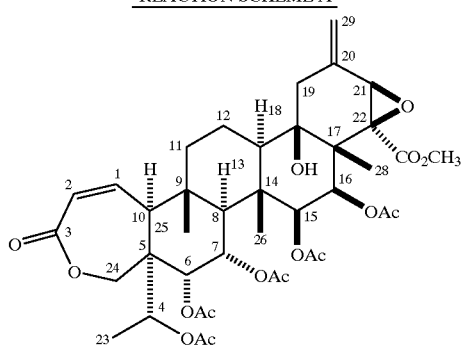

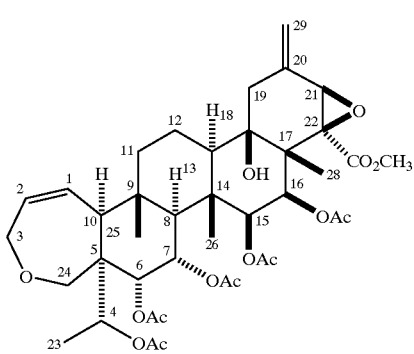

As seen in Scheme A, compound I [(4,6,7,15,16-pentakis (acetyloxy)-21,22-epoxy-18-hydroxy-22-methyoxycarbonyl-(6α, 7α, 15β, 16β, 21β, 22β)-D:A-Freido-A-homo-27,30-dinor-24-oxaoleana- 1, 20(29)-dien-3-one], isolated from *Spachea correa* can be converted to its oxepin analog in a two step process. U.S. Ser. No. 08/476, 806 filed on Jun. 7, 1995 describing the isolation of compound I and is hereby incorporated by reference. Lactone I is first reduced to the lactol. This can be accomplished by using a variety of reducing agents including di-isobutylaluminum hydride (Dibal) and sodium bis(2-methoxyethoxy) aluminum hydride (Red-Al). A more optimal reducing agent is the use of lithium tri-t-butoxyaluminum hydride in an inert solvent such as dichloromethane at reduced temperatures, preferably 0° C. The purified lactol intermediate is then reacted with triethylsilane and a Lewis acid such as borontrifluoride diethyl etherate to give the ether (oxepin) analog of I.

REACTION SCHEME B

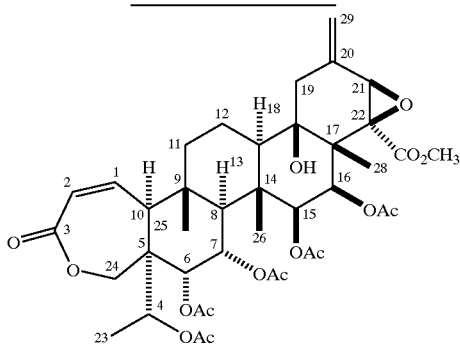

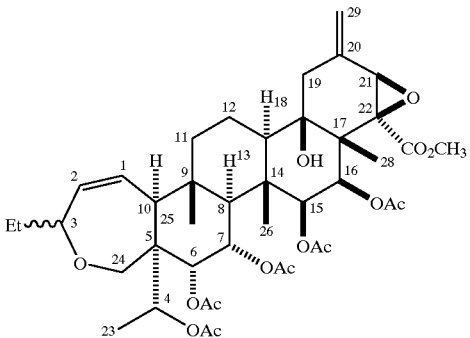

In a variation of Scheme A, oxepin derivatives substituted at C3 can also be prepared. Thus in Reaction Scheme B, lactone I or its reduced analog is first reduced to the lactol as described in Reaction Scheme A. The purified lactol intermediate is then reacted with a trialkylaluminum reagent, as exemplified in this scheme by triethyl-aluminum ($Et_3Al$) to give the ethyl derivative. The allyl derivative can be prepared with allyltrimethylsilane and a Lewis acid such as borontrifluoride diethyl etherate.

REACTION SCHEME C

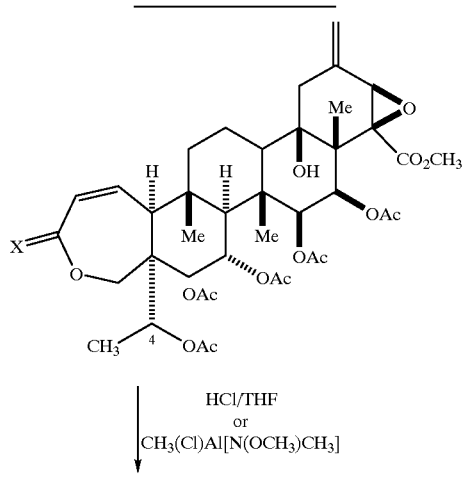

-continued

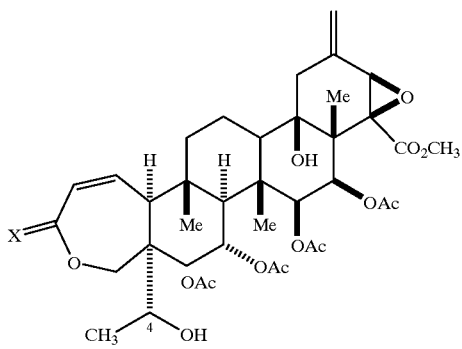

Lactone or ether derivatives can be selectively de-acetylated at C4 to give the corresponding alcohol by reacting it with an aqueous solution of HCl (preferably 2 M to 3 M concentration) in THF. It can also be prepared by reacting I with $CH_3(Cl)Al[N(OCH_3)CH_3$ (Weinreb reagent) in inert solvents such as THF, toluene or methylene chloride.

REACTION SCHEME D

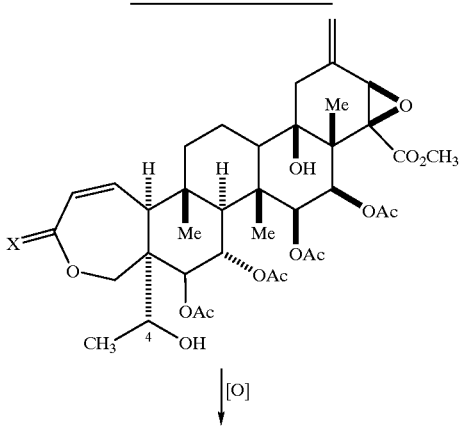

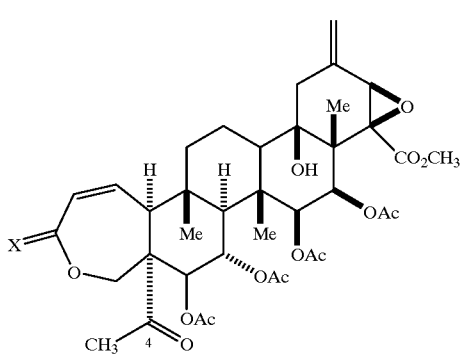

The C4 hydroxy group can be oxidized to the corresponding ketone by a variety of oxidizing agents. The Jones reagent (chromic acid and sulfuric acid in $H_2O$), pyridinium chlorochromate, and oxalyl chloride plus DMSO all will achieve this conversion.

REACTION SCHEME E

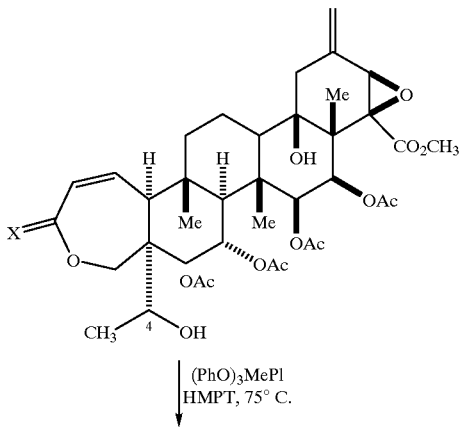

$(PhO)_3MePI$
HMPT, 75° C.

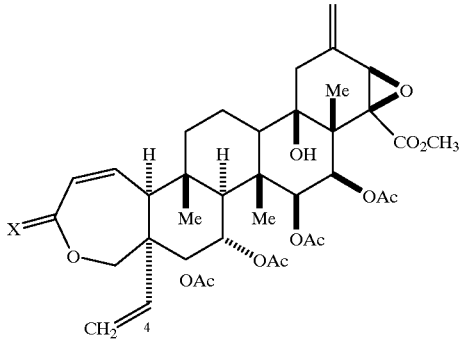

The C4 hydroxy group can also be dehydrated to give the olefin. Reaction of the alcohol with tris-phenoxymethylphosphonium iodide in hexamethylphosphorous triamide (HMPT) at 75° C. will achieve this conversion.

REACTION SCHEME F
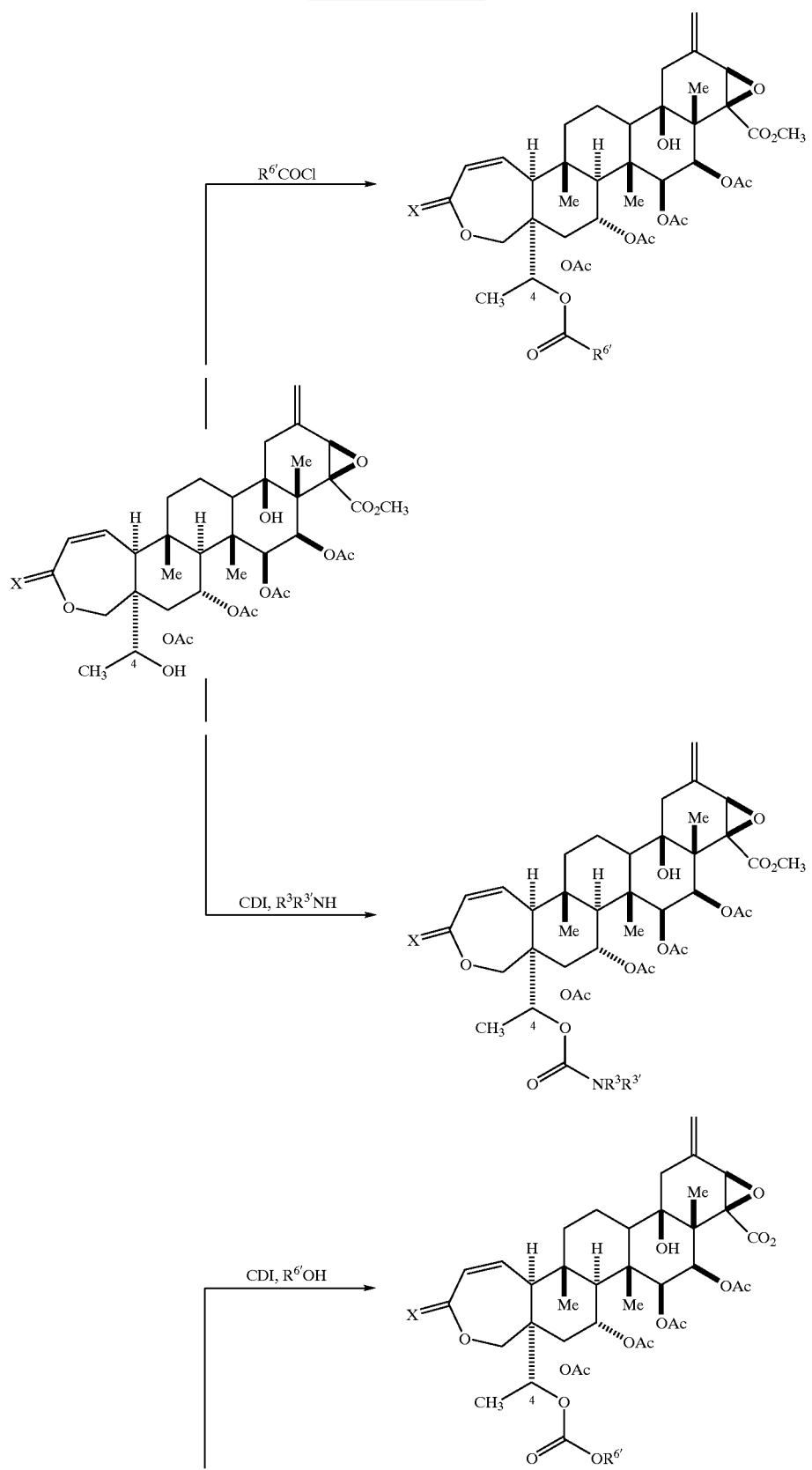

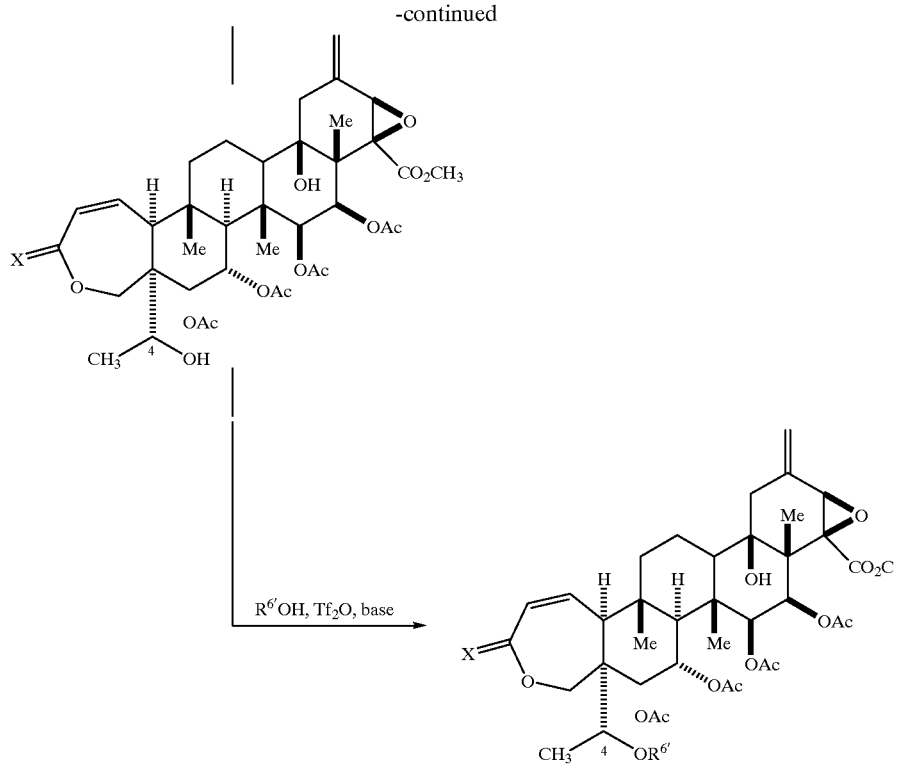

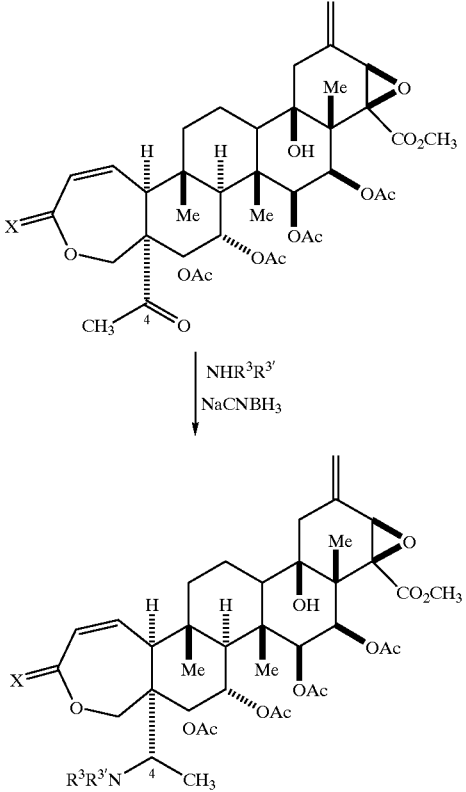

REACTION SCHEME G

As depicted in Reaction Scheme F, esters at C4 can be prepared by reaction of a preformed carboxylic acid chloride with the C4 alcohol derivative (Reaction Scheme C) in a basic solvent such as pyridine. It should be understood that $R^{6'}$ is used to represent a portion of the $R^6$ definition, e.g. $R^6$ can be an alkyl carbonate which is depicted in the scheme as $OC(=O)OR^{6'}$, $R^{6'}$ representing the alkyl substituent. The acid chlorides, when not purchased, are prepared by stirring the carboxylic acids in reagents such as oxalyl chloride or thionyl chloride. Esters may also be prepared by reaction of the acid chloride and C4 alcohol with silver cyanide (AgCN) in an aprotic solvent such as HMPA. C4 sulfonate derivatives are prepared in a similar manner by reaction with sulfonyl chlorides.

C4 carbonate and carbamate derivatives are prepared by first reacting the C4 alcohol derivative with carbonyldiimidazole (CDI) to obtain the imidazolecarbonyl intermediate which is then reacted with an alcohol or amine ($R^3R^{3'}NH$) to give the corresponding carbonate or carbamate derivatives.

C4 ether derivatives can also be prepared. The best procedure involves reacting an alcohol with trifluoromethanesulfonic anhydride ($Tf_2O$, triflic anhydride) to obtain the preformed triflate in dichloromethane at reduced temperature, preferably −78° C. To this solution is added the triterpene alcohol, the reaction mixture is warmed to room temperature and stirring is continued until reaction is complete. Ethers may also be prepared by heating a mixture of triterpene C4 alcohol, the appropriate alkylhalide and an excess of silver oxide ($Ag_2O$) in an aprotic invert solvent such as THF.

Amines at C4 can be prepared from the C4 ketone described in Reaction Scheme D by reaction with an amine $NHR^3R^{3'}$ in a variety of solvents with a reducing agent such as sodium cyanoborohydride.

REACTION SCHEME H

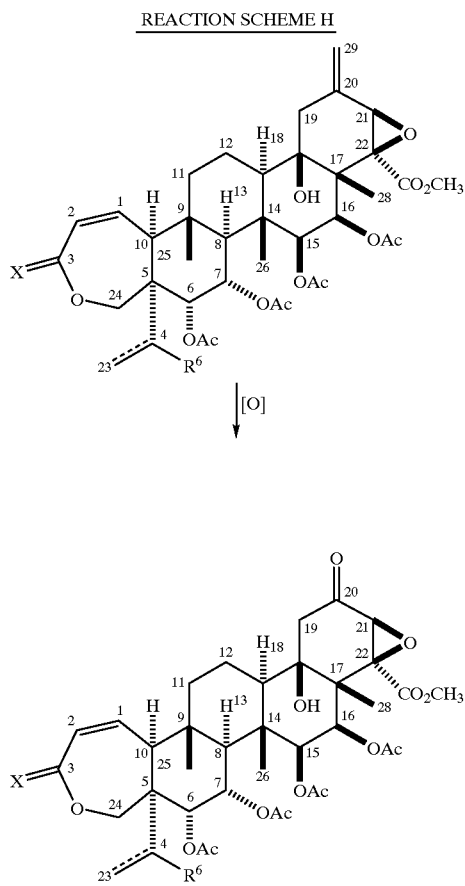

[O]

↓

The C20–29 olefin can be selectively converted to the corresponding ketone by a variety of oxidative cleavage procedures. Ozonization ($O_3$) at reduced temperatures, preferrably at $-78°$ C. in dichloromethane and methanol gives the ketone in good yield. Alternatively, the C20 ketone can be prepared by sequential reaction with osmium tetroxide or ruthenium tetroxide and sodium periodate.

REACTION SCHEME I

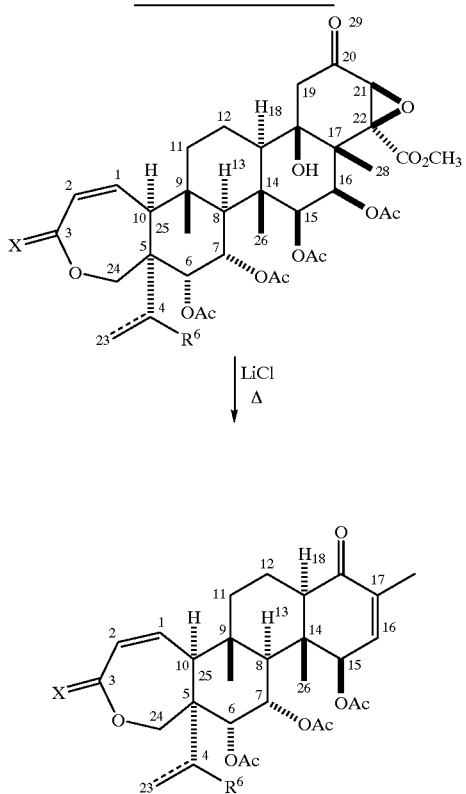

LiCl
Δ
↓

Reaction of the pentacyclic ketone with a metalhalide such as LiCl in a solvent such as DMF or DMSO at elevated temperatures such as 100° C. results in ring cleavage to obtain the tetracyclic enone depicted.

REACTION SCHEME J

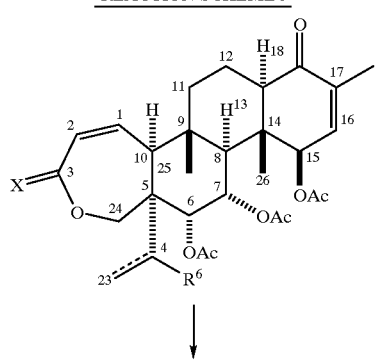

↓

-continued

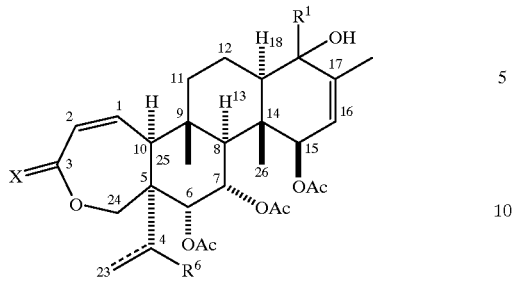

When X is hydrogen or $R^1$, the C18 ketone can be reacted with nucleophiles ($R^{1-}M^+$) to give C18 substituted hydroxy derivatives. In general, Grignard reagents ($R^1MgBr$) or alkyllithium reagents ($R^1Li$) are utilized in aprotic solvents such as diethyl ether or THF.

Allylsilane reagents also add to the C18 ketone. For instance, reaction with allyltrimethylsilane and titanium tetrachloride in THF or diethyl ether gives the allyl adduct. This latter procedure is the preferred route when X=O.

REACTION SCHEME K

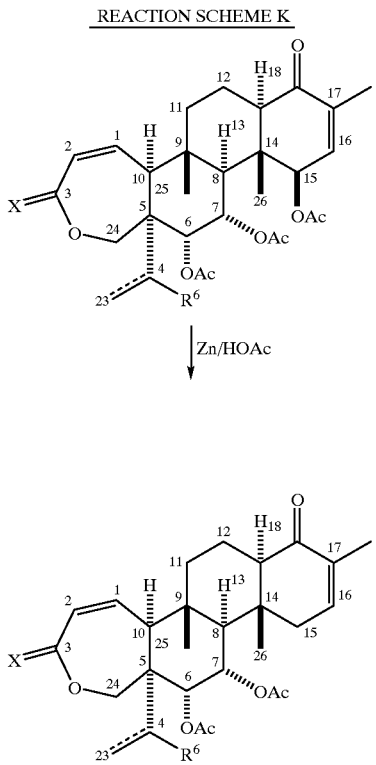

The acetoxy group at position 15 can be selectively removed from the ketone precursor shown in excellent yield by refluxing in acetic acid with Zn powder. The C18 ketone can then be derivatized accoroding to methods described in Reaction scheme J.

REACTION SCHEME L

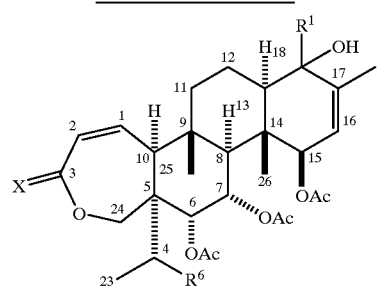

$K_2CO_3$, MeOH, reflux

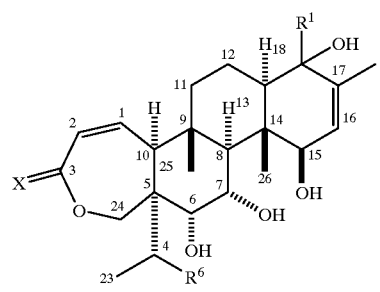

It was already shown in Reaction Scheme C that the acetate group at position 4 can be selectively removed. The acetate groups at positions 6, 7 and 15 can be removed by reaction with $K_2CO_3$ in refluxing methanol.

REACTION SCHEME M

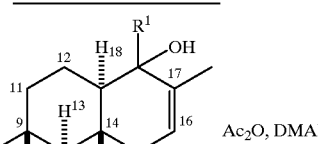

$Ac_2O$, DMAP pyridine, THF

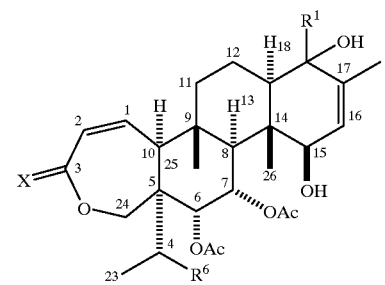

-continued

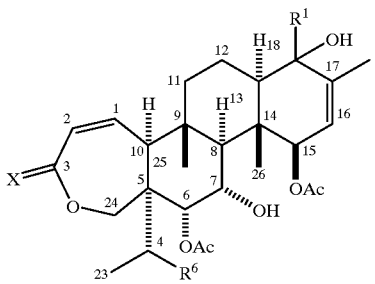

Treatment of the hydroxy derivative from Reaction Scheme N gives the C15 and C7 hydroxy derivatives shown in this scheme. Similar reactions can be performed on this starting material. For instance, reaction with acetone with catalysis with PTSA gives a mixture of acetonides, primarily at C6/C7 and C7/C15. Other ester, carbamate and ether derivatives can be prepared using procedures described in Reaction Scheme F.

REACTION SCHEME N

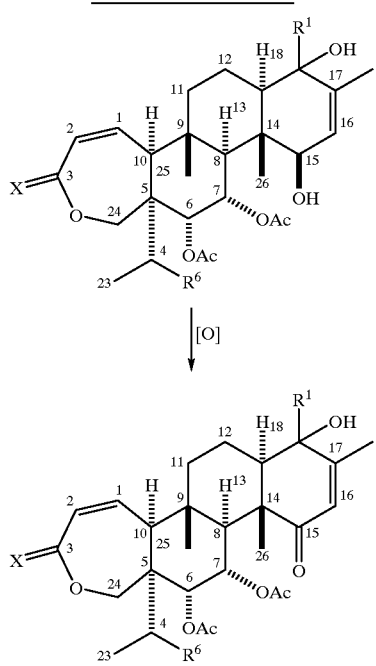

The C15 hydroxy group can be oxidized to the corresponding ketone by a variety of oxidizing agents. The Jones reagent (chromic acid and sulfuric acid in $H_2O$), pyridinium chlorochromate, and oxalyl chloride plus DMSO all will achieve this conversion.

UTILITY

The present invention is related to compounds of formula I, including but not limited to those specified in the examples, which are useful in a mammalian subject for the treatment and prevention of immunemediated diseases such as the resistance by transplantation of organs or tissue such as heart, kidney, liver, medulla ossium, skin, cornea, lung, pancreas, intestinum tenue, limb, muscle, nervus, duodenum, small-bowel, pancreatic-islet-cell, including xeno transplants, etc.; graft-versus-host diseases brought about by medulla ossium transplantation; autoimmune diseases such as rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, and the like; and further infectious diseases caused by pathogenic microorganisms. Further uses may include the treatment and prophylaxis of inflammatory and hyperproliferative skin diseases and cutaneous manifestations of immunologically mediated illnesses, such as psoriasis, atopical dermatitis, contact dermatitis and further eczematous dermatitises and further eczematous dermatitises, seborrhoeis dermatitis, *Lichen planus*, Pemphigus, bullous pemphigoid, *Epidermolysis bullosa*, urticaria, angioedemas, vasculitides, erythemas, cutaneous eosinophilias, *Lupus erythematosus*, acne and *Alopecia areata*; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, which includes condition such as asthma (for example, bronchial asthma, allergic asthma, intrinsic asthma, extrinsic asthma and dust asthma), particularly chronic or inveterate asthma (for example, late asthma and airway hyper-responsiveness), bronchitis and the like; inflammation of mucous and blood vessels such as gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastrointestinal tract (e.g. migraine, rhinitis and eczema); renal diseases such as interstitial nephritis, Good-pasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fascitis; periodontal disease such as lesions of gingiva, periodontium, alveolar bone and substantia ossea dentis; nephrotic syndrome such as glomerulonephritis; male pattern alopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g. necrosis caused by toxin, viral hepatitis, shock, or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmention of chemotherapeutic effect, preventing or treating activity of cytomegalovirus infection, particularly HCMV infection, and antiinflammatory activity; and The compounds of the present invention may also be used in the treatment of immunodepression or a disorder involving immunodepression, such as AIDS, cancer, senile dementia, trauma (including wound healing, surgery and shock) chronic bacterial infection, and certain central nervous system disorders.

A method of treating a condition in a mammal, the treatment of which is effected or facilitated by $K_v1.3$ inhibition, comprising the administration, in an amount that is effective at inhibiting $K_v1.3$, of a compound of Formula I. The method of treating a condition in a mammal, the treatment of which is effected or facilitated by $K_v1.3$ inhibition, wherein the condition is selected from the group consisting of: immunemediated diseases such as the resistance by transplantation of organs or tissue such as heart, kidney, liver, medulla ossium, skin, cornea, lung, pancreas, intestinum tenue, limb, muscle, nervus, duodenum, small-bowel, pancreatic-islet-cell, including xeno transplants, etc.; graft-versus-host diseases brought about by medulla ossium transplantation; autoimmune diseases such as rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, and the like; and further infectious diseases caused by pathogenic microorganisms. Further uses may include the treatment and prophylaxis of inflammatory and hyperproliferative skin diseases and cutaneous manifestations of immunologically mediated illnesses, such as psoriasis, atopical dermatitis, contact dermatitis and further eczematous dermatitises and further eczematous dermatitises, seborrhoeis dermatitis, *Lichen planus*, Pemphigus, bullous pemphigoid, *Epidermolysis bullosa*, urticaria, angioedemas, vasculitides, erythemas, cutaneous eosinophilias, *Lupus erythematosus*, acne and *Alopecia areata*; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, which includes condition such as asthma (for example, bronchial asthma, allergic asthma, intrinsic asthma, extrinsic asthma and dust asthma), particularly chronic or inveterate asthma (for example, late asthma and airway hyper-responsiveness), bronchitis and the like; inflammation of mucous and blood vessels such as gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastrointestinal tract (e.g. migraine, rhinitis and eczema); renal diseases such as interstitial nephritis, Good-pasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fasciitis; periodontal disease such as lesions of gingiva, periodontium, alveolar bone and substantia ossea dentis; nephrotic syndrome such as glomerulonephritis; male pattern aleopreia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g. necrosis caused by toxin, viral hepatitis, shock, or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmention of chemotherapeutic effect, preventing or treating activity of cytomegalo-virus infection, particularly HCMV infection, and antiinflammatory activity; and immunodepression or a disorder involving immunodepression, such as AIDS, cancer, senile dementia, trauma (including wound healing, surgery and shock), chronic bacterial infection, and certain central nervous system disorders.

An embodiment of the invention is a method for the treatment of autoimmune diseases. Another embodiment of the invention is a method for the prevention of rejection of foreign organ transplants comprising administering to a patient in need of such treatment a therapeutically effective amount of a compound of formula One end result of an autoimmune or a rejection process is tissue destruction caused by inflammatory cells and the mediators they release. Anti-inflammatory agents such as NSAID's and corticosteroids act principally by blocking the effect or secretion of these mediators, but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A, which was approved by the US FDA in 1983, is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting fewer side effects are constantly being searched for in the field. The present invention provides for immunosuppressant agents which are inhibitors of a voltage dependent potassium channel, $K_v1.3$ that is found on human T-lymphocytes.

Potassium channels modulate a number of cellular events such as muscle contraction, neuro-endocrine secretion, frequency and duration of action potentials, electrolyte homeostasis, and resting membrane potential. These channels comprise a family of proteins that have been classified according to their biophysical and pharmacological characteristics. Inhibition of $K^+$ channels, in their role as modulators of the plasma membrane potential in human T-lymphocytes, has been postulated to play a role in eliciting immunosuppressive responses. In regulating membrane potential, $K+$ channels play a role in the regulation of intracellular $Ca^{++}$ homeostasis, which has been found to be important in T-cell activation. The biochemical characterization of $K^+$ channels is underdeveloped, due to the paucity of selective high affinity probes.

Functional voltage-gated $K^+$ channels can exist as multimeric structures formed by the association of either identical or dissimilar subunits. This phenomena is thought to account for the wide diversity of $K^+$ channels. However, subunit compositions of native $K^+$ channels and the physiologic role that particular channels play are, in most cases, still unclear.

The $K_v1.3$ channel is a voltage-gated potassium channel that is found in neurons, blood cells, osteoclasts and T-lymphocytes. The Chandy and Cahalan laboratories proposed a hypothesis that blocking the $K_v1.3$ channel would elicit an immunosuppressant response. (Chandy et al., J. Exp. Med. 160, 369, 1984; Decoursey et al., Nature, 307, 465, 1984). However, the K+ channel blockers employed in their studies were non-selective. Until research with the peptide margatoxin, a peptide found in scorpion venom, no specific inhibitor of the $K_v1.3$ channel existed to test this hypothesis. Although a laboratory (Price et al., Proc. Natl. Acad. Sci. USA, 86, 10171, 1989) showed that charybdotoxin would block $K_v1.3$ in human T cells, charybdotoxin was subsequently shown to inhibit four different $K^+$ channels ($K_v1.3$ and three distinct small conductance $Ca^{++}$ activated $K^+$ channels) in human T-lymphocytes, limiting the use of this toxin as a probe for the physiological role of $K_v1.3$ (Leonard et al., Proc. Natl. Acad. Sci. USA, 89, 10094, 1992). Margatoxin, on the other hand, blocks only $K_v1.3$ in T-cells, and has immunosuppressant activity in both in vitro and in vivo models. (Lin et al., J. Exp. Med, 177, 637, 1993). Since the compounds of the embodiments of this invention produce blockade of $K_v1.3$, they will also inhibit T-cell activation.

Also within the scope of this invention is a method of treating a condition in a mammal, the treatment of which is effected or facilitated by $K_v1.3$ inhibition, comprising the administration of a pharmaceutical composition comprising a suitable pharmaceutical carrier and a compound of Formula (I), in an amount that is effective at inhibiting $K_v1.3$.

Also within the scope of this invention is a combination therapy comprising a compound of formula I and one or more immunosuppressant agents. These immunosuppressant agents within the scope of this invention include, but are not limited to, IMUREK® azathioprine sodium, brequinar sodium, SPANIDIN® gusperimus trihydrochloride (also known as deoxyspergualin), mizoribine (also known as bredinin), CELLCEPT® mycophenolate mofetil, NEORAL® Cyclosporin A (also marketed as a different formulation of Cyclosporin A under the trademark SANDIMMUNE®), PROGRAF® tacrolimus (also known as FK-506) and RAPIMMUNE® sirolimus (also known as rapamycin), leflunomide (also known as HWA-486), glucocortcoids, such as prednisolone and its derivatives, antibody therapies such as orthoclone (OKT3) and Zenapax and antithymyocyte globulins, such as thymoglobulins.

Using the methodologies described below, representative compounds of the invention were evaluated and found to exhibit IC50 values of at least <10 μM in any of the assays thereby demonstrating and confirming the utility of the compounds of the invention as $K_v1.3$ inhibitors and immunosuppressants.

T CELL IL-2 ASSAY

Peripheral blood mononuclear (MNC) cells from healthy donors were separated by density centrifugation with ficoll-hypaque (LSM, Organon Teknika, Durham, N.C.), followed by rosetted with neuraminidase treated sheep red blood cells (SRBC). After another centrifugation with leucocyte separation medium (LSM), the SRBC of the rosetted T cells were then lysed with ammonium chloride lysing buffer (GIBCO, Grand Island, N.Y.). Such purified T cells were resuspended at $3\times10^6$/ml in RPMI 1640 culture medium (GIBCO) supplemented with 10% fetal calf serum (Sigma, St. Louis, Mo.), 100 mM glutamine, 1 mM sodium pyruvate, 0.1 mM non-essential amino acids, and 1% penn-strep (GIBCO). The cell suspension was immediately distributed into 96 well round-bottom microculture plates (Costar) at 200 $\mu$l/well. The various dilutions of test compound were then added in triplicate wells at 25 $\mu$l/well, incubated for 30 min at 37° C. Ionomycin (125 ng/ml), and PMA (1 or 5 ng/ml), were added to the appropriate wells. The culture plates were then incubated at 37° C. in a humidified atmosphere of 5% $CO_2$-95% air for 18–24 hours. The supernatants were removed, and assayed for IL-2 with an IL-2 capture ELISA, using monoclonal anti-IL-2, and biotinylated goat anti-IL-2 antibodies (unconjugated antibodies purchased from R&D System, Minneapolis, Minn.). The ELISA was developed with streptavidin conjugated peroxidase (Zymed, San Francisco, Calif.) and substrate for peroxidase (Sigma). Mean OD and units of IL-2 of the replicate wells were calculated from standard curve, created with recombinant IL-2 (Collaborative Biomedical Products, Bedford, Mass.) and the results were expressed as concentration of compound required to inhibit IL-2 production of T cells by 50%.

T CELL PROLIFERATION ASSAY

Peripheral blood mononuclear cells (MNC) from healthy donors were separated by density centrifugation with ficoll-hypaque (LSM, Organon Teknika, Durham, N.C.). After washing the MNC with complete media (RPMI 1640 medium with 5% fetal calf serum, 100 mM glutamine, 1 mM sodium pyruvate, 0.1 mM non-essential amino acid, and 1% penn-strep, obtained from GIBCO, Grand Island, N.Y.), they were then irradiated at 7500 RADS, and resuspended at $4-4.5\times10^6$ cells/ml in complete media. Another aliquot of MNC were rosetted with neuraminidase treated SRBC. After another centrifugation with LSM, the sheep red blood cells (SRBC) of these rosetted T cells were then lysed with ammonium chloride lysing buffer (GIBCO, Grand Island, N.Y.). After washing 2× with complete media, these purified T cells were also resuspended at $2-2.5\times10^6$ cells/ml in complete media. The various dilutions of the compound were added in triplicates at 50 $\mu$l/well of a 96 well flat-bottom microculture plate (Costar, Cambridge, Mass.). T cell 37° C. in a humidified atmosphere of 5% $CO_2$-95% air for 72 hours. The proliferation of T lymphocytes was assessed by measurement of tritiated thymidine incorporation. During the last 18–24 hrs. of culturing, the cells were pulse-labeled with 2 $\mu$Ci/well of tritiated thymidine (NEN, Cambridge, Mass.). The cultures were harvested on glass fiber filters using a multiple sample harvester (MACH-II, Wallac,Gaithersburg, Md.). Radioactivity of filter discs corresponding to individual wells was measured by standard liquid scintillation counting methods (Betaplate Scint Counter, Wallac). Mean counts per minute of replicate wells were calculated and the results were expressed as concentration of compound required to inhibit tritiated thymidine uptake of T cells by 50%.

KV1.3-RUBIDIUM EFFLUX ASSAY

CHO cells transfected with $K_v1.3$ channels at site densities of approximately 40,000 sites/cell are plated into 96 well culture plates and maintained in Iscove's Modified Dulbecco's Medium (IMDM, with L-Glutamine and HEPES, JRH Biosciences). Cells are incubated overnight with $^{86}Rb^+$(3 $\mu$Ci/ml, Dupont-NEN) in the glutamine supplemented IMDM. After aspiration of the media, 100 $\mu$l of Low K Buffer (in mM, 6.5 KCl, 125 NaCl, 1 $CaCl_2$, 2 $MgCl_2$, 10 HEPES, pH adjusted to 7.2 with NaOH) is added to each well followed by 100 $\mu$l test samples in Low K Buffer also containing 0.2% BSA and 2 mM ouabain. Samples are tested at either 1 $\mu$g/ml for routine screening or at a variety of concentrations encompassing at least $\frac{1}{10}$ to 10 times the putative $IC_{50}$ of test compound to determine potency. After a fixed preincubation time, which is usually 10 min, the samples are aspirated. The $K_v1.3$ channels are opened by depolarization of the cells with High K Buffer (final concentrations, in mM, 63.25 KCl, 68.25 NaCl, 1 $CaCl_2$, 2 $MgCl_2$, 10 HEPES, pH adjusted to 7.2 with NaOH) also containing test compounds. To measure $^{86}Rb^+$ efflux through the channels, aliquots of 100 $\mu$l are taken from each well after a given time and added to plates containing 100 $\mu$l MicroScint-40 (Packard) for counting by liquid scintillation techniques. MicroScint-40 (100 $\mu$l) is then added to each well of the cell plate to determine the remaining $^{86}Rb^+$ activity. The efflux counts are normalized for the total amount of $^{86}Rb^+$ that was in the cells by adding the efflux counts to the cell plate counts. Activity is determined by % inhibition of the efflux window that is established using a saturating concentration of margatoxin (MgTX), a 39 amino acid peptide that is a potent blocker of $K_v1.3$ channels ($IC_{50}$=100 pM).

DOSAGE FORMS

As an immunosuppressive, these compounds are useful in the treatment of autoimmune diseases, the prevention of rejection of foreign organ transplants and/or related afflictions, diseases and illnesses.

The compounds of this invention can be administered for the treatment of autoimmune diseases, the prevention of rejection of foreign organ transplants and/or related afflictions, diseases and illnesses according to the invention by any means that effects contact of the active ingredient compound with the site of action in the body of a warm-blooded animal. For example, administration, can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1–500 milligrams per day. Ordinarily, from 10 to 100 milligrams per day in one or more applications is effective to obtain desired results. These dosages are the effective amounts for the treatment of autoimmune diseases, the prevention of rejection of foreign organ transplants and/or related afflictions, diseases and illnesses.

The active ingredient can be administered orally in solid dosage forms, such as capsules, tablets, troches, dragees, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention can be illustrated as follows:

CAPSULES

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

SOFT GELATIN CAPSULES

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol. The solution is made to volume with water for injection and sterilized.

SUSPENSION

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

The following examples illustrate the preparation of the compounds of Formula I and as such are not to be considered as limiting the invention set forth in the claims appended hereto. In addition, the imino and thio analogs of the following examples are intended to be included within the scope of the invention. These analogs are readily prepared from the corresponding oxepinone via methods that are well documented in the literature. Some of the $^1$H NMR spectra data for the examples hereinbelow only include select spectral peaks.

EXAMPLE 1

A Method Of Extracting The Compounds Of Formula 1(a) and 1(b) From *Spachea correa*

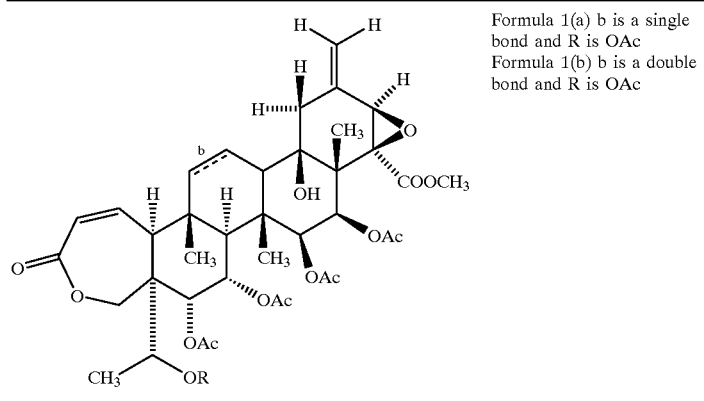

Formula 1(a) b is a single bond and R is OAc
Formula 1(b) b is a double bond and R is OAc One gram of an ethanol extract of the roots of *Spachea correa* was partitioned between 100 ml of hexane (twice) and 100 ml of 90% aqueous methanol. After separation of the phases, the defatted methanol was concentrated down under vacuum to give an aqueous suspension. This was diluted out to 100 ml with water and extracted, with 100 ml of methylene chloride.

The bioactive methylene chloride extract was dried down to give 12 mg of residue. This was first fractionated by preparative thin layer chromatography (TLC) on a 20 cm by 20 cm E. Merck silica gel 60$F_{254}$ plate of 1 mm thickness using methylene chloride-ethyl acetate 1:1 (v/v) as solvent, then by high performance liquid chromatography (HPLC) using a ZORBAX Rx$C_8$ 4.6 mm ×25 cm column, operated at 50° C. and eluted with a 50 minute gradient of acetonitrile:water (1:1, v/v) to 100% acetonitrile, delivered at 1 ml/min, to afford 4 mg of compound 1(a) and 1 mg of 1(b).

Homogeneity of the preparations was ascertained in several TLC systems, such as E. Merck silica gel 60$F_{254}$, methylene chloride-ethyl acetate 1:1, Rf 1(a) 0.4, Rf 1(b) 0.3; Whatman KC18, methanol-water 9:1, Rf 1(a) 0.65, Rf 1(b) 0.75 and by HPLC using a ZORBAX Rx$C_8$ column, acetonitrile-water 3:2, k' 1(a) 4.15, k' 1(b) 3.30; and by NMR.

Mass spectra were recorded on JEOL SX-102A (electron impact, EI,903V) and JEOL HX110 (Fast Atom Bombardment, FAB) mass spectrometers. Exact mass measurements were performed at high resolution (HR-EI) using perfluorokerosene (PFK) as the internal standard. Trimethylsilyl derivatives were prepared with a 1:1 mixture of BSTFA-pyridine at room temperature The FAB spectrum was run in a matrix of dithiothreitol (20/80).

The compound of Formula 1(a) runs underivatized by EI. The molecular ion is observed a m/z 788 and three successive loses of acetic acid are observed. The base peak is observed a m/z 334. The compound does not silylate. Scanning HR-EI indicated a molecular formula of $C_{40}H_{52}O_{16}$. A table of the critical HR-EI data is given below.

| Observed m/z | Formula | Assignment |
|---|---|---|
| 788.3220 | $C_{40}H_{52}O_{16}$ | M+ |
| 728.3040 | $C_{38}H_{48}O_{14}$ | M-acetic acid |
| 668.2834 | $C_{36}H_{44}O_{12}$ | M-2 × acetic acid |
| 334.1417 | $C_{18}H_{22}O_6$ | base peak |

$^{13}$C NMR spectra were recorded for the compound of Formula 1(a) in $CD_2Cl_2$ at 100 MHz on a Varian Unity 400 NMR spectrometer at 20° C. Chemical shifts are given in ppm relative to tetramethylsilane (TMS) at zero ppm using the solvent peak at 53.8 ppm as internal standard. The following data were observed: 15.0, 15..2, 16.8, 17.1, 20.7*, 20.9, 21.1, 21.6, 21.8, 22.2, 35.6, 40.8*, 42.1, 43.6, 45.1, 47.5, 49.3*, 53.5, 59.1, 62.6, 63.5, 66.1, 66.7*, 68.4*, 69.9, 73.9, 75.0, 75.6, 77.1*, 119.4, 123.7, 138.9, 143.0, 167.7, 169.2, 169.3*, 170.25, 170.31, 170.8, 171.3 ppm (where the * signifies the observation as broad resonances). The carbon count of 40 is in agreement with the molecular formula $C_{40}H_{52}O_{16}$ derived by scanning HR EI-MS.

The $^1$H NMR spectra of compound of Formula(a) was recorded at 400 MHz in $CD_2Cl_2$ on a Varian Unity 400 NMR spectrometer at 25° C. Chemical shifts are in ppm relative to TMS at zero ppm using the solvent peak at δ5.32 as the internal standard.

The mass spectra of the compound of Formula 1(b) was obtained as above. The following results were obtained.

| Observed m/z | Formula | Assignment |
|---|---|---|
| 786.3075 | $C_{40}H_{50}O_{16}$ | M+ |
| 726.2886 | $C_{38}H_{46}O_{14}$ | M-acetic acid |
| 666.2651 | $C_{36}H_{42}O_{12}$ | M-2 × acetic acid |
| 606.2451 | $C_{34}H_{38}O_{10}$ | M-3 × acetic acid |
| 489.2099 | $C_{26}H_{33}O_9$ | base peak |
| 471.1992 | $C_{26}H_{31}O_8$ | |

$^{13}$C NMR spectra were recorded for the compound of Formula1(b) using the procedure described above. The following results were observed: 14.8, 14.9, 17.3, 20.8, 20.9, 21.3, 21.7, 21.8, 21.9, 27.1, 35.1, 40.6, 42.3, 45.4, 48.1, 50.4, 53.5, 54.1, 57.8, 63.7, 66.2, 67.8, 68.6, 71.4, 73.3, 73.8, 74.4, 119.5, 121.1, 124.3, 137.1, 138.9, 143.3, 167.6, 168.6, 169.3, 169.5, 169.9, 171.0, 171.7 ppm.

The carbon count of 40 is in agreement with the molecular formula $C_{40}H_{50}O_{16}$ derived by scanning HR EI-MS.

EXAMPLE 2

A Method Of Extracting The Compounds Of Formula 1(c) And 1(d) From *Spachea Correa*

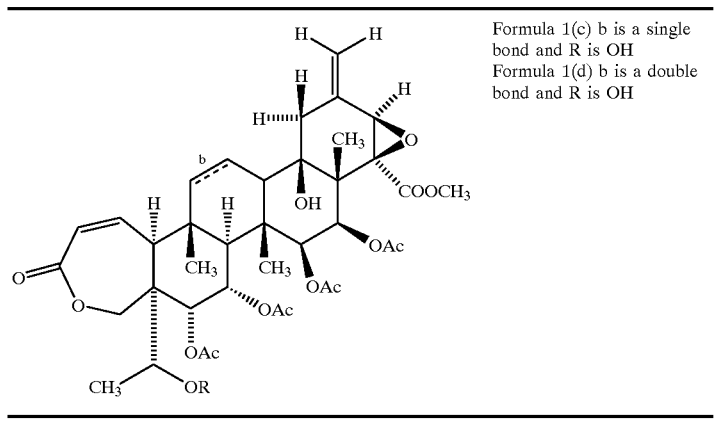

Formula 1(c) b is a single bond and R is OH
Formula 1(d) b is a double bond and R is OH Analogs of the compounds of Formula 1(a) and 1(b) could be detected in the crude extract and fractions thereof when the process of Example 1 was carried out on a larger scale. Thus, 50 g of ethanol extract were partitioned as described in Example 1 using 900 ml of each solvent at each step.

Partial purification of the methylene chloride extract was achieved by column chromatography on E. Merck silica gel 60 (120 ml), eluting with a step gradient of ethyl acetate in methylene chloride. The step gradient was designed so that the column was washed first with 100% methylene chloride and then with methylene chloride-ethyl acetate mixtures of 9:1, 8:2, 3:2, 2:1, 1:1, 1:2, 2:8 and 1:9. Ultimately the column was washed with 100% ethyl acetate. Fractions eluted with methylene chloride-ethyl acetate 3:2 were enriched in compound of Formula 1(a) and 1(b). These were resolved by HPLC using a ZORBAX $RxC_8$ 9 mm ×25 cm column, maintained at 50° C. and eluted at 4 ml/min with acetonitrile-water 1:1 v/v. Three identical runs finally afforded 1(a) and 1(b) after crystallization from methanol. Later-eluting fractions from the silica gel column above were found to contain at least two related compounds based on UV spectra and color reactions on TLC plates. Material from the methylene chloride-ethyl actate 1:1 and 1:2 washings were combined and evaporated down. Separation was achieved on the same HPLC column as above, eluting with a 50 minute gradient of 30% to 50% acetonitrile in water. Two identical runs gave purified compound 1(c). Fractions containing the compound of Formula 1(d) were again processed by HPLC (same column) using acetonitrile-water 3:7 delivered isocratically, to yield the purified compound of Formula 1(d).

The mass spectra of these compounds were recorded on a Finnigan TSQ700 mass spectrometer (electrospray ionization, ESI). The samples were analyzed by LC/MS using a 2.1 ×150 mm $C_8$ column at 0.2 ml/min. with a mobile phase of 45% acetonitrile/0.01 M aqueous ammonium acetate at 50° C. Component 1(d) had a retention time of 10.5 min. and a molecular weight of 744 which is observed a m/z: 745 (M+H), 762 (M+NH$_3$), 786 (M +H +MeCN). Component 1(c) has a retention time of 11.8 min. and a molecular weight of 746 which is observed at m/z: 747 (M+H), 764 (M+NH$_3$) and 788 (M +H +MeCN).

The $^{13}C$ NMR spectra obtained for the compound of Formula 1(c) using the conditions previously described is as follows: 15.1 (2×), 16.9, 19.8, 20.8, 20.91, 20.94, 21.9, 22.3, 35.6, 40.6, 42.2, 43.9, 45.0, 47.7, 50.8, 53.5, 55.6, 61.8, 63.5, 66.0, 67.6 (2×), 69.8, 70.0, 73.9, 75.0, 75.6, 119.3, 123.7, 139.0, 144.4, 167.8, 169.2, 169.5, 170.1, 170.4, 171.4 ppm.

The carbon count of 38 is in agreement with the molecular formula $C_{38}H_{50}O_{16}$ derived by scanning HR EI-MS.

EXAMPLE 3

Separation By HPLC

Compounds of this invention were characterized by the following behavior during HPLC separation on a ZORBAX $RxC_8$ 4.6 mm ×25 cm column, maintained at 50° C. and eluted at 1 ml/min with acetonitrile-water 3:2 v/v):
Compound 1(a): k'=4.15; 1(b): k'=3.30; 1(c): k'=2.30; 1(d): k'=2.10.

Analyses using this HPLC system can be used to quantify the compounds in the crude extract or other mixtures, by comparing the absorbance of HPLC peaks at a wavelength of 220 nm with that produced by injections of known (weighed) amounts of pure standards.

EXAMPLE 4

Additional Purification Procedure

A simplified purification process allows for rapid fractionation of even larger amounts of crude extract and the preparation of gram amounts of the compounds of Formula 1(a) and 1(b).

The ethanol extract is first dissolved at 20 grams per 150 ml in methanol. This solution is diluted with 150 ml of water and then extracted three times with methylene chloride using 150 ml of methylene chloride each time. The pooled methylene chloride extracts are evaporated down and fractionation proceeds by repeated column chromatography on silica gel. One employs methylene chloride-methanol 97:3 in a first step; the mixed compounds of Formula 1(a) and 1(b) thus obtained are resolved by chromatographing on fresh silica gel eluted with methylene chloride-ethyl acetate 3:1.

Volume of elution for the compound of Formula 1(a) ranges from about 2 to about 3.5 column volumes of solvent; that for the compound of Formula 1(b) is about 3 to about 4.5 column volumes. Finally, advantage is taken of the low solubility of these compounds, and, after total resolution by chromatography, the compounds of Formula 1(a) and 1(b) can be precipitated and or crystallized from concentrated methanol solutions.

EXAMPLE 5

4,6,7,15,16-Pentakis(acetyloxy)-21,22-epoxy-18-hydroxy-22-methoxycarbonyl-D: A-Friedo-A-homo-27,30-dinor-24-oxaoleana-1,20(29)-diene

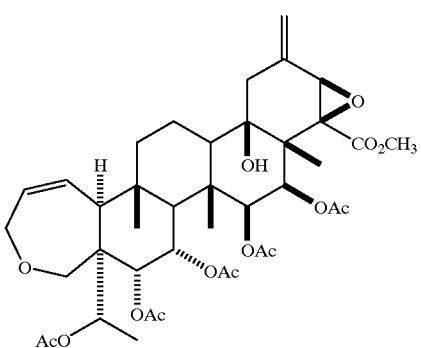

Step A: 4, 6, 7, 15,16-pentakis(acetyloxy)-21,22-epoxy-18-hydroxy-22-methoxycarbonyl-D: A-Friedo-A-homo-27,30-dinor-24-oxaoleana-1, 20(29)-dien-3-ol A solution of 3.0 g (3.8 mmole) of 4, 6,7 ,15 ,16-pentakis(acetyloxy)-21,22-epoxy-18-hydroxy-22-methoxycarbonyl-D:A-Friedo-A-homo-2 7,30-dinor-24-oxaoleana-1,20(29)-dien-3-one in 20 mL of dry dichloromethane was cooled to 0 ° C. under nitrogen. Then 9 mL of a 1 M solution of lithium tri-(tert-butoxy)aluminum hydride was added dropwise and the solution was stirred at 0 ° C. After 18 h, the reaction was quenched by dropwise addition of 20 mL of 2 M aqueous $H_2SO_4$ and the mixture was diluted with 200 mL of ether. The layers were separated and the aqueous layer was washed with two 100 mL portions of ether. The organic layers were sequentially washed with 20 mL of 2 M aqueous $H_2SO_4$ and brine, then were combined, dried over $MgSO_4$, and concentrated to afford the title compound, which was used directly in the next step.

Step B: 4, 6, 7, 15, 16-Pentakis(acetyloxy)-21,22-epoxy-18-hydroxy-22-methoxycarbonyl-D: A-Friedo-A-homo-27,30-dinor-24-oxaoleana-1,20(29)-diene A sample of 2.9 g of crude 4, 6, 7, 15, 16-pentakis(acetyloxy)-21, 22-epoxy-18-hydroxy-22-methoxycarbonyl-D:A-Friedo-A-homo-27,30-dinor-2 4-oxaoleana-1,20(29)-dien-3-ol was dissolved in 10 mL of dry dichloromethane under nitrogen. To this was added 10 mL of triethylsilane, and the solution was stirred at room temperature for 10 min. Then 2 mL (20 mmole) of boron trifluoride etherate was added and the mixture was stirred at room temperature for 15 min. The reaction was quenched by addition of 10 mL of saturated aqueous $KHCO_3$ solution and the resulting mixture was partitioned between ether and water. The water layer was washed with ether and the organic extracts were washed with brine, then were combined, dried over $MgSO_4$, and concentrated. The residue was purified by chromatography on silica gel using 30% ethyl acetate-hexane to afford the title compound as a white solid.

$^1H$ NMR ($CDCl_3$) δ4.14, 4.34 (dd, AB, 2H, J =12 Hz, $C_3$-H); Mass Spectrum (APCI) m/e 792 ($M^+NH_4$).

EXAMPLE 6

4, 6, 7, 15, 16-Pentakis(acetyloxy)-3-(2-propenyl)-21,22-epoxy-18-hydroxy-2 2-methoxycarbonyl-D:A-Friedo-A-homo-27,30-dinor-24-oxaoleana-1, 20(29)-diene

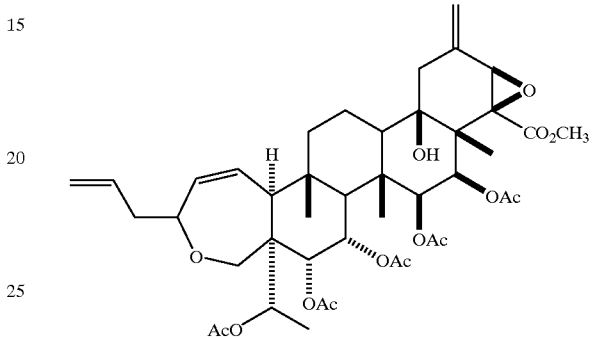

A solution of 1.0 mL of Red-Al [sodium bis(2-methoxyethoxy) aluminum hydride, 65% in toluene] was diluted with 5 mL of dry toluene and cooled to 0° C. under nitrogen. Then 200 µL of ethanol was added and the mixture was stirred at 0° C. for 1 h. A 3.0 mL aliquot of this solution was added th a solution of 500 mg (0.63 mmole) of 4, 6, 7, 15, 16-pentakis(acetyloxy)-21,22-epoxy-18-hydroxy-22-methoxycarbonyl-D: A-Friedo-A-homo-27,30-dinor-24-oxaoleana-1,20(29)-dien-3 -one in 15 mL of dry toluene that had been cooled to 0° C. under nitrogen. After 3 h, the reaction was diluted with 20 mL of dichloromethane and quenched with 20 mL of 1.OM aqueous HCl. The layers were separated and the organic layer was washed with brine and dried over $MgSO_4$. The solvent was concentrated and the residue was dissolved in 10 mL of dry dichloromethane. To 5 mL of this solution was added 0.5 mL (3.14 mmole) of allyltrimethylsilane a the solution was cooled to 0° C. under nitrogen. Then 0.4 mL of boron trifluoride-etherate was added and the solution was stirred at 0° C. After 1 h, the reaction was diluted with 20 mL dichloromethane, washed with saturated aqueous $NaHCO_3$ solution and brine, and dried over $Na_2SO_4$. The solvent was concentrated and the residue was purified by HPLC (Waters RCM, µ Porosil, 25 mm ×20 cm) using a mixture of 8:4:1 hexane-methyl tert-butyl ether-acetonitrile:hexane to afford the 3α-isomer as a white solid.

$^1H$ NMR ($CDCl_3$) δ3.4, 3.8 (dd, AB, 2H, J =12.1 Hz, C24—$CH_2$)3.9 (s, 3H, $OCH_3$), 5.08 (m, 2H, CH=$CH_2$), 5.2 (s, 1H, C29—H), 5.5 (s, 1H, C29—H), 5.8 (m,1H,$CH_2C$ $H$=$CH_2$); $^{13}C$ NMR ($CDCl_3$) δ116.9, 118.8, 125.7, 131.3, 134.6, 138.5; Mass Spectrum (APCI): m/e 832 ($M^+NH_4$). Further elution of the column afforded the 3β-isomer as a white solid.

1H NMR ($CDCl_3$) δ3.4, 3.8 (dd, AB, 2H, J =12.2 Hz, C24=$CH_2$) 3.9 (s, 3H, $OCH_3$), 5.11(m, 2H, CH=$CH_2$), 5.25 (s, 1H, C29-H), 5.55 (s, 1H, C29—H), 5.84 (m, 1H,$CH_2CH$=$CH_2$); $^{13}C$ NMR ($CDCl_3$) δ117.0, 118.9, 126.1, 131.8, 135.0, 138.2; Mass Spectrum (APCI): m/e 832 ($M^+NH_4$).

EXAMPLE 7

4, 6, 7, 15, 16-Pentakis(acetyloxy)-21,22-epoxy-18-hydroxy-22-methoxycarbonyl-D: A-Friedo-A-homo-27,30-dinor-24-oxaoleana-1-en-3, 20-dione

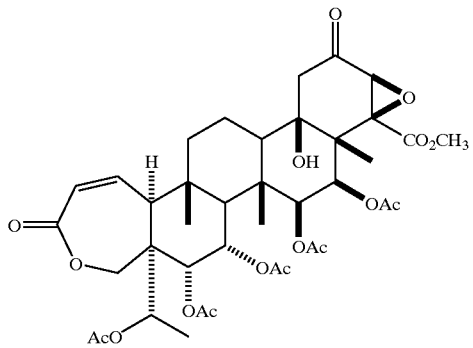

A solution of 13.7 mg of 4, 6, 7, 15, 16-Pentakis (acetyloxy)-21, 22-epoxy-18-hydroxy-22-methoxycarbonyl-D:A-Friedo-A-homo-27,30-dinor-24-oxaoleana-1,20(29)-dien-3-one in 12 ml of (1:1, $CH_2Cl_2/CH_3OH$) was cooled to −78 °C. and $O_3$ was bubbled into the solution until it contained a blue color. The solution was then purged with nitrogen for 3 minutes and 3 drops of $Me_2S$ was added. The solution was allowed to warm to 25° C. for 14 hours. Volitiles were removed by vacuum and the residue was purified by chromatography on silica gel using 25% ethyl acetate-hexane to afford the title compound as a white solid.
$^1$H NMR ($CDCl_3$) δ2.83 (d, 1H, J =14 Hz), 2.39 (d, 1H, J=14 Hz); Mass Spectrum (EI) m/e 813 (M+Na).

EXAMPLE 8

4,6,7,15,16-Pentakis(acetyloxy)-18-hydroxy-20-oxo-21,22-epoxy-22-methoxycarbonyl-D: A-Friedo-A-homo-27,30-dinor-24-oxaoleana-1-ene

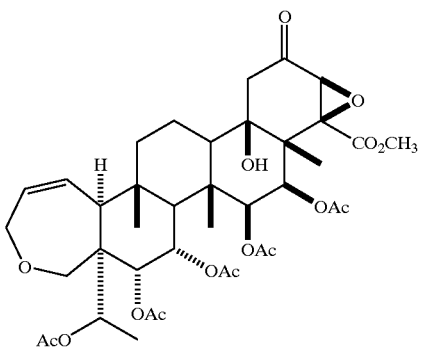

To a solution of 2.5 g (2.77 mmole) of 4,6,7,15,16-Pentakis (acetyloxy)-21,22-epoxy-18 -hydroxy-22-methoxycarbonyl-D:A-Friedo-A-homo-27,30-dinor-24-oxaoleana-1, 20(29)-diene in 150 mL THF was added 0.82 g (7 mmole) N-methyl morpholine N-oxide and 37 mg (0.15 mmole) of osmium tetroxide. The solution was stirred at ambient temperature for 24 h, then treated with an additional 37 mg (0.15 mmole) of osmium tetroxide and stirred at ambient temp for 14 hours. The reaction mixture was then treated with a solution of 1.7 g (8 mmole) of sodium periodate in 50 ml water and allowed to stir 24 hrs. Concentrated under reduced pressure and partitioned between 300 ml ether and 100 ml water. The layers were separated and dryed over $NaSO_4$ and evaporated. The residue was first filtered through a plug of silica gel and then purified by flash chromatograpy on silica gel with 10–25% acetone hexane to give the title compound as a white solid.
$^1$H NMR ($CDCl_3$) 3.66 (d, 1H, J =12.1 Hz), 3.63 (d, 1H, J=12.1 Hz), 2.82 (d, 1H, J =14.4 Hz), 2.40 (d, 1H, J=14.4 Hz); Mass Spectrum (CI, $NH_4OAc$): m/e 794 M+$NH_4$).

EXAMPLE 9

[5-S-5aα,5aα,7aα,11β,11aβ,11bα,12α,13α,13aα]-13a-(1-R-acetoxyethyl)-8-oxo-11,12,13-triacetoxy-5b,9,11a-trimethyl-1, 3,5a,5b,6,7,7a,8,11,11a,11b,12,13,13a,tetradecahydrophenanthro[2,1-c]oxepin

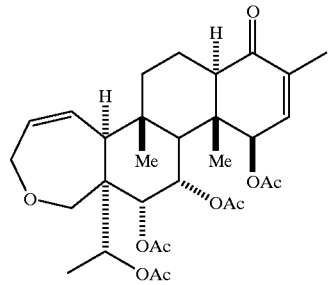

To a solution of 1.0 g (1.1 mmole) of 4,6,7,15,16-Pentakis (acetyloxy)-18-hydroxy-20-oxo-21,22-epoxy-22-methoxycarbonyl-D: A-Friedo-A-homo-27,30-dinor-24-oxaoleana-1-ene in 16 mL DMF was added 410 mg (10 mmole) of LiCl . The solution was stirred at 120° for 2.5 hours and allowed to cool. The reaction was partitioned between 200 ml ether and 100 ml water and separated. The aqueous was washed twice with 100 ml ether and the organic layers were combined and washed with brine and dryed over $MgSO_4$ and evaporated. The residue was then purified by flash chromatograpy on silica gel with 10% acetone hexane to give the title compound as a white solid.
$^1$H NMR ($CDCl_3$) δ6.06 (s, 1 H), 4.31 (d, 1 H, J =17 Hz), 4.11 (d, 1 H, J =17 Hz), 2.21 (dd, 1H, J =12, 3.2 Hz), 1.71 (s, 3 H); Mass Spectrum (CI, $NH_4OAc$): m/e 592 (M+$NH_4$)

EXAMPLE 10

[5-S-5aα,5aα,7aα,11β,11bα,12α,13α,13aα]-13a-(1-R-acetoxyethyl)-8-oxo-11,12,13-triacetoxy-5b,9,11a-trimethyl-1, 3,5a,5b,6,7,7a,8,11,11a,11b,12,13,13a, tetradecahydrophenanthro[2,1-c]oxepin-3-one

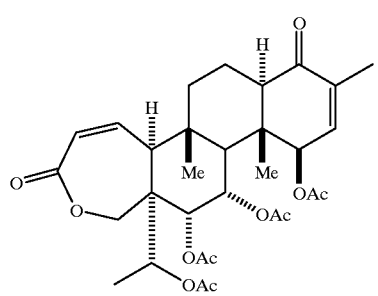

A solution of 4,6,7,15,16-Pentakis(acetyloxy)-21,22-epoxy-18 -hydroxy-22-methoxycarbonyl-D:A-Friedo-A- homo-27,30-dinor-24-oxaoleana-1-en-3,20-dione (115 mg, 0.15 mmol) and LiCl (61.7 mg, 1.5 mmol) in 5 ml of DMSO was heated to 125° C. for 6 h. The brown solution was poured into ether and was washed with brine twice. The organic layer was dried over MgSO₄ and was filtered through silica gel. The residue was purified by HPLC (Waters RCM, 25 mm ×10 cm) using a mixture of 3.6 :8 (5:4:1 hexane/methyl tert-butyl ether/acetonitrile:hexane) to afford the title compound.

¹H NMR (CDCl₃) δ6.40 (dd, 1H, J =12.1, 8.9 Hz), 2.27 (dd, 1H, J =12.1, 3.4 Hz), 1.76 (s, 3H); Mass Spectrum (CI, NH₄OAc): m/e 606 (M+NH₄)

EXAMPLE 11

[5-S-5aα,5aα,7aα,8α,8β,11β,11 aβ,11bα,12α,13α, 13aα]-13a-(1-R-acetoxyethyl)-8-hydroxy-8-(2-(2-ethoxyphenyl)ethyl)-11,12,13-triacetoxy-5b,9,11a-trimethyl-1,3,5a,5b,6,7,7a,8,11,11a,11b,12,13,13a-tetradecahydrophenanthro [2,1-c]oxepin

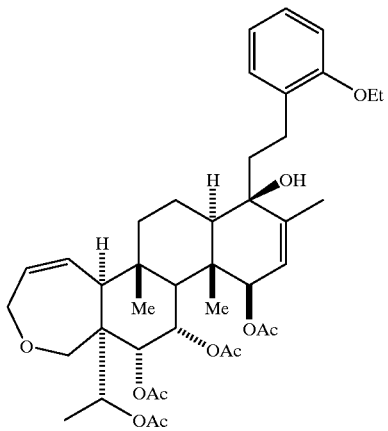

Step A: Preparation of ethoxyphenethyl bromide

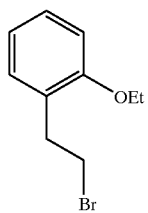

To a suspension of 1.00 g (7.24 mmol) of 2-hydroxyphenethyl alcohol and 1.35 g (8.68 mmol) of potassium carbonate in 15 ml of N,N-dimethylformamide was added 2.00 g (14.48 mmol) of iodoethane at 0° C. The reaction mixture was stirred at 40–45° C. for 12 h and was poured into 200 ml of ether. It was washed with water (20 ml ×3), dried over MgSO₄ and concentrated. The residue was purified by silica gel chromatography with 9:1 hexane/ethyl acetate to afford the 2-ethoxyphenethyl alcohol as a colorless oil.

To a solution of 1.35 g (8.12 mmol) of 2-ethoxyphenethyl alcohol and 2.05 g (20.03 mmol) of triethylamine in 15 ml of dichloromethane was slowly added 1.86 g (16.24 mmol) of methanesulfonyl chloride at 0° C. The reaction mixture was stirred at 0° C. for 2 h and was poured into 200 ml of mixed solution of hexaneether(1:1). It was washed with 30 ml of water, dried over MgSO₄, filtered through a plug of silica gel and concentrated. The residue was dissolved in 30 ml of acetone and 2.82 g (32.48 mmol) of lithium bromide was added slowly at 0° C. The reaction mixture was refluxed for 5 h and volatiles were removed. The residue was added 150 ml of ether, washed with water (30 ml ×2), dried over MgSO₄, filtered through a plug of silica gel and concentrated to give 2-ethoxyphenethyl bromide as a colorless oil.

Step B: Preparation of [5-S-5aα,5aα,7aα,8α,8β,-1 β,11aβ,11bα,12α,13α,13aα]-13a-(1-R-acetoxyethyl)-8 -hydroxy-8-(2-(2-ethoxyphenyl) ethyl)-11,12,13-triacetoxy-5b,9,11a-trimethyl-1,3,5a, 5b,6,7,7a,8,11, 11a,11b,12,13,13a-tetradecahydrophenanthro[2,1-c]oxepin

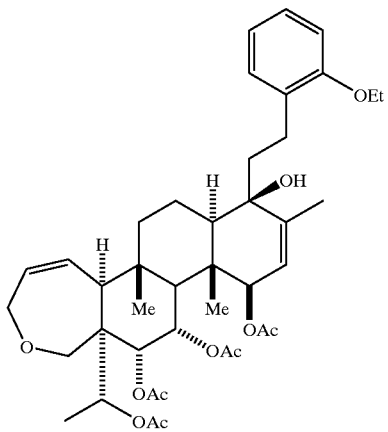

A solution of Grignard reagent (2-ethoxyphenethyl magnesium bromide, 0.4 M in THF) was prepared in the following way: 1.30 g (5.68 mmol) of 2-ethoxyphenethyl bromide was added to the mixture of 207 mg (8.5 mmol) of magnesium in 14 ml of anhydrous tetrahydrofuran at room temperature under N₂ and It was heated at reflux for 1 h.

To a solution of 20 mg (0.0348 mmol) of [5-S-5aα, 5aα,7aα,11β,11aβ,11bα,12α,13α,13aα]-13a(1-R-acetoxyethyl)-8-oxo-11,12,13-triacetoxy-5b,9,11a-trimethyl-1,3,5a,5b,6,7,7a,8,11, 11a,11b,12,13,13a-tetradecahydrophenanthro[2,1-c]oxepin in 2 ml of tetrahydrofuran was added 0.53 ml (0.21 mmol) of phenethyl magnesium bromide in THF (0.4 M). The mixture was stirred at room temperature under N₂ for 2 h. Then it was quenched with 5 drops of 0.1 M phosphate buffer(pH =7). The residue was filtered through a plug of silica gel and was purified by HPLC (waters RCM,μ porosil 10 mm ×10 cm) using a mixture of 3.6:8 (5:4:1 hexane/methyl tert-butyl ether/acetonitrile:hexane) to afford the title compound as a white solid. ¹H NMR (CDCl₃) δ1.43 (t, 3H, J =7 Hz), 1.80 (s,3H), 4.05 (q, 2H, J =7 Hz), 7.09–7.11 (m, 2H), 7.13–7.15 (m, 2H); Mass Spectrum (CI, NH₄OAc): m/e 742(M+NH₄)

By the procedures described in Example 11, the following examples 12–61 were prepared.

EXAMPLE 12

[5-S-5aα,5aα,7aα,8α,8β,11aβ,11bα,12α, 13α, 13aα]-13a-(1-R-acetoxyethyl)-8-hydroxy-8-(2-(2-n-butyloxyphenyl)ethyl)-11,12,13-triacetoxy-5b,9,11a-trimethyl-1,3,5a,5b,6,7,7a,8,11,11a,11b,12,13,13a-tetradecahydrophenanthro [2,1-c]oxepin

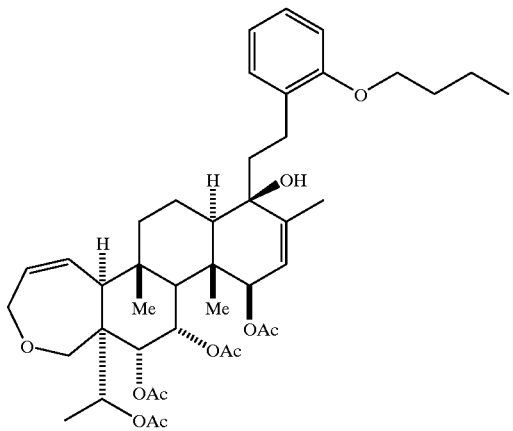

$^1$H NMR (CDCl$_3$) δ1.00 (t, 3H, J =7 Hz), 1.52 (m,2H), 1.76 (m,2H), 1.81 (s,3H), 3.98 (q, 2H, J =6 Hz), 6.82–6.88 (m, 2H), 7.08–7.17 (m, 2H); Mass Spectrum (CI, NH$_4$OAc): m/e 771(M+NH$_4$)

EXAMPLE 13

[5-S-5aα,5aα,7aα,8α,8β,11β,11aβ,11bα,12α,13α,13aα]-13a-(1-R-acetoxyethyl)-8-hydroxy-8-(2-(2-allyloxyphenyl)ethyl)-11,12,13-triacetoxy-5b,9,11a-trimethyl-1,3,5a,5b,6,7,7a,8,11,11a,11b,12,13,13a-tetradecahydrophenanthro [2,1-c]oxepin

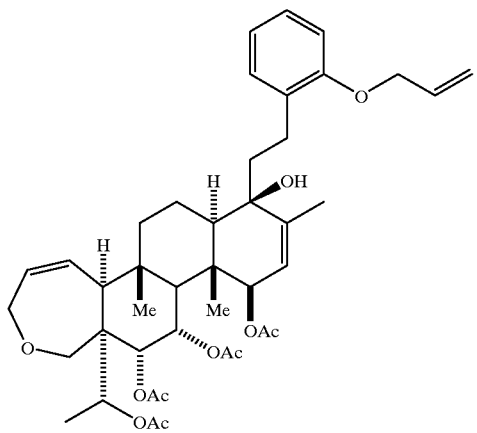

$^1$H NMR (CDCl$_3$) δ1.80 (s,3H), 4.56 (m, 2H), 5.32 (d, 1H, J =21 Hz), 5.42 (d, 1H, J =23 Hz), 6.07 (m, 1H), 6.83–6.90 (m, 2H), 7.10–7.16 (m, 2H); Mass Spectrum (CI, NH$_4$OAc): m/e 754 (M+NH$_4$)

EXAMPLE 14

[5-S-5aα,5aα,7aα,8α,8β,11β,11aβ,11bα,12α,13α,13aα]-13a-(1-R-acetoxyethyl)-8-hydroxy-8-(2-(2-benzyloxyphenyl)ethyl)-11,12,13-triacetoxy-5 b,9,11a-trimethyl-1,3,5a,5b,6,7,7a,8,11,11a,11b,12,13,13a-tetradecahydrophenanthro [2,1-c]oxepin

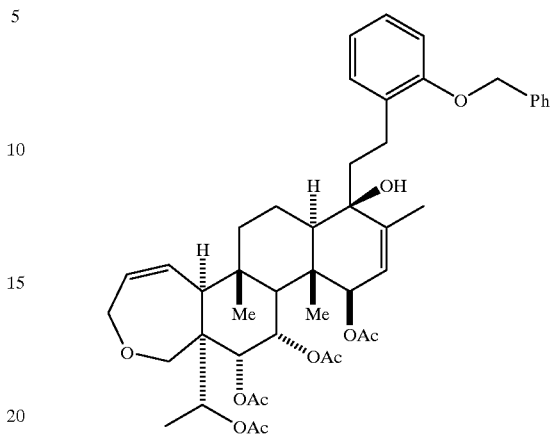

$^1$H NMR (CDCl$_3$) δ1.68 (s,3H), 5.08 (s, 2H), 6.90–6.93 (m, 2H), 7.12–7.19 (m, 2H), 7.28–7.45 (m, 5H); Mass Spectrum (CI, NH$_4$OAc): m/e 805(M+NH$_4$)

EXAMPLE 15

[5-S-5aα,5aα,7aα,8α,8β,11β,11aβ,11bα,12α,13α,13aα]-13a-(1-R-acetoxyethyl)-8-hydroxy-8-phenyl-11,12,13-triacetoxy-5b,9,11a-trimethyl-1, 3,5a,5b,6,7,7a,8,11,11a,11b,12,13,13a-tetradecahydrophenanthro [2,1-c]oxepin

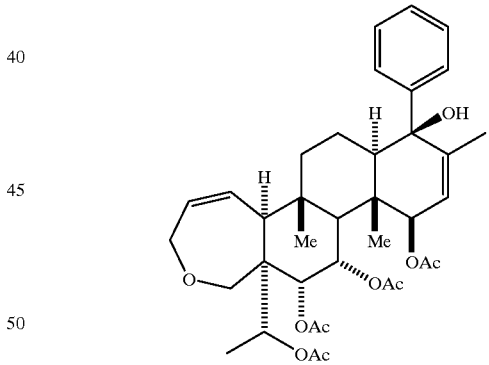

$^1$H NMR δ7.32 (t, 2H, J=7.5 Hz), 7.23 (t, 1H, J=7.3 Hz), 5.30 (s, 1H), 5.27 (s, 1H); Mass Spectrum (APCI): m/e 670 (M+NH$_4$)

EXAMPLE 16

[5-S-5aα,5aα,7aα,8α,8β,11β,11bα,12α,13α,13aα]-13a-(1-R-acetoxyethyl)-8-hydroxy-8-benzyl-11,12,13-triacetoxy-5b,9,11a-trimethyl-1, 3,5a,5b,6,7,7a,8,11,11a,11b,12,13,13a-tetradecahydrophenanthro[2,1-c]oxepin

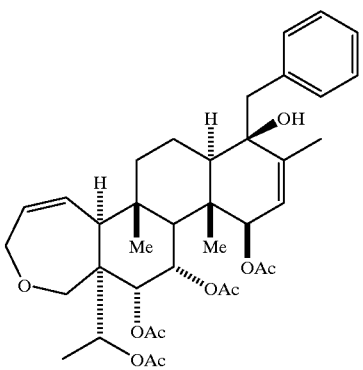

¹H NMR δ7.33 (t, 2H, J =8.0 Hz), 7.29 (t, 1H, J =6.9 Hz), 7.10 (d, 2H, J =7.6 Hz), 5.17 (s, 1H), 4.76 (s, 1H), 3.11 (d, 1H, J=14.5 Hz), 2.87 (d, 1H, J=14.5 Hz); Mass Spectrum (APCI): m/e 684 (M+NH$_4$)

EXAMPLE 17

[5-S-5aα,5aα,7aα,10α,11β,11aβ,11bα,12α,13α,13aα]-13a-(1-R-acetoxyethyl)-8-oxo-10-benzyl-11,12,13-triacetoxy-5b,9,11a-trimethyl-1, 3,5a,5b,6,7,7a,8,9,10,11,11a,11b,12,13,13a-hexadecahydrophenanthro [2,1-c]oxepin

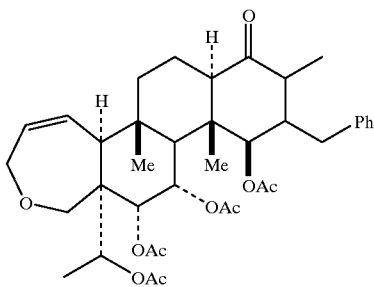

The title compound was isolated in the preparation of Example 16.

¹H NMR δ7.38 (t, 2H, J =7.8 Hz), 7.27 (d, 2H, J =7.8 Hz), 7.24 (t, 1H, J =7.8 Hz), 5.05 (s, 1H), 2.72–2.83 (m, 3H), 1.19 (d, 3H, J =6.4 Hz), 1.09 (d, 3H, J =6.9 Hz); Mass Spectrum (APCI): m/e 684 (M+NH$_4$)

EXAMPLE 18

[5-S-5aa,5aa,7aa,8a,8b,11b,11ab,11ba,12a,13a,13aa]-13a-(1-R-acetoxyethyl)-8-hydroxy-8-(2-phenylethyl)-11,12,13-triacetoxy-5b,9,11a-trimethyl-1,3,5a,5b,6,7,7a,8,11,11a,11b,12,13,13a-tetradecahydrophenanthro [2, 1-c]oxepin

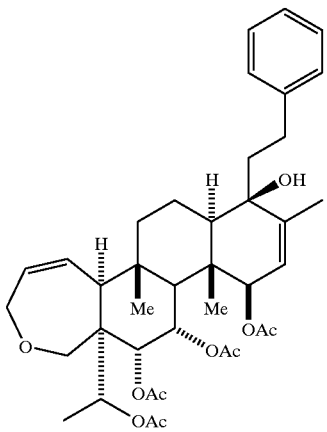

To a solution of [5-S-5aα,5aα,7aα,11β,11aβ,11bα,12α,13α,13aα]-13a-(1-R-acetoxyethyl)-8-oxo-11,12,13-triacetoxy-5b,9,11a-trimethyl-1, 3,5a,5b,6,7,7a,8,11,11a,11b,12,13,13a, tetradecahydrophenanthro [2,1-c]oxepin (25.2 mg, 0.043 mmol) in 2.0 ml of THF at 0° C. was added phenethyl magnesium bromide (0.35 ml, 1.0 M in THF). After 5 min, the solution was warmed to rt for 2 h and was quenched with 3 drops of 0.1 M of phosphate buffer (pH =7). The mixture was filtered through a plug of silica gel and was purified by HPLC (Waters RCM, 25 mm ×10 cm) using a mixture of 3.6:8 (5:4:1 hexane/methyl tert-butyl ether/acetonitrile:hexane) to afford the title compound. ¹H NMR δ7.29 (t, 2 H, J =7.6 Hz), 7.17–7.21 (m, 3 H), 5.22 (s, 1H), 5.08 (s, 1H), 2.38–2.45 (m, 1H), 2.27–2.33 (m, 1 H), 1.78 (s, 3H); Mass Spectrum (APCI): m/e 698 (M+NH$_4$).

EXAMPLE 19

[5-S-5aα,5aα,7aα,8α,8β,11β,11aβ,11b α,12α,13α,13aα]-13a-(1-R-acetoxyethyl)-8-hydroxy-8-(3-phenylpropyl)-11,12,13-triacetoxy-5b,9,11a-trimethyl-1, 3,5a,5b,6,7,7a,8,11,11a,11b,12,13,13a-tetradecahydrophenanthro [2.1-c]oxepin

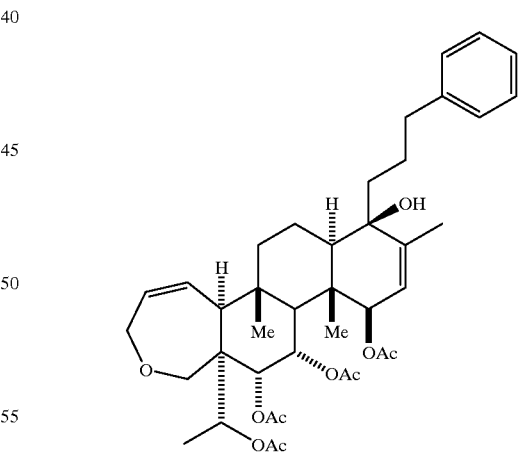

¹H NMR δ7.28 (t, 2 H, J =8.0 Hz), 7.16–7.19 (m, 3H), 5.00 (s, 1 H), 5.11 (s, 1 H), 2.54–2.65 (m, 2 H), 1.57 (s, 3 H); Mass Spectrum (APCI): m/e 712 M+NH$_4$)

EXAMPLE 20

[5-S-5aα,5aα,7aα,8α,8β,11β,11aβ,11bα,12α,13α,13aα]-13a-(1-R-acetoxyethyl)-8-hydroxy-8-(3-phenylpropyl)-11,12-diacetoxy-13-hydroxy-5b,9,11a-trimethyl-1,3,5a,5b,6,7,7a,8,11,11a,11b,12,13,13a-tetradecahydrophenanthro [2,1-c]oxepin

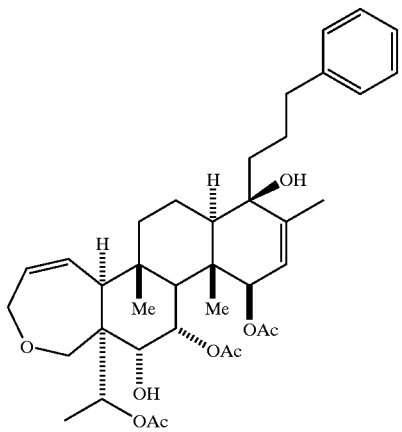

The title compound was isolated in the reaction that produced Example 19. $^1$H NMR $\delta$7.30 (t, 2 H, J =8.0 Hz), 5.05 (s, 1 H), 5.15 (s, 1 H), 4.65 (dd, 1H, J =3.9, 1.9 Hz), 2.55–2.66 (m, 2 H), 1.59 (s, 3H); Mass Spectrum (APCI): m/e 670 (M+NH$_4$)

EXAMPLE 21

[5-S-5a$\alpha$,5a$\alpha$,7a$\alpha$,8$\alpha$,8$\beta$,11$\beta$,11a$\beta$,11b$\alpha$,12$\alpha$,13$\alpha$,13a$\alpha$]-13a-(1-R-acetoxyethyl)-8-hydroxy-8-(4-phenylbutyl)-11,12, 13-triacetoxy-5b,9,11a-trimethyl-1, 3,5a,5b,6,7,7a,8,11, 11a,11b,12,13,13a-tetradecahydrophenanthro [2 1-c]oxepin

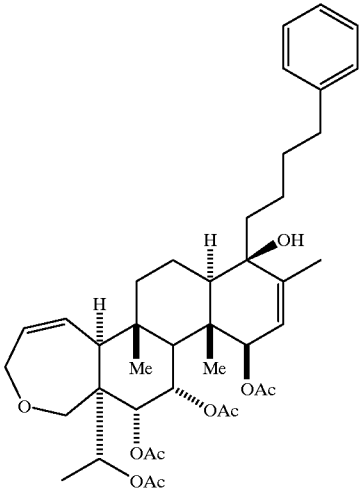

$^1$H NMR $\delta$7.29 (t, 2H, J=8.3 Hz), 7.18–7.21 (m, 3H), 5.13 (s, 1H), 5.13 (s, 1H), 2.63–2.66 (m, 2H), 1.68 (s, 3H); Mass Spectrum (APCI): m/e 726 (M+NH$_4$)

EXAMPLE 22

[5-S-5a$\alpha$,5a$\alpha$,7a$\alpha$,8$\alpha$,8$\beta$,11$\beta$,11a$\beta$,11b$\alpha$,12$\alpha$,13$\alpha$,13a$\alpha$]-13a-(1-R-acetoxyethyl)-8-hydroxy-8-(2-trimethylsilylacetylenyl)-11,12,13-triacetoxy-5b,9,11a-trimethyl-1,3,5a,5b,6,7,7a,8,11,11a,11b,12,13,13a-tetradecahydrophenanthro [2, 1-c]oxepin

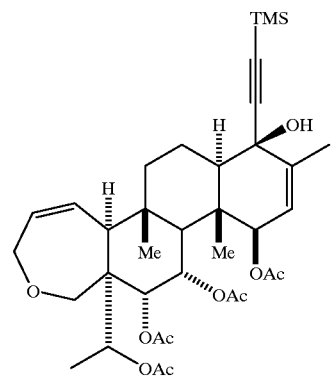

$^1$H NMR (CDCl$_3$) $\delta$5.16 (s, 1H), 5.11 (s, 1H), 1.89 (s, 3H), .017 (s, 9H); Mass Spectrum (APCI): m/e 690 (M+NH$_4$)

EXAMPLE 23

[5-S-5a$\alpha$,5a$\alpha$,7a$\alpha$,8$\alpha$,8$\beta$,11$\beta$,11a$\beta$,11b$\alpha$,12$\alpha$,13$\alpha$,13a$\alpha$]-13a-(1-R-acetoxyethyl)-8-hydroxy-8-(acetylenyl)-11,12,13-triacetoxy-5b,9,11a-trimethyl-1, 3,5a,5b,6,7,7a,8,11,11a, 11b,12,13,13a-tetradecahydrophenanthro [2,1-c]oxepin

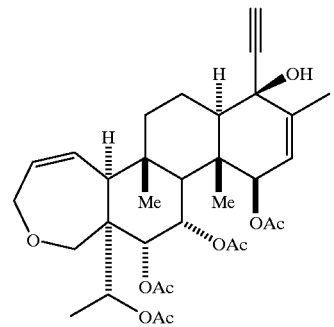

$^1$H NMR (CDCl$_3$) $\delta$5.15 (s, 1H), 5.09 (s, 1H), 2.41 (s, 1H), 1.89 (s, 3H) Mass Spectrum (APCI): m/e 618 (M+NH$_4$)

EXAMPLE 24

[5-S-5a$\alpha$,5a$\alpha$,7a$\alpha$,8$\alpha$,8$\beta$,11$\beta$,11a$\beta$,11b$\alpha$,12$\alpha$,13$\alpha$,13a$\alpha$]-13a-(1-R-acetoxyethyl)-8-hydroxy-8-(phenylacetylenyl)-11,12,13-triacetoxy-5b,9,11a-trimethyl-1, 3,5a,5b,6,7,7a,8, 11,11a,11b,12,13,13a-tetradecahydrophenanthro [2,1-c] oxepin

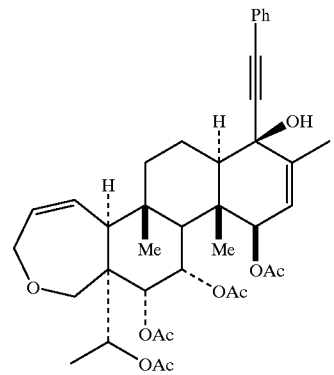

$^1$H NMR (CDCl$_3$)$\delta$7.30–7.44 (m, 5H), 4.69 (s, 1H), 3.78 (s, 1H) Mass Spectrum (APCI): m/e 694 (M+NH$_4$)

EXAMPLE 25

[5-S-5aα,5aα,7aα,8α,8β,11β,11aβ,11bα,12α,13α,13aα]-13a-(1-R-acetoxyethyl)-8-hydroxy-8-(but-3-en-1-yl)-11,12,13-triacetoxy-5b,9,11a-trimethyl-1, 3,5a,5b,6,7,7a,8,11,11a,11b,12,13,13a-tetradecahydrophenanthro [2,1-c]oxepin

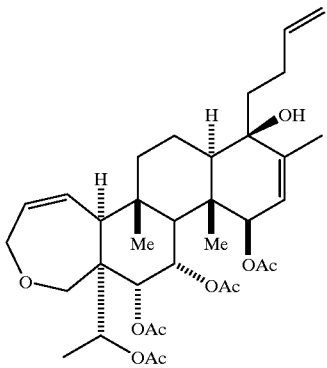

$^1$H NMR(CDCl$_3$) δ5.74–5.79 (m, 2H), 5.14 (s, 1H), 5.03 (d, 1H, J=16.8 Hz), 5.02 (s, 1H), 4.95 (d, 1H J =10.0 Hz), 0.69 (s, 3H); Mass Spectrum (APCI): m/e 648 (M+NH$_4$)

EXAMPLE 26

[5-S-5a α,5aα,7aα,8α,8β,11β,11aβ,11bα,12α,13α,13aα]-13a-(1-R-acetoxyethyl)-8-hydroxy-8-(4,4-dimethylbut-3-en-1-yl)-11,12,13-triacetoxy-5b,9,11a-trimethyl-1, 3,5a,5b,6,7,7a,8,11,11a,11b,12,13,13a-tetradecahydrophenanthro [2, 1-c]oxepin

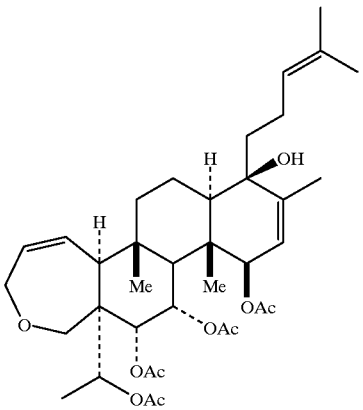

$^1$H NMR (CDCl$_3$) δ5.15 (s, 1H), 5.03 (bs, 2H), 1.70 (s, 3H), 1.68 (s, 3H), 1.62 (s, 3H); Mass Spectrum (APCI): m/e 676 (M+NH$_4$)

EXAMPLE 27

[5-S-5aα,5aα,7aα,8α,8β,11β,11aβ,11bα,12α,13α,13aα]-13a-(1-R-acetoxyethyl)-8-hydroxy-8-(2-(2-fluorophenyl)ethyl)-11,12,13-triacetoxy-5b,9,11a-trimethyl-1,3,5a,5b,6,7,7a,8,11,11a,11b,12,13,13a-tetradecahydrophenanthro [2,1-c]oxepin

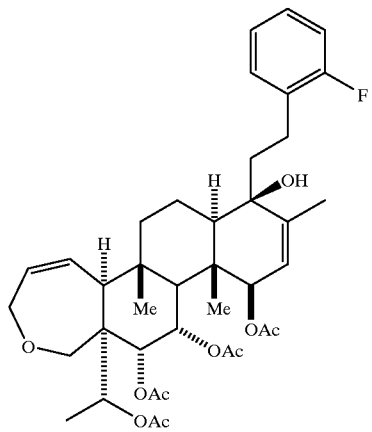

$^1$H NMR (CDCl$_3$) δ1.79 (s,3H), 7.00–7.07 (m, 2H), 7.14–7.18 (m, 2H); Mass Spectrum (CI, NH$_4$OAc): m/e 716 (M+NH$_4$)

EXAMPLE 28

[5-S-5aα,5aα,7aα,8α,8β,11β,11aβ,11bα,12α,13α,13aα]-13a-(1-R-acetoxyethyl)-8-hydroxy-8-(2-(2,6-difluorophenyl)ethyl)- 11,12,13-triacetoxy-5b,9,11a-trimethyl-1,3,5a,5b,6,7,7a,8,11,11a,11b,12,13,13a-5 tetradecahydrophenanthro[2,1-c]oxepin

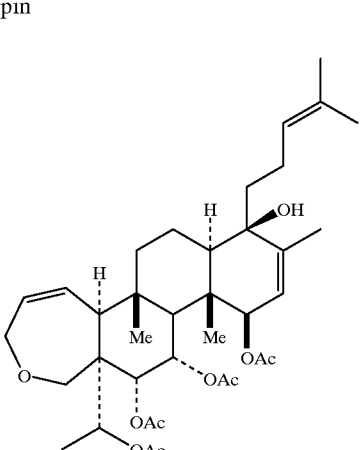

$^1$H NMR (CDCl$_3$)δ1.80 (s,3H), 6.82–6.85 (m, 2H), 7.11–7.13 (m, 2H); Mass Spectrum (CI, NH$_4$OAc): m/e 734 (M+NH$_4$)

EXAMPLE 29

[5-S-5aα,5aα,7aα,8α,8β,11β,11aβ,11bα,12α,13α,13aα]-13a-(1-R-acetoxyethyl)-8-hydroxy-8-(2-(2-chlorophenyl)ethyl)-11,12,13-triacetoxy-5b,9,11a-trimethyl-1,3,5a,5b,6,7,7a,8, 11,11a,11b,12,13,13a-tetradecahydrophenanthro [2,1-c] oxepin

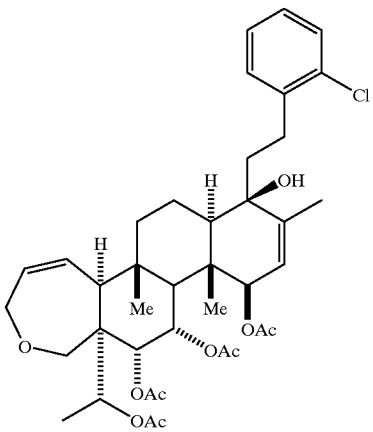

¹H NMR δ7.33 (d, 1H, J =7.6 Hz), 7.13–7.21 (m, 3 H), 5.22 (s, 1H), 5.08 (s, 1H), 2.54–2.60 (m, 1H), 2.29–2.35 (m, 1H), 1.81 (s, 3H); Mass Spectrum (APCI): m/e 732 (M+NH₄)

EXAMPLE 30

[5-S-5aα,5aα,7aα,8α,8β,11β,11aβ,11bα,12α,13α,13aα]-13a-(1-R-acetoxyethyl)-8-hydroxy-8-(2-(3-chlorophenyl)ethyl)-11,12,13-triacetoxy-5 b,9,11a-trimethyl-1,3,5a,5b,6,7,7a,8,11,11a,11b,12,13,13a-tetradecahydrophenanthro [2,1-c]oxepin

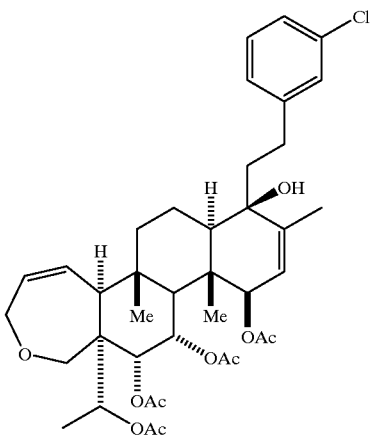

¹H NMR (CDCl₃) δ1.76 (s,3H), 7.03–7.05 (m, 1H), 7.16–7.20 (m, 3H); Mass Spectrum (CI, NH₄OAc): m/e 732(M+NH₄)

EXAMPLE 31

[5-S-5aα,5aα,7aα,8α,8β,11β,11aβ,11bα,12α,13α,13aα]-13a-(1-R-acetoxyethyl)-8-hydroxy-8-(2-(4-chlorophenyl)ethyl)-11,12,13-triacetoxy-5b,9,11a-trimethyl-1,3,5a,5b,6,7,7a,8,11,11a,11b,12,13,13a-tetradecahydrophenanthro [2,1-c]oxepin

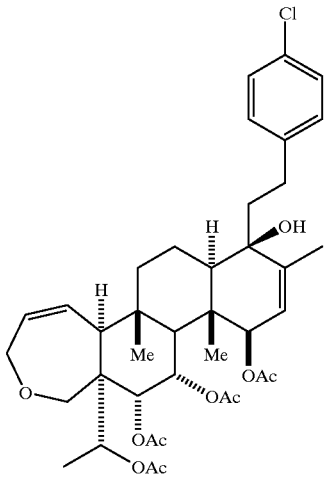

¹H NMR (CDCl₃) δ1.76 (s,3H), 7.11(d, 2H, J =8Hz), 7.25 (d, 2H, J =8 Hz); Mass Spectrum (CI, NH₄OAc): m/e 732(M+NH₄)

EXAMPLE 32

[5-S-5aα,5aα,7aα,8α,8β,11β,11aβ, 11bα,12α,13α,13aα]-13a-(1-R-acetoxyethyl)-8-hydroxy-8-(2-(3,4-dichlorophenyl)ethyl)-11,12,13-triacetoxy-5b,9,11a-trimethyl-1,3,5a,5b,6,7,7a,8,11,11a,11b,12,13,13a-tetradecahydrophenanthro [2,1-c]oxepin

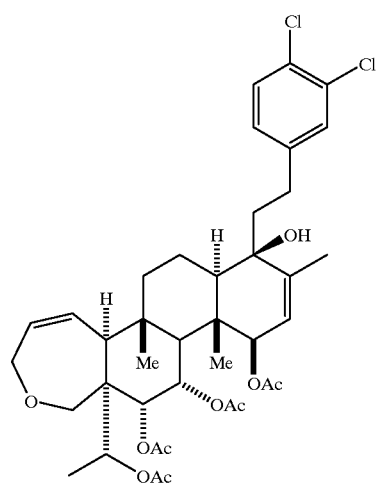

¹H NMR (CDCl₃) δ1.76 (s,3H), 7.02 (d, 1H, J =8 Hz), 7.27 (s, 1H), 7.35 (d, 1H, J =8 Hz); Mass Spectrum (CI, NH₄OAc): m/e 766(M+NH₄)

EXAMPLE 33

[5-S-5aα,5aα,7aα,8α,8β,11β,11aβ,11bα,12α,13α,13aα]-13a-(1-R-acetoxyethyl)-8-hydroxy-8-(2-(2-methylphenyl)ethyl)-11,12,13-triacetoxy-5b,9,11a-trimethyl-1,3,5a,5b,6,7,7a,8,11,11a,11b,12,13,13a-tetradecahydrophenanthro [2,1-c]oxepin

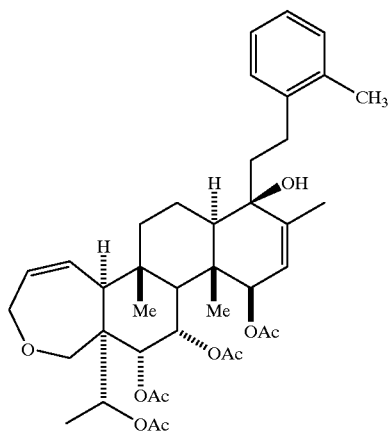

¹H NMR δ7.10–7.12 (m, 5 H), 5.22 (s, 1H), 5.09(s, 1H), 2.37–2.44 (m, 1H), 2.32 (s, 3 H), 2.20–2.26(m, 1 H), 1.79 (s, 3H); Mass Spectrum (APCI): m/e 712 (M+NH₄)

EXAMPLE 34

[5-S-5aα,5aα,7aα,8α,8β,11β,11aβ,11bα,12α,13α,13aα]-13a-(1-R-acetoxyethyl)-8-hydroxy-8-(2-(3-methylphenyl)ethyl)-11,12,13-triacetoxy-5b,9,11a-trimethyl-1,3,5a,5b,6,7,7a,8,11,11a,11b,12, 13,13a-tetradecahydrophenanthro [2,1-c]oxepin

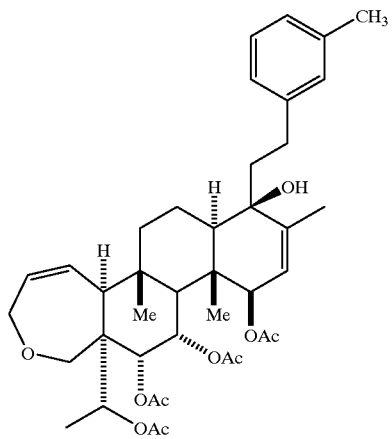

¹H NMR (CDCl₃) δ1.78 (s,3H), 2.34 (s, 3H), 6.92–7.02 (m, 3H), 7.17 (t, 1H, J =7 Hz); Mass Spectrum (CI, NH₄OAc): m/e 712(M+NH₄)

EXAMPLE 35

[5-S-5aα,5aα,7aα,8α,8β,11β,11aβ,11bα,12α,13α,13aα]-13a-(1-R-acetoxyethyl)-8-hydroxy-8-(2-(4-methylphenyl)ethyl)-11,12,13-triacetoxy-5b,9,11a-trimethyl-1,3,5a,5b,6,7,7a,8,11,11a,11b,12,13,13a-tetradecahydrophenanthro [2,1-c]oxepin

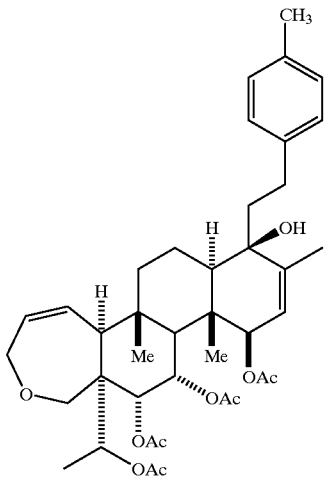

¹H NMR (CDCl₃) δ1.78 (s,3H), 2.33 (s, 3H), 7.06–7.11 (m, 4H), Mass Spectrum (CI, NH₄OAc): m/e 712(M+NH₄)

EXAMPLE 36

[5-S-5aα,5aα,7aα,8α,8β,11β,11aβ,11bα,12α,13α,13aα]-(1-R-acetoxyethyl)-8-hydroxy-8-(2-(2,5-dimethylphenyl)ethyl)-11,12,13-triacetoxy-5b,9,11a-trimethyl-1,3,5a,5b,6,7,7a,8,11,11a,11b, 12,13,13a-tetradecahydrophenanthro [2,1-c]oxepin

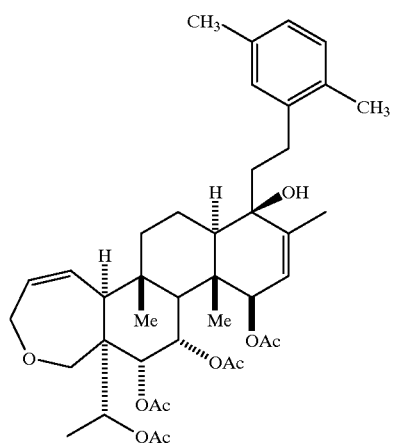

¹H NMR (CDCl₃) δ 1.81 (s,3H), 2.29 (s, 3H), 2.32 (s, 3H), 6.93 (S, 1H), 6.95 (d, 1H, J=7 Hz), 7.04 (d, 1H, J=7 Hz); Mass Spectrum (CI, NH₄OAc): m/e 726(M+NH₄)

EXAMPLE 37

[5-S-5aα,5aα,7aα,8α,8β,11β,11aβ,11bα,12α,13α,13aα]-13a-(1-R-acetoxyethyl)-8-hydroxy-8-(2-(2-trifluoromethylphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

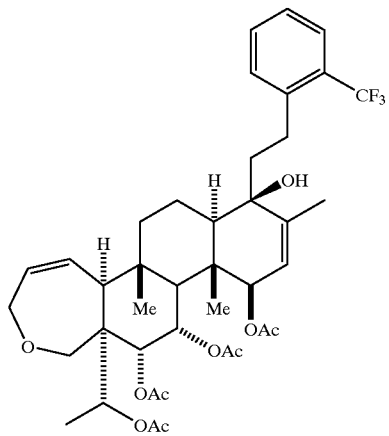

¹H NMR δ 7.62 (d, 1 H, J=8.0 Hz), 7.47 (t, 1 H, J=7.6 Hz), 7.26–7.31 (m, 2H), 5.23 (s, 1H), 5.09 (s, 1 H), 2.61–2.66 (m, 1H), 2.31–2.36 (m, 1H), 1.83 (s, 3H); Mass Spectrum (APCI): m/e 766 (M+NH$_4$)

EXAMPLE 38

[5-S-5aα,5aα,7aα,8α,8β,11β,11aβ,11bα,12α,13α,13aα]-13a-(1-R-acetoxyethyl)-8-hydroxy-8-(2-(3-trifluoromethylphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

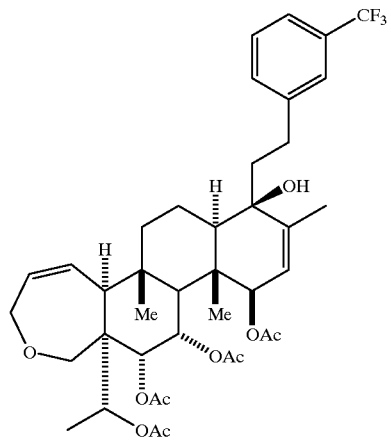

¹H NMR (CDCl$_3$) δ 1.80 (s,3H), 7.35–7.48 (m, 3H), Mass Spectrum (CI, NH$_4$OAc): m/e 766(M+NH$_4$)

EXAMPLE 39

[5-S-5aα,5aα,7aα,8α,8β,11β,11aβ,11bα,12α,13α,13aα]-13a-(1-R-acetoxyethyl)-8-hydroxy-8-(2-(naphth-2-yl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

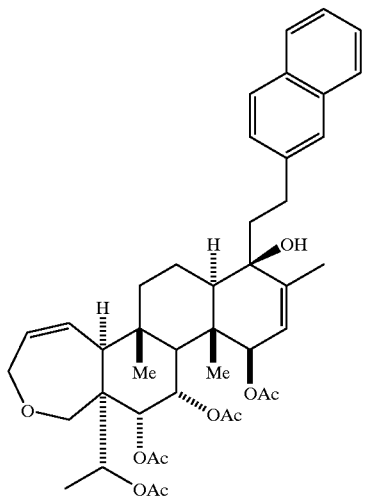

¹H NMR δ 7.77–7.81 (m, 3 H), 7.62 (s, 1 H), 7.46 (t, 1H, J=8.0 Hz), 7.42 (t, 1 H, J=7.7 Hz), 7.31 (d, 1 H, J=8.2 Hz), 5.26 (s, 1H), 5.12 (s, 1H), 2.56–2.62 (m, 1 H), 2.41–2.47 (m, 1H), 1.82 (s, 1H); Mass Spectrum (APCI): m/e 748 (M+NH$_4$)

EXAMPLE 40

[5-S-5aα,5aα,7aα,8α,8β,11β,11aβ,11bα,12α,13α,13aα]-13a-(1-R-acetoxyethyl)-8-hydroxy-8-(2-(naphth-2-yl)ethyl)-11,12-diacetoxy-13-hydroxy-5b,9,11a-trimethyl-1,3,5a,5b,6,7,7a,8,11,11a,11b,12,13,13a-tetradecahydrophenanthro[2,1-c]oxepin

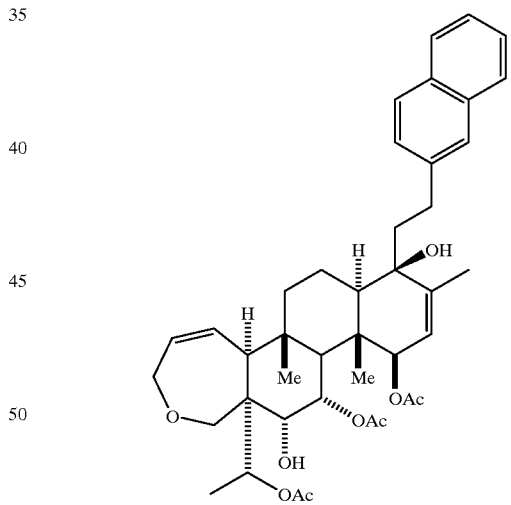

The title compound was isolated in the reaction that produced Example 39.

¹H NMR δ 7.79–7.83 (m, 3 H), 7.63 (s, 1H), 7.48 (t, 1H, J=6.4 Hz), 7.44 (t, 1H, J=8.9 Hz), 5.30 (s, 1H), 5.17 (s, 1H), 4.69 (bs, 1H), 2.61–2.65 (m, 1H), 2.43–2.48 (m, 1H), 1.84 (s, 3H); Mass Spectrum (APCI): m/e 706 (M+NH$_4$)

EXAMPLE 41

[5-S-5aα,5aα,7aα,8α,8β,11β,11aβ,11bα,12α,13α,13aα]-13a-(1-R-acetoxyethyl)-8-hydroxy-8-(2-(naphth-1-yl)ethyl)-11,12, 13-triacetoxy-5b,9,11a-trimethyl-1,3,5a,5b,6,7,7a,8,11,11a,11b,12,13,13a-tetradecahydrophenanthro[2,1-c]oxepin

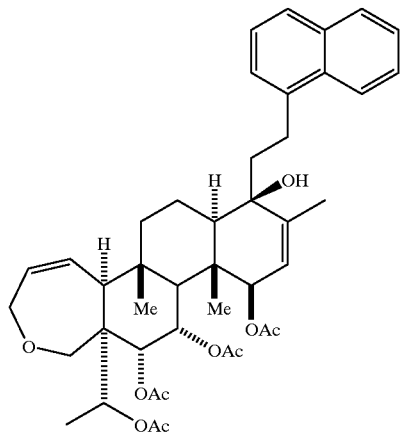

¹H NMR (CDCl₃) δ 8.01 (d, 1H, J=8.4 Hz), 7.87 (d, 1H, J=8.0 Hz), 7.76 (d, 1H, J=8.3 Hz), 7.55 (t, 1H, J=7.1 Hz), 7.50 (t, 1H, J=7.3 Hz), 7.42 (t, 1H, J=7.6 Hz), 7.32 (d, 1H, J=6.8 Hz), 2.87–2.94 (m, 1H), 2.76–2.82 (m, 1H), 1.84 (s, 3H); Mass Spectrum (APCI): m/e 748 (M+NH₄)

EXAMPLE 42

[5-S-5aα,5aα,7aα,8α,8β,11β,11aβ,11bα,12α,13α,13aα]-13a-(1-R-acetoxyethyl)-8-hydroxy-8-(2-(2-methylnaphth-1-yl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

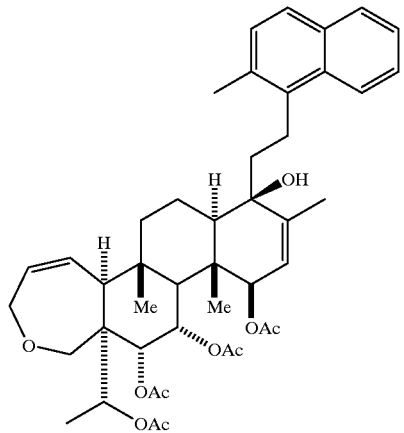

¹H NMR (CDCl₃); δ 7.94 (d, 1H, J=8.7 Hz), 7.82, (d, 1H, J=8.2 Hz), 7.65 (d, 1H, J=8.2 Hz) 7.43–7.49 (m, 2H0, 7.31 (d, 1H, 8.3 Hz), 3.71–3.78 (m, 2H), 2.12 (s, 3H), 2.047 (s, 3H), 2.04 (s, 3H), 2.028 (s, 3H), 1.94 s, 3H). Mass Spectrum (L788845) (CI, NH₄OAc): m/e 762(M+NH₄);

EXAMPLE 43

[5-S-5aα,5aα,7aα,8α,8β,11β,11aβ,11bα,12α,13α,13aα]-13a-(1-R-acetoxyethyl)-8-hydroxy-8-(2-(2-methylnaphth-1-yl)ethyl)-11,12-diacetoxy-13-hydroxy-5b,9,11a-trimethyl-1,3,5a,5b,6,7,7a,8,11,11a,11b,12,13,13a-tetradecahydrophenanthro[2,1-c]oxepin

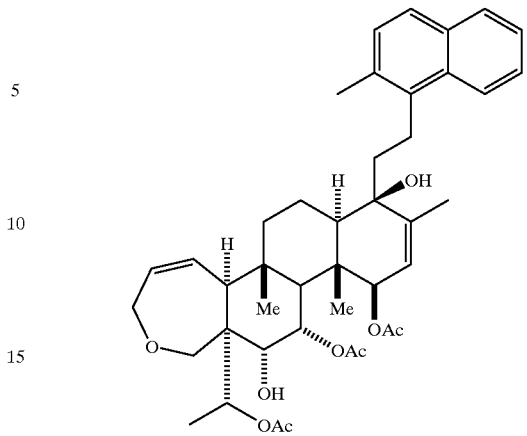

The title compound was obtained as a byproduct in Example 42.

¹H NMR (CDCl₃) δ 7.95 (d, 1H, J=8.3 Hz), 7.83 (d, 1H, J=8.0 Hz), 7.65 (d, 1H, J=8.5 Hz), 7.42–7.48 (m, 2H), 7.31 (d, 1H, J=8.3 Hz), 4.20 (d, 1H, J=11.9 Hz), 3.68 (d, 1H, J=11.9 Hz), 2.109 (s, 3H), 2.101 (s, 3H), 2.080 (s, 3H), 1.96 (s, 3H). Mass Spectrum (L788846) (CI, NH₄OAc): m/e 720 (M+NH₄)

EXAMPLE 44

[5-S-5aα,5aα,7aα,8α,8β,11β,11aβ,11bα,12α,13α,13aα]-13a-(1-R-acetoxyethyl)-8-hydroxy-8-(2-(2-methoxyphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

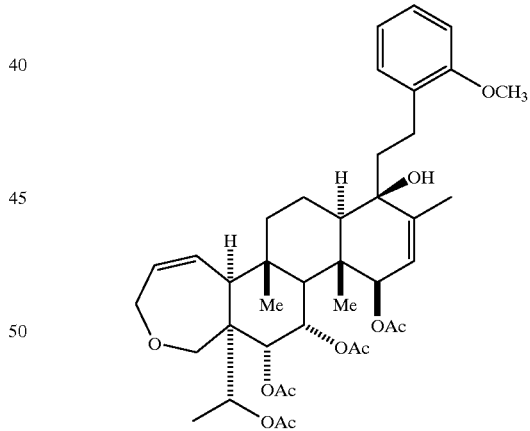

¹H NMR δ 7.17 (t, 1H, J=7.5 Hz), 7.11 (7.1 Hz), 6.88 (t, 1H, J=7.3 Hz), 6.85 (d, 1H, J=8.4 Hz), 5.20 (s, 1H), 5.09 (s, 1H), 3.84 (s, 3H), 2.37–2.41 (m, 1H), 2.26–2.31 (m, 1H), 1.79 (s, 3H); Mass Spectrum (APCI): m/e 728 (M+NH₄)

EXAMPLE 45

[5-S-5aα,5aα,7aα,8α,8β,11β,11aβ,11bα,12α,13α,13aα]-13a-(1-R-acetoxyethyl)-8-hydroxy-8-(2-(3-methoxyphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

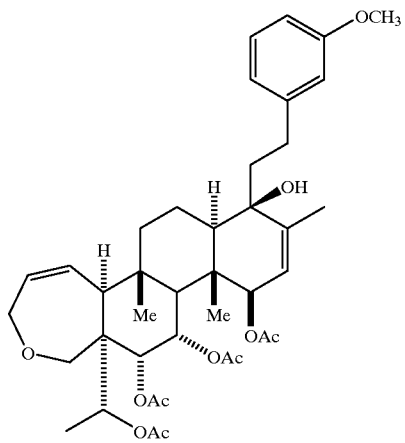

¹H NMR (CDCl₃) δ 1.80 (s,3H), 3.79 (s, 3H), 6.70–6.76 (m, 3H), 7.19 (t, 1H, J=8 Hz); Mass Spectrum (CI, NH₄OAc): m/e 728 (M+NH₄)

EXAMPLE 46

[5-S-5aα,5aα,7aα,8α,8β,11β,11aβ,11bα,12α,13α,13aα]-13a-(1-R-acetoxyethyl)-8-hydroxy-8-(2-(4-methoxyphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

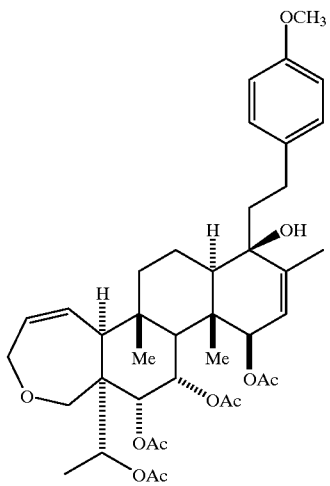

¹H NMR δ 7.09 (d, 2H, J=8.4 Hz), 6.84 (d, 2H, J=8.4 Hz), 5.22 (s, 1H), 5.09 (s, 1H), 3.80 (s, 3H), 2.33–2.39 (m, 1H), 2.19–2.25 (m, 1H), 1.77 (s, 3H); Mass Spectrum (APCI): m/e 728 (M+NH₄)

EXAMPLE 47

[5-S-5aα,5aα,7aα,8α,8β,11β,11aβ,11bα,12α,13α,13aα]-13a-(1-R-acetoxyethyl)-8-hydroxy-8-(2-(2,3-dimethoxyphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

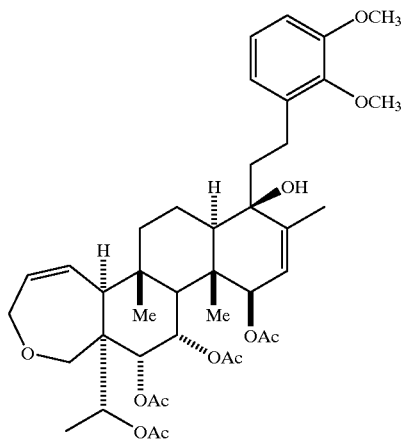

¹H NMR (CDCl₃) δ 1.81 (s,3H), 3.83 (s, 3H), 3.85 (s, 3H), 6.72 (d, 1H, J=8 Hz), 6.78 (d, 1H, J=8 Hz), 6.95 (t, 1H, J=8 Hz); Mass Spectrum (CI, NH₄OAc): m/e 758(M+NH₄)

EXAMPLE 48

[5-S-5aα,5aα,7aα,8α,8β,11β,11aβ,11bα,12α,13α,13aα]-13a-(1-R-acetoxyethyl)-8-hydroxy-8-(2-(3,4-dimethoxyphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

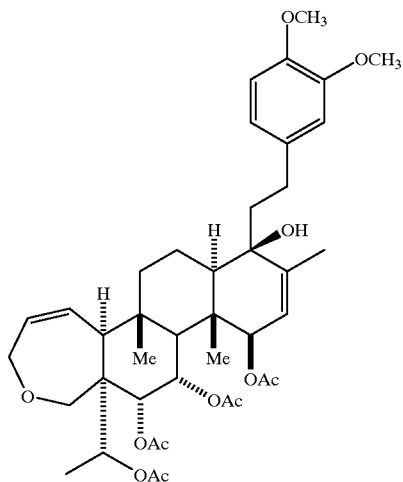

¹H NMR (CDCl₃) δ 1.77 (s,3H), 3.86 (s, 3H), 3.88 (s, 3H), 6.70 (S, 1H), 6.71 (d, 1H, J=8 Hz), 6.78 (d, 1H, J=8 Hz), 6.80 (t, 1H, J=8 Hz); Mass Spectrum (CI, NH₄OAc): m/e 758 (M+NH₄)

EXAMPLE 49

[5-S-5aα,5aα,7aα,8α,8β,11β,11aβ,11bα,12α,13α,13aα]-13a-(1-R-acetoxyethyl)-8-hydroxy-8-(2-(2,5-dimethoxyphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

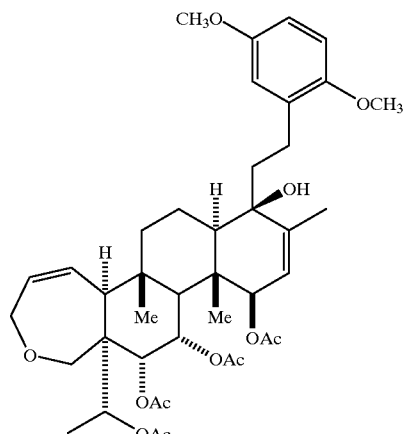

¹H NMR (CDCl₃) δ 1.79 (s,3H), 3.77 (s, 3H), 3.80 (s, 3H), 6.69 (d, 1H, J=7 Hz), 6.70 (s, 1H), 6.77 (d, 1H, J=7 Hz); Mass Spectrum (CI, NH₄OAc): m/e 758(M+NH₄)

EXAMPLE 50

[5-S-5aα,5aα,7aα,8α,8β,11β,11aβ,11bα,12α,13α,13aα]-13a-(1-R-acetoxyethyl)-8-hydroxy-8-(2-(3,5-dimethoxyphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

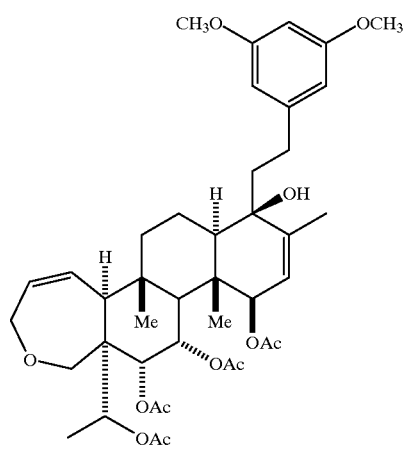

¹H NMR (CDCl₃) δ 1.76 (s,3H), 3.78 (s, 6H), 6.32 (s, 3H); Mass Spectrum (CI, NH₄OAc): m/e 758(M+NH₄)

EXAMPLE 51

[5-S-5aα,5aα,7aα,8α,8β,11β,11aβ,11bα,12α,13α,13aα]-13a-(1-R-acetoxyethyl)-8-hydroxy-8-(2-(3,4-methylenedioxyphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

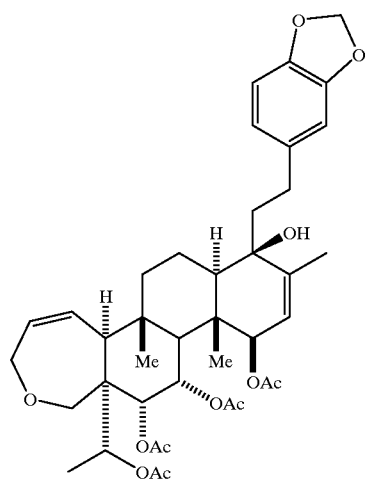

¹H NMR (CDCl₃) δ 1.76 (s,3H), 5.92 (s, 2H), 6.61 (d, 1H, J=8 Hz), 6.65 (s, 1H), 6.73 (d, 1H, J=8 Hz); Mass Spectrum (CI, NH₄OAc): m/e 742(M+NH₃)

EXAMPLE 52

[5-S-5aα,5aα,7aα,8α,8β,11β,11aβ,11bα,12α,13α,13aα]-13a-(1-R-acetoxyethyl)-8-hydroxy-8-(2-(2,3-methylenedioxyphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

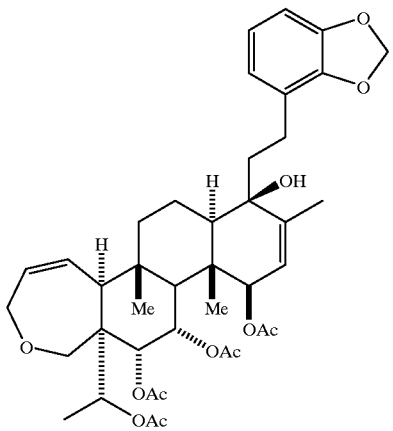

¹H NMR (CDCl₃) δ 1.76 (s,3H), 5.94–5.99 (m, 2H), 6.4–7.2 (m, 3H); Mass Spectrum (CI, NH₄OAc): m/e 742 (M+NH₄)

EXAMPLE 53

[5-S-5aα,5aα,7aα,8α,8β,11β,11aβ,11bα,12α,13α,13aα]-13a-(1-R-acetoxyethyl)-8-hydroxy-8-(2-(4-N,N-dimethylaminophenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

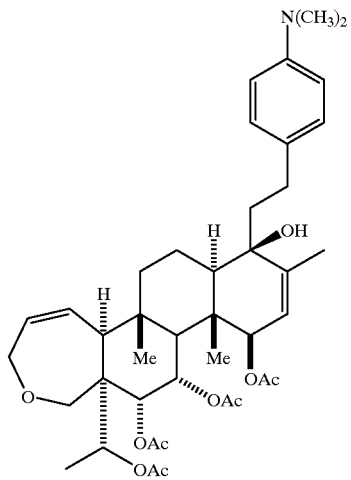

¹H NMR (CDCl₃) δ 1.78 (s,3H), 2.92 (s, 6H), 6.71 (d, 2H, J=8 Hz), 7.04 (d, 2H, J=8 Hz); Mass Spectrum (CI, NH₄OAc): m/e 724 (M+1)

EXAMPLE 54

[5-S-5aα,5aα,7aα,8α,8β,11β,11aβ,11bα,12α,13α,13aα]-13a-(1-R-acetoxyethyl)-8-hydroxy-8-(2,2-diphenylethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

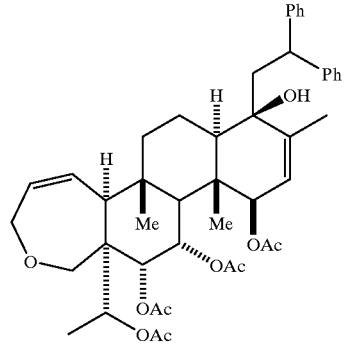

¹H NMR (CDCl₃) δ 7.13–7.33 (m, 10H), 5.30 (s, 1H), 4.95 (s, 1H), 3.56 (d, 1H, J=9.9 Hz), 1.68 (s, 3H); Mass Spectrum (APCI): m/e 774 (M+NH₄)

EXAMPLE 55

[5-S-5aα,5aα,7aα,8α,8β,11β,11aβ,11bα,12α,13α,13aα]-13a-(1-R-acetoxyethyl)-8-hydroxy-8-(2-(2-methoxy-5-methylphenyl)ethyl)-11,12,13-triacetoxy-5b,9,11a-trimethyl-1,3,5a,5b,6,7,-7a,8,11,11a,11b,12,13,13a-tetradecahydrophenanthro[2,1-c]oxepin

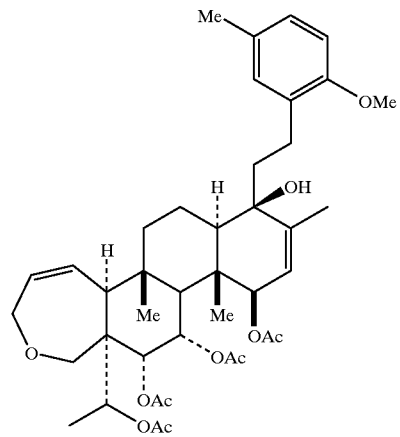

¹H NMR (CDCl₃) δ 6.97 (d, 1H, J=8.2 Hz), 6.92 (s, 1H), 6.74 (d, 1H, J=8.2 Hz), 5.20 s, 1H), 5.08 (s, 1H), 3.81 (s, 3H), 2.28 (s, 3H), 1.80 (s, 3H); Mass Spectrum (APCI): m/e 742 (M+NH₄)

EXAMPLE 56

[5-S-5aα,5aα,7aα,8α,8β,11β,11aβ,11bα,12α,13α,13aα]-13a-(1-R-acetoxyethyl)-8-hydroxy-8-(2-(thien-2-yl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

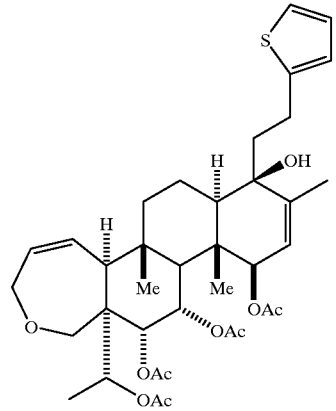

¹H NMR (CDCl₃) δ 7.13 (d, 1H, J=5.0 Hz), 6.92 (dd, 1H, J=4.8, 3.4 Hz), 6.80 (d, 1H, J=3.5 Hz) 5.22 (s, 1H), 5.07 (S, 1H), 2.62–2.69 (m, 1H), 2.46–2.52 (m, 1H), 1.77 (S, 3H); Mass Spectrum (APCI): m/e 704 (M+NH₄)

EXAMPLE 57

[5-S-5aα,5aα,7aα,8α,8β,11β,11aβ,11bα,12α,13α,13aα]-13a-(1-R-acetoxyethyl)-8-hydroxy-8-(2-(2,6-dimethoxyphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

71

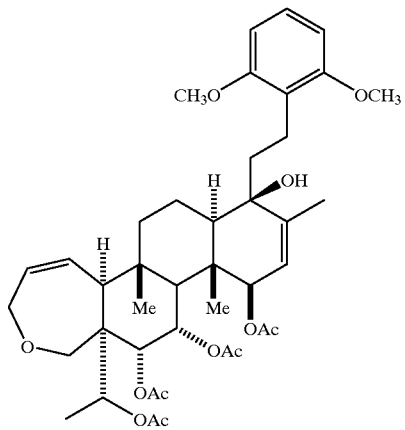

$^1$H NMR (CDCl$_3$) δ 7.10 (t, 1H, J=8.2 Hz), 6.53 (d, 2H, J=8.3 Hz) 5.10 (s, 1H), 5.19 (s, 1H), 3.82 (s, 3H), 2.32–2.46 (m, 2H), 1.81 (s, 3H); Mass Spectrum (APCI): m/e 758 (M+NH$_4$)

EXAMPLE 58

[5-S-5aα,5aα,7aα,8α,8β,11β,11aβ,11bα,12α,13α,13aα]-13a-(1-R-acetoxyethyl)-8-hydroxy-8-(2-phenyl-1-methylethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

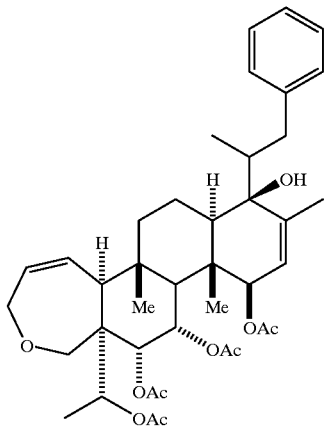

The title compound was isolated as a 1:2 mixture of methyl isomers.

$^1$H NMR (CDCl$_3$); isomer a: δ 5.11 (bs, 1H), 1.85 (s, 3H), 0.84 (d, 3H, J=6.9 Hz); isomer b: δ 5.08 (bs, 1H), 1.80 (s, 3H), 0.90 (d, 3H, J=6.9 Hz). Mass Spectrum (APCI): m/e 712 (M+NH$_4$)

EXAMPLE 59

[5-S-5aα,5aα,7aα,8α,8β,11β,11aβ,11bα,12α,13α,13aα]-13a-(1-R-acetoxyethyl)-8-hydroxy-8-(2-phenyl-2-methylpropyl)-11,12,13-triacetoxy-5b,9,11a-trimethyl-1,3,5a,5b,6,7,7a,8,11,11a,11b,12,13,13a-tetradecahydrophenanthro[2,1-c]oxepin

72

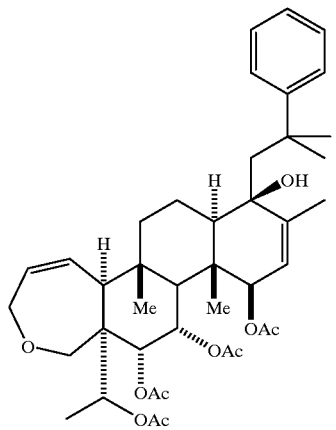

$^1$H NMR (CDCl$_3$) δ 7.45 (d, 2H, J=7.6 Hz), 7.37 (t, 2H, J=7.3 Hz), 7.17 (t, 1H, J=7.3 Hz), 5.08 (s, 1H), 4.90 (s, 1H), 1.85 (s 3H), 1.40 (s, 3H), 1.28 (s, 3H), 1.07 (s, 3H), 0.96 (s, 3H); Mass Spectrum (APCI): m/e 726 (M+NH$_4$)

EXAMPLE 60

[5-S-5aα,5aα,7aα,8α,8β,11β,11aβ,11bα,12α,13α,13aα]-13a-(1-R-acetoxyethyl)-8-hydroxy-8-(2-cyclohexylethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

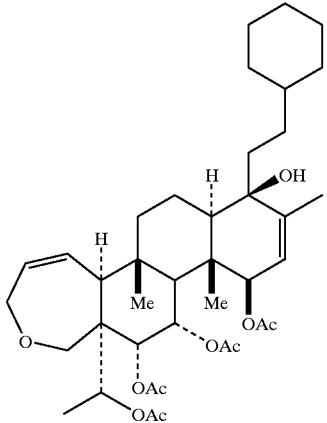

$^1$H NMR (CDCl$_3$) δ 5.13 (s, 1H), 5.02 (s, 1H), 1.68 (s, 3H); Mass Spectrum (APCI): m/e 704 (M+NH$_4$)

EXAMPLE 61

[5-S-5aα,5aα,7aα,8α,8β,11β,11aβ,11bα,12α,13α,13aα]-13a-(1-R-acetoxyethyl)-8-hydroxy-8-(2(1,3-dioxolan-2-yl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

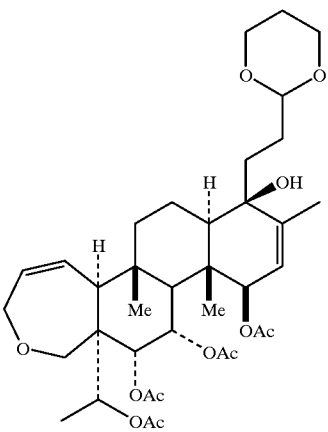

¹H NMR (CDCl₃) δ 5.01 (s, 1H), 5.12 (s, 1H), 4.48 (t, 1H, J=4.8 Hz),1.70 (s, 3H); Mass Spectrum (APCI): m/e 708 (M+NH₄)

EXAMPLE 62

[5-S-5aα,5aα,7aα,8α,8β,11β,11aβ,11bα,12α,13α,13aα]-13a-(1-R-acetoxyethyl)-8-hydroxy-8-(2-(2-hydroxyphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

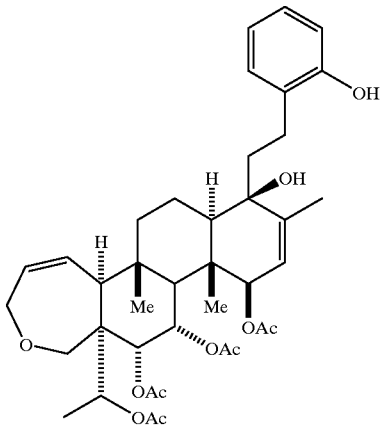

Step A: Preparation of 2-tetrahydropyranyloxyphenyl ethyl bromide

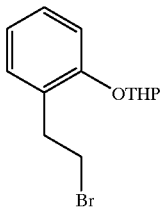

A solution of 2-methoxyphenethyl alcohol (5.0 g, 32.6 mmol) in 40 ml of CH₂Cl₂ was added dimethylaminopyridine (DMAP) (10 mg), Et₃N (11.4 ml, 81.8 mmol) and MsCl (5.05 ml, 65.2 mmol) at 0° C. After 1 h, the reaction mixture was poured into hexane and it was washed with NaHCO₃ (2×), water and dried with MgSO₄. Upon removal of solvents, the residue was dissolved in 50 ml of acetone and to the solution was added LiBr (11.34 g, 130.6 mmol). After the solution was heated at reflux for 16 h, it was poured into ether and washed with water, dried with MgSO₄, filtered and dried to afford 2-methoxyphenethyl bromide.

To a solution of 2-methoxyphenethyl bromide (1.07 g, 4.98 mmol) in 5 ml of CH₂Cl₂ was added BBr₃ (9.5 ml, 1.0 M in CH₂Cl₂) at −78° C. and it was allowed to warm to rt over 1.5 h. The reaction mixture was poured into CH₂Cl₂ and was washed with brine, dried to afford 2-hydroxy phenethyl bromide (quantitative).

To a solution of 2-hydroxyphenethyl bromide (241 mg, 1.20 mmol) in 6 ml of CH₂Cl₂ was added pyridinium p-toluene sulfonate (PPTS, 10 mg) and dihydropyran. After 2 h, volatiles were removed and the residue was purified by flash column to afford the title compound.

Step B: Preparation of [5-S-5aα,5aα,7aα,8α,8β,11β,11aβ,11bα,12α,13α,13aα]-13a-(1-R-acetoxyethyl)-8-hydroxy-8-(2-(2-hydroxyphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

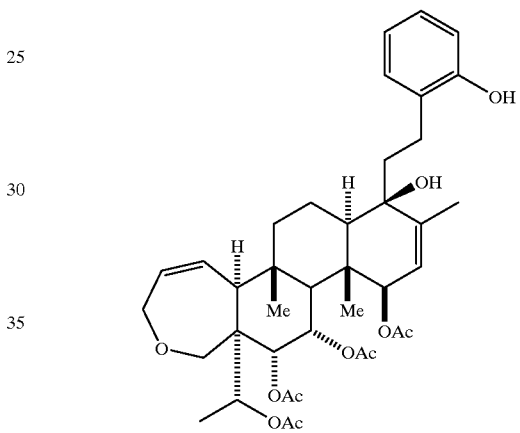

To a solution of [5-S-5aα,5aα,7aα,11β,11aβ,-11bα,12α,13α,13aα]-13a-(1-R-acetoxyethyl)-8-oxo-11,12,13-triacetoxy-5b,9,11a-trimethyl-1,3,5a,5b,6,7,7a,8,11,-11a,11b,12,13,13a,tetradecahydrophenanthro[2,1 -c]oxepin (65.5 mg, 0.114 mmol) in 6 ml of THF was added the Grignard reagent of 2-tetrahydropyranyloxy-phenylethyl bromide (0.68 mmol, 0.4 M in THF, prepared as in previous examples) at 0° C. After 25 min, the reaction mixture was quenched with 0.1 M phosphate buffer (pH=7) and was filtered through silica gel. The crude product was purified by HPLC to afford 78.2 mg. To the protected phenol product in 4 ml of methanol was added 10 mg TsOH and stirred at rt for 3.5 h. After removal of solvent, the reaction mixture was purified with HPLC to afford the title compound.

¹H NMR (CDCl₃) δ 7.11 (d, 1H J=7.6 HZ), 7.09 (t, 1H, J=7.5 Hz), 6.88 (t, 1H, J=7.6 Hz), 6.75 (d, 1H, J=7.8 Hz) 5.23 (s, 1H), 5.14 (s, 1H), 5.12 (s, 1H), 2.41–2.47 (m, 1H), 2.29–2.35 (m, 1H), 1.81 (s, 3H); Mass Spectrum (APCI): m/e 714 (M+NH₄)

EXAMPLE 63

[5-S-5aα,5aα,7aα,8α,8β,11β,11aβ,11bα,12α,13α,13aα]-13a-(1-R-acetoxyethyl)-8-hydroxy-8-(2-(2-methanesulfonyloxyphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

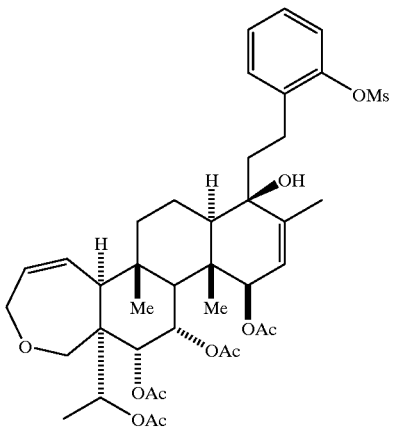

To a solution of [5-S-5aα,5aα,7aα,8α,8β,11β,11aβ,11bα, 12α,13α,13aα]-13a-(1-R-acetoxyethyl)-8-hydroxy-8-(2-(2-hydroxyphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin (12.1 mg, 0.017 mmol) in 2 ml of CH₂Cl₂ was added DMAP (1 mg), Et₃N (36.3 ul, 0.26 mmol) and Methanesulfonyl chloride(13.5 ul, 0.17 mmol) at 0° C. The reaction mixture was stirred at rt for 2 h and poured into ether. The organic solution was washed with NaHCO₃ and brine, dried with MgSO₄. The combined extracts were purified by HPLC to afford the title compound.

¹H NMR (CDCl₃) δ 7.34–7.36 (m, 1H), 7.26–7.28 (m, 3H), 5.09 (s, 1H), 5.23 (s, 1H), 3.25 (s, 3H), 2.51–2.58 (m, 1H), 2.31–2.37 (m, 1H), 1.80 (s, 3H); Mass Spectrum (APCI): m/e 792 (M+NH₄)

EXAMPLE 64

[5-S-5aα,5aα,7aα,8α,8β,11β,11aβ,11bα,12α,13α,13aα]-13a-(1-R-acetoxyethyl)-8-hydroxy-8-(2-(2-acetoxyphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin

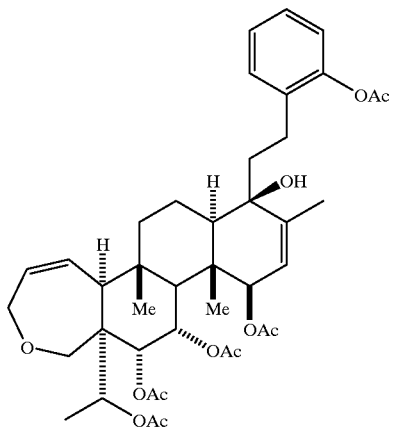

A solution of [5-S-5aα,5aα,7aα,8α,8β,11β,11aβ,11bα, 12α,13α,13aα]-13a-(1-R-acetoxyethyl)-8-hydroxy-8-(2-(2-hydroxyphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin (12.1 mg, 0.017 mmol) in 2 ml of CH₂Cl₂ was added DMAP (1 mg), pyridine (42 ul, 0.52 mmol) and Ac₂O (32.8 ul, 0.35 mmol) at rt. The reaction mixture was stirred at rt for 2 h and was poured into ether. The organic solution was washed with NaHCO₃ and brine, dried with MgSO₄. The combined extracts were purified by HPLC to afford the title compound.

¹H NMR (CDCl₃) δ 7.17–7.27 (m, 3H), 7.05 (d, 1H, J=8.0 Hz), 5.10 (s, 1H), 5.23 (s, 1H), 2.35 (s, 3H), 2.20–2.35 (m, 2H), 1.78 (s, 3H); Mass Spectrum (APCI): m/e 756 (M+NH₄)

EXAMPLE 65

[5-S-5aα,5aα,7aα,8α,8β,11β,11aβ,11bα,12α,13α,13aα]-13a-(1-R-acetoxyethyl)-8-hydroxy-8-(S-2-(phenyl)propyl)-11,12,13-triacetoxy-5b,9,11a-trimethyl-1,3,5a,5b,6,7,7a,8,11,11a,11b,12,13,13a-tetradecahydrophenanthro[2,1-c]oxepin

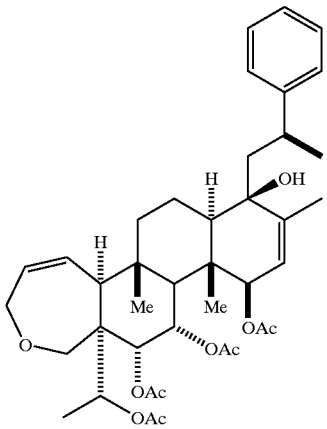

Step A: Preparation of R-(−)-2-phenylpropylbromide

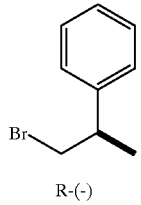

R-(−)

To a solution of R-(−)-2-phenylpropionic acid (1.04 g, 6.9 mmol) in 30 ml of THF was added LAH (6.9 ml, 1.0 M in THF)at 0° C. After it was stirred at rt for 14 h, it was poured into 2 N HCl and the organic layer was washed with NaHCO₃ and brine, dried with MgSO₄ to give the alkanol which was converted to the bromide by procedures previously described.

Step B: Preparation of [5-S-5aα,5aα,7aα,8α,8β,11β, 11aβ,11bα,12α,13α,13aα]-13a-(1-R-acetoxyethyl)-8-hydroxy-8-(S-2-(phenyl)propyl)-11,12,13-triacetoxy-5b,9, 11a-trimethyl-1,3,5a,5b,6,7,7a,8,11,11a,11b,12,13,13a-tetradecahydrophenanthro[2,1-c]oxepin

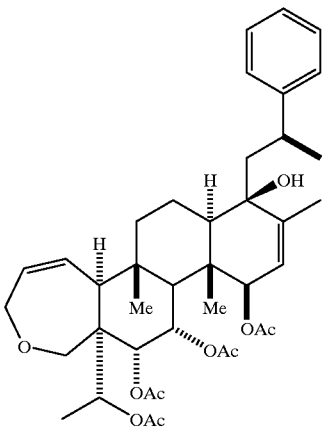

The title compound was prepared by procedures previously described using the Grignard reagent prepared from R-(-)-2-phenylpropylbromide.

$^1$H NMR (CDCl$_3$) δ 7.35 (t, 2H, J=7.8 Hz), 7.21–7.24 (m, 3H), 5.22 (s, 1H), 4.86 (s, 1H), 2.43 (p, 1H, J=7.3 Hz), 1.79 (s, 3H), 1.25 (d, 3H, J=7.1 Hz), 1.15 (d, 3H, J=7.6 Hz); Mass Spectrum (APCI): m/e 712 (M+NH$_4$)

EXAMPLE 66

[5-S-5aa,5aa,7aa,8a,8b,11b,11ab,11ba,12a,13a,13aa]-13a-(1-R-acetoxyethyl)-8-hydroxy-8-(2-(phenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin

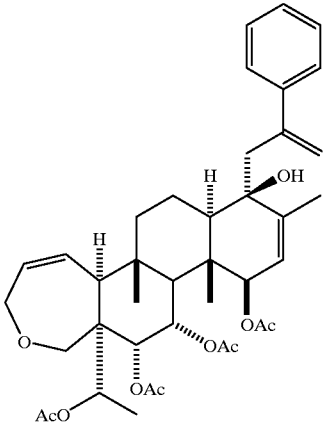

Step A: Preparation of 2-(phenyl)prop-2-enyltriethylsilane

2 g of (2-bromoallyl)trimethylsilane (10.4 mmole) and 500 mg of tetrakis (triphenylphosphine) palladium (0.4 mmole) in 5 ml of benzene were heated to 80° C. until a homogenous solution resulted. The mixture was cooled to 40° C. and 10 ml of a 1M solution of phenylmagnesium chloride in THF were slowly added. The deep red reaction mixture was stirred at 40° C. for 12 h and poured into 20 ml of water. Extraction with ethyl acetate, washing of the combined organic layers with aqueous sodium chloride then drying over MgSO$_4$ gave an oil which was purified by silica gel chromatography with 19:1 hexanes-ethyl acetate to afford the title compound as a yellow oil.

$^1$H NMR (CDCl$_3$) δ 0.06 (s, 9H, SiMe$_3$), 2.06 (s, 2H, CH$_2$), 4.91 (s, 1H, =CH$_2$), 5.17 (s, 1H, =CH$_2$), 7.26–7.64 (m, 2H, ar-H), 7.18–7.25 (m, 2H, ar-H).

Step B: Preparation of [5-S-5aa,5aa,7aa,8a,8b,11b,11ab,11ba,12a,13a,13aa]-13a-(1-R-acetoxyethyl)-8-hydroxy-8-(2-(phenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin

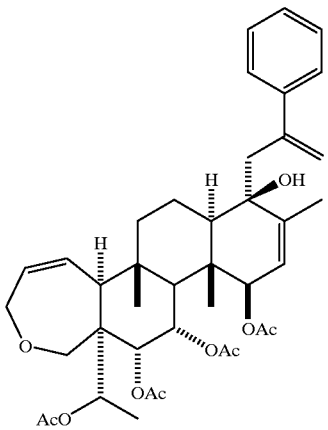

To a solution of 40 mg of [5-S-5aα,5aα,7aα,11β,11aβ,11bα,12α,13α,13aα]-13a-(1-R-acetoxyethyl)-8-oxo-11,12,13-triacetoxy-5b,9,11a-trimethyl-1,3,5a,5b,6,7,7a,8,11,11a,11b,12,13,13a, tetradecahydrophenanthro[2,1-c]oxepin (0.07 mmole) in 2 ml of CH$_2$Cl$_2$ was added 0.35 ml of a 1M solution of TiCl$_4$ in CH$_2$Cl$_2$ at -78° C. The resulting yellow suspension was stirred for 10 minutes then 0.2 ml of 2-(phenyl)prop-2-enyltrimethylsilane were added. Stirring was continued at -40° C. until TLC control showed no remaining strting material (approx. 14 h). 20 ml of water were added, the mixture was extracted with ethyl acetate, the organic phase was washed with aqueous sodium chloride then was dried over MgSO$_4$ and concentrated. The residue was first filtered through a plug of silica gel and then purified by HPLC (Waters RCM, Prep Nova-Pak HR Silica, 2 25×100 mm cartridges) to afford the title compound as a white solid.

$^1$H NMR (CDCl$_3$) δ 2.79 and 2.88 (AB, 2H, J=14.0 Hz, CH$_2$), 3.64 and 3.69 (AB, 2H, J=12.0 Hz, C24-H), 4.13 and 4.33 (AB, 2H, J=17.5 Hz, C3-H), 5.05 (brs, 1H, C16-H), 5.10 (brs, 1H, =CH$_2$), 5.26 (brs, 1H, =CH$_2$), 7.27–7.37 (m, 5H, ar-H); $^{13}$C NMR (CDCl$_3$) δ 117.2, 125.8, 126.6, 126.9, 127.0, 127.8, 128.2, 136.9, 143.2, 144.9; Mass Spectrum (APCI): m/e 710 (M+NH$_4$).

EXAMPLE 67

[5-S-5aa,5aa,7aa,8a,8b,11b,11ab,11ba,12a,13a,13aa]-13a-(1-R-acetoxyethyl)-8-hydroxy-8-(R-2-phenylpropyl)-11,12,13-triacetoxy-5b,9,11a-trimethyl-1,3,5a,5b,6,7,7a,8,11,11a,11b,12,13,13a-tetradecahydrophenanthro[2,1-c]oxepin

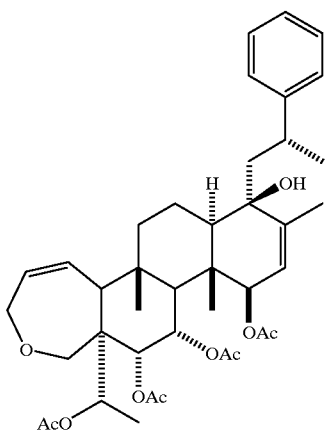

19 mg of [5-S-5aa,5aa,7aa,8a,8b,11b,11ab,11ba,12a,13a, 13aa]-13a-(1-R-acetoxyethyl)-8-hydroxy-8-(2-(phenyl) prop-2-enyl)-11,12 13-triacetoxy-5b,9,11a-trimethyl-1,3, 5a5b,6,7-7a,8,11,11a,11b,12,13,13a-tetradecahydrophenanthro[2,1-c]oxepin (0.027 mmole) were dissolved in 10 ml of dry THF. The solution was degassed under reduced pressure and saturated with nitrogen, the procedure being repeated several times. 15 mg of Wilkinson's catalyst [(PPh$_3$)$_3$RhCl] were added and the solution was degassed and saturated with hydrogen in the previously described manner. The reaction vessel was now pressurized with H$_2$ to 50 psi and hydrogenated on a Parr-apparatus for 23 h at 25° C. After that time the solvent was removed under reduced pressure. The residue was first filtered through a plug of silica gel and then purified by HPLC (Waters RCM, Prep Nova-Pak HR Silica, 2 25×100 mm cartridges) to afford the title compound as a white solid.

$^1$H NMR (CDCl$_3$) δ 1.30 (d, 3H, J=7.0 Hz, CH$_3$), 2.39 (m, 1H, CH), 3.70 and 3.76 (AB, 2H, J=11.5 Hz, C24-H), 4.18 and 4.38 (AB, 2H, J=17.0 Hz, C3-H), 7.16–7.18 (m, 3H, ar-H), 7.25–7.28 (m, 2H, ar-H); $^{13}$C NMR (CDCl$_3$) δ 25.8 (CH$_3$), 35.9 (CH), 125.4, 126.0, 126.6, 126.9, 128.1, 128.3, 137.8, 148.6; Mass Spectrum (APCI): m/e 712 (M+NH$_4$).

EXAMPLE 68

[5-S-5aa,5aa,7aa,8a,8b,11b,11ab,11ba,12a,13a,13aa]-13a-(1-R-acetoxyethyl)-8-hydroxy-8-(2-(phenyl)prop-2-enyl)-10-cyano-11,12,13-triacetoxy-5b,9,11a-trimethyl-1,3,5a,5b,6,7,7a,8,9,10,11,11a,11b,12,13,13a-hexadecahydrophenanthro[2,1-c]oxepin

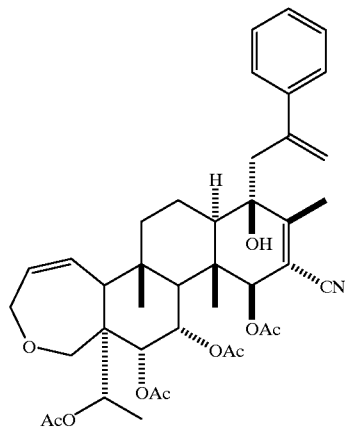

The title compound was prepared from [5-S-5aa,5aa,7aa 8a,8b,10a,11b,11ab,11ba,12a,13a,13aa]-13a-(1-R-acetoxyethyl)-8-oxo-10-cyano-11,12,13-triacetoxy-5b,9, 11a-trimethyl-1,3,5a,5b,6,7,7a,8,9,10,11,11a,11b,12,13,13a-hexa-decahydrophenanthro[2,1-c]oxepin according to procedures described in Example 66.

$^1$H NMR (CDCl$_3$) δ 2.70 and 2.90 (AB, 2H, J=14.0 Hz, CH$_2$), 3.10 (dd, J$_1$=J$_2$=10.4 Hz, C15-H), 3.60 and 3.68 (AB, 2H, J=12.0 Hz, C24-H), 4.12 and 4.30 (AB, 2H, J=17.5 Hz, C3-H), 4.92 (d, 1H, J=10.4 Hz, C16-H), 5.18 (brs, 1H, =CH$_2$), 5.30 (brs, 1H, =CH$_2$), 7.25–7.28 (m, 2H, ar-H), 7.36–7.40 (m, 3H, ar-H); Mass Spectrum (APCI): m/e 737 (M+NH$_4$).

EXAMPLE 69

[5-S-5aα,5aα,7aα,8α,8β,11β,11aβ,11bα,12α,13α,13aα]-13a-(1-R-acetoxyethyl)-8-hydroxy-8-(2-(phenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin-3-one The title compound was prepared from [5-S-5aα,5aα, 7aα,11β,11aβ,11bα,12α,13α,13aα]-13a-(1-R- acetoxyethyl)-8-oxo-11,12,13-triacetoxy-5b,9,11a-trimethyl-1,3,5a,5b,6,7,7a,8,11,11a,11b,12,13,13a, tetradecahydrophenanthro[2,1-c]oxepin-3-one according to procedures described in Example 66.

$^1$H NMR (CDCl$_3$) δ 0.30 (m, 1H, C13-H), 2.79 and 2.86 (AB, 2H, J=14.5 Hz, C18-CH$_2$), 4.13 and 4.44 (AB, 1H, J=12.0 Hz, C24-H), 5.09 (s, 1H, =CH$_2$), 5.26 (s, 1H, =CH$_2$), 6.03 (d, 1H, J=12.0 Hz, C2-H), 6.23 (dd, 1H, J$_1$=9.0 Hz, J$_2$=12.0 Hz, C1-H), 7.26–7.38 (m, 5H, ar-H); Mass Spectrum (APCI): m/e 724 (M+NH$_4$).

The following two examples were obtained as a minor products from the previous example:

EXAMPLE 70
[5-S-5aα,5aα,7aα,10α,11β,11aβ,11bα,12α,13α,13aα]-13a-(1-R-acetoxyethyl)-8-oxo-10α-(2-(phenyl)prop-2-enyl)-11,12,13-triacetoxy-5b,9β,11a-trimethyl-1,3,5a,5b,6,7,7a,8,9,10,11,11a,11b,12,13,13a-hexadecahydrophenanthro[2,1-c]oxepin-3-one

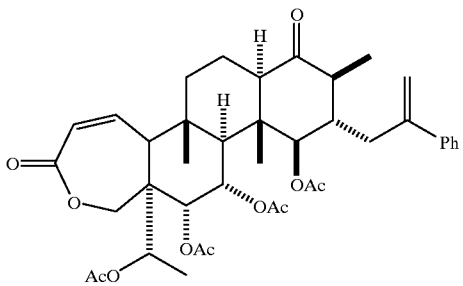

$^1$H NMR (CDCl$_3$) δ 0.90 (d, 3H, J=7.5 Hz, C17-Me), 2.28 (q, 1H, J=7.5 Hz, C17-H), 2.58 and 3.55 (ABX, 2H, J$_{AB}$=13.5 Hz, J$_{AX}$=13.0 Hz, J$_{BX}$=3.0 Hz, C16-CH$_2$), 4.15 and 4.49 (AB, 1H, J=12.5 Hz, C24-H), 5.06 (s, 1H, =CH$_2$), 5.34 (s, 1H, =CH$_2$), 6.11 (d, 1H, J=12.5 Hz, C2-H), 6.40 (dd, 1H, J$_1$=9.0 Hz, J$_2$=12.5 Hz, C1-H), 7.26–7.41 (m, 5H, ar-H); $^{13}$C NMR (CDCl$_3$) δ 66.2 (C24), 116.0 (=CH$_2$), 123.3 (C2), 126.5, 127.7, 128.3, 139.4, 142.3 (C1), 146.5, 168.5, 169.4, 170.0, 170.6, 171.6, 212.5 (C18); Mass Spectrum (APCI): m/e 724 (M+NH$_4$).

EXAMPLE 71
[5-S-5aα,5aα,7aα,10α,11β,11aβ,11bα,12α,13α,13aα]-13a-(1-R-acetoxyethyl)-8-oxo-10α-(2-(phenyl)prop-2-enyl)-11,12,13-triacetoxy-5b,9α,11a-trimethyl-1,3,5a,5b,6,7,7a,8,9,10,11,11a,11b,12,13,13a-hexadecahydrophenanthro[2,1-c]oxepin-3-one

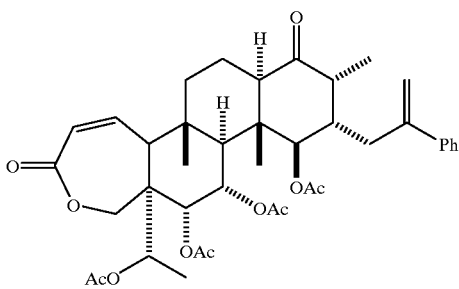

$^1$H NMR (CDCl$_3$) δ 1.07 (d, 3H, J=6.5 Hz, C17-Me), 4.17 and 4.49 (AB, 1H, J=12.5 Hz, C24-H), 5.21 (s, 1H, =CH$_2$), 5.39 (s, 1H, =CH$_2$), 5.10 (s, 1H, C15-H), 6.10 (d, 1H, J=12.5 Hz, C2-H), 6.39 (dd, 1H, J$_1$=9.0 Hz, J$_2$=12.5 Hz, C1-H), 7.27–7.43 (m, 5H, ar-H); Mass Spectrum (APCI): m/e 724 (M+NH$_4$).

EXAMPLE 72

[5-S-5aa,5aa,7aa,8a,8b,11b,11ab,11ba,12a,13a,13aa]-13a-(1-R-acetoxyethyl)-8-hydroxy-8-(2-(2-methoxyphenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin

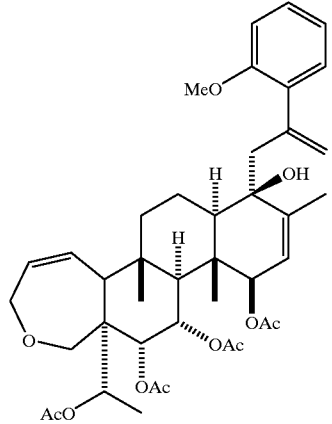

Step A: Prepration 2-(2'-methoxyphenyl)prop-2enyltrimethylsilane

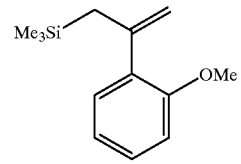

2 g of (2-bromoallyl)trimethylsilane (10.4 mmole) and 500 mg of tetrakis (triphenylphosphine) palladium (0.4 mmole) in 5 ml of benzene were heated to 80° C. until a homogenous solution resulted. The mixture was cooled to 40° C. and 10 ml of a 1M solution of phenylmagnesium chloride in THF were slowly added. The deep red reaction mixture was stirred at 40° C. for 12 h and poured into 20 ml of water. Extraction with ethyl acetate, washing of the combined organic layers with aqueous sodium chloride then drying over MgSO$_4$ gave an oil which was purified by silica gel chromatography with 19:1 hexanes-ethyl acetate to afford the title compound as a yellow oil.

$^1$H NMR (CDCl$_3$) δ 0.12 (s, 9H, SiMe$_3$), 2.10 (s, 2H, CH$_2$), 3.86 (s, 3H, OMe), 4.90 (s, 1H, =CH$_2$), 4.97 (s, 1H, =CH$_2$), 6.82–6.98 (m, 2H, ar-H), 7.18–7.25 (m, 2H, ar-H).

Step B: Preparation [5-S-5aa,5aa,7aa,8a,8b,11b,11ab,11ba,12a,13a,13aa]-13a-(1-R-acetoxyethyl)-8-hydroxy-8-(2-(2-methoxyphenyl)prop-2-enyl)-11,12,13-triacetoxy-5b,9,11a-trimethyl-1,3,5a,5b,6,-7,7a,8,11,11a,11b,12,13,13a-tetradec-ahydrophenanthro[2,1-c]oxepin

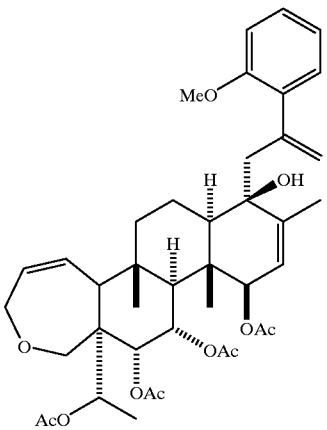

The title compound was prepared by the procedure described in Example 66.

$^1$H NMR (CDCl$_3$) δ 0.43 (m, 1H, C18-H), 2.79 and 2.96 (AB, 2H, J=13.5 Hz, CH$_2$), 3.67 and 3.72 (AB, 2H, J=12.5 Hz, C24-H), 3.87 (s, 3H, OMe), 4.15 and 4.34 (AB, 2H, J=17.5 Hz, C3-H), 4.82 (brs, 1H, =CH$_2$), 4.95 (brs, 1H, =CH$_2$), 6.89 (d, 1H, J=8.5 Hz, ar-H), 6.97 (dd, 1H, J$_1$=J$_2$= 7.5 Hz, ar-H), 7.14 (dd, 1H, J$_1$=1.5 Hz, J$_2$=7.0 Hz, ar-H), 7.27 (m, 1H, ar-H); Mass Spectrum (APCI): m/e 740 (M+NH$_4$).

EXAMPLE 73

[5-S-5aα,5aα,7aα,8α,8β,11β,11aβ,11bα,12α,13α,13aα]-13a-(1-R-acetoxyethyl)-8-hydroxy-8-(2-(2-ethylmercaptophenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin

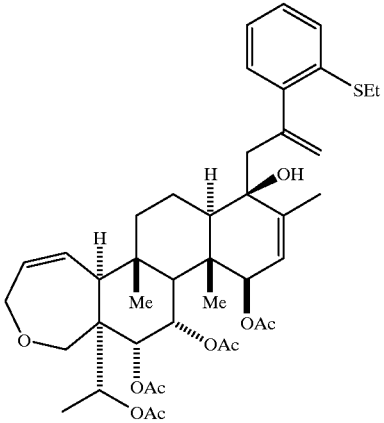

Step A: Preparation 1-ethylmercapto-2-bromobenzene

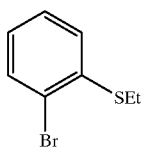

To a suspension of 1.00 g (5.3 mmol) of 2-bromobenzenethiol and 1.47 g (10.6 mmol) of potassium carbonate in 15 ml of N,N-dimethylformamide was added 1.65 g (10.6 mmol) of iodoethane at 0° C. The reaction mixture was stirred at 55–60° C. for 12 h and was poured into 200 ml of ether. It was washed with water (20 ml×3), dried over MgSO$_4$ and concentrated to afford 1-ethylsulfanyl-2-bromobenzene as a colorless oil.

Step B: Preparation of [2-(2-ethylmercaptophenyl)allyl trimethylsilane

A solution of the Grignard reagent of 1-ethylmercapto-2-bromobenzene in tetrahydrofuran was prepared in the following way: 1.50 g (6.9 mmol) of 1-ethylmercapto-2-bromobenzene were added to 218 mg (9.0 mmol) of magnesium in 8 ml of anhydrous tetrahydrofuran at room temperature under N$_2$ and It was heated at reflux for 1 h. Meanwhile, a solution of 1.20 g (6.2 mmol) of (2-bromoallyl)-trimethylsilane and 358 mg (0.31 mmol) of tetrakis(triphenylphosphine)-palladium in 6 ml of dry benzene was stirred at 80° C. under N$_2$ for 30 min. Then it was cooled to 50° C. and to it was added the Grignard reagent described above. The reaction mixture was stirred at 40° C. for 3 h and was poured into 100 ml of ether. It was washed with water (20 ml×2), dried over MgSO$_4$ and concentrated. The residue was purified by silica gel chromatography with hexane to give [2-(2-ethylmercaptophenyl)allyl trimethylsilane as a colorless oil.

Step C: Preparation of [5-S-5aα,5aα,7aα,8α,8β,11β,11aβ,11bα,12α,13α,13aα]-13a-(1-R-acetoxyethyl)-8-hydroxy-8-(2-(2-ethylmercaptophenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin

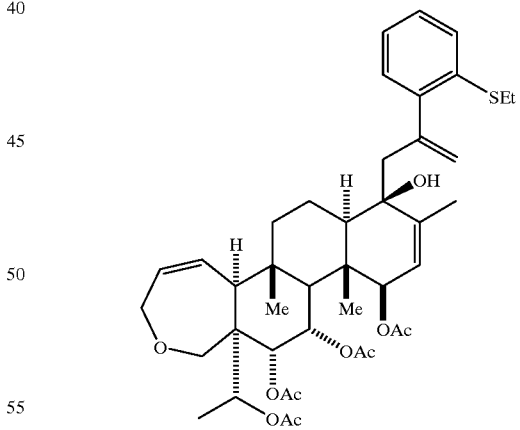

To a solution of 40 mg (0.070 mmol) of [5-S-5aα,5aα,7aα,11β,11aβ,11bα,12α,13α,13aα]-13a-(1-R-acetoxyethyl)-8-oxo-11,12,13-triacetoxy-5b,9,11a-trimethyl-1,3,5a,5b,6,7,7a,8,11,11a,11b,12,13,13a-tetradecahydrophenanthro[2,1-c]oxepin in 5 ml of dichloromethane was added 0.6 ml (0.21 mmol) of titanium (IV) chloride (1.0M) at −78° C. under N$_2$. After 5 min. 349 mg (1.39 mmol) of 2-(2-ethylmercaptophenyl)-allyltrimethylsilane was added. The mixture was warmed slowly to −15° C. and stirred at −15° C. for 3 h. Then it was poured into 100 ml of ether, washed with water (15 ml×2), dried over MgSO$_4$ and concentrated. The residue was purified by HPLC (waters RCM,υ porosil 10 mm×10 cm) using a mixture of 3.6:8 (5:4:1 hexane/methyl tert-butyl ether/acetonitrile:hexane) to afford the title compound as a white solid.

$^1$H NMR (CDCl$_3$) δ 1.38 (t, 3H, J=7 Hz), 1.69 (s, 3H), 2.96 (q, 2H, J=7 Hz), 4.94 (s, 1H), 4.99 (s, 1H), 7.09–7.14 (m, 2H), 7.23–7.26 (m, 2H); Mass Spectrum (CI, NH$_4$OAc): m/e 771 (M+NH$_4$)

EXAMPLE 74

[5-S-5aα,5aα,7aα,8α,8β,11β,11bβ,11bα,12α,13α,13aα]-13a-(1-R-acetoxyethyl)-8-hydroxy-8-(2-(2-ethylphenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin

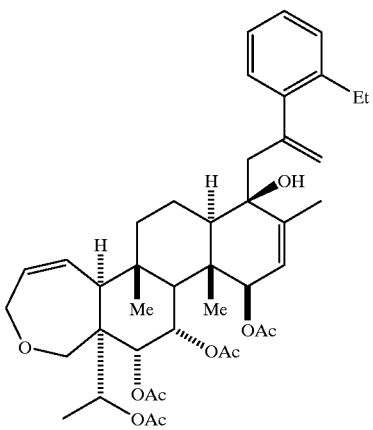

The title compound was prepared according to the procedures described in the previous example (Example 73).

$^1$H NMR (CDCl$_3$) δ 7.23–7.27 (m, 2H), 7.16 (t, 1H, J=7.4 Hz), 7.09 (d, 1H, J=7.6 Hz), 5.27 (s, 1H), 5.07 (s, 1H), 5.05 (s, 1H), 4.89 (s, 1H), 2.85 (d, 1H, J=6.2 Hz), 2.70 (d, 1H, J=6.2 Hz), 2.67 (q, 2H, J=7.8 Hz), 1.67 (s, 3H), 1.27 (t, 3H, J=7.5 Hz); Mass Spectrum (APCI): m/e 738 (M+NH$_4$)

EXAMPLE 75

[5-S-5aα,5aα,7aα,8α,8β,11β,11aβ,11bα,12α,13α,13aα]-13a-(1-R-acetoxyethyl)-8-hydroxy-8-(2-(2-methylmercaptophenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin

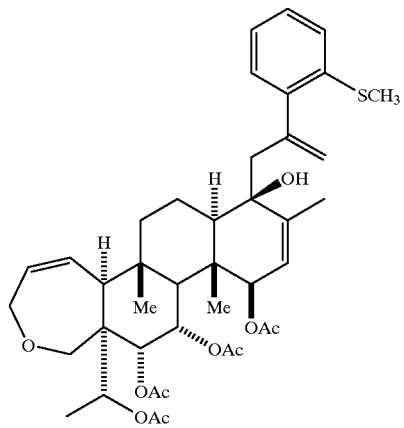

The title compound was prepared according to the procedures described in the previous example (Example 73).

$^1$H NMR (CDCl$_3$) δ 7.21–7.25 (m, 2H), 7.09–7.12 (m, 2H), 5.34 (s, 1H), 5.19 (s, 1H), 5.00 (s, 1H), 4.96 (s, 1H), 3.70 (d, 1H, J=12.0 Hz), 3.64 (d, 1H, J=12.0 Hz), 2.52 (s, 3H), 1.69 (s, 3H); Mass Spectrum (APCI): m/e 756 (M+NH$_4$)

EXAMPLES 76 AND 77

[5-S-5aα,5aα,7aα,8α,8β, 11β,11aβ,11bα,12α,13α,13aα]-13a-(1-R-acetoxyethyl)-8-hydroxy-8-(2-(2-methylsulfinylphenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin (2 isomers at S)

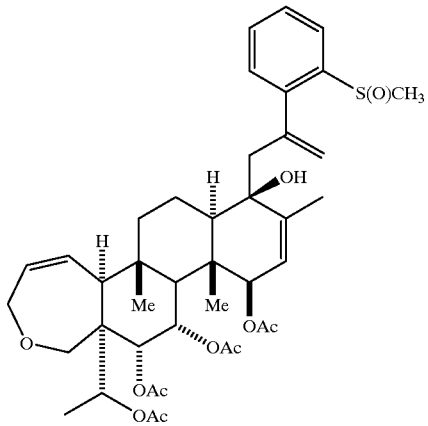

EXAMPLE 78

[5-S-5aα,5aα,7aα,8α,8β,11β,11aβ,11bα,12α,13α,13aα]-13a-(1-R-acetoxyethyl)-8-hydroxy-8-(2-(2-methylsulfonylphenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin

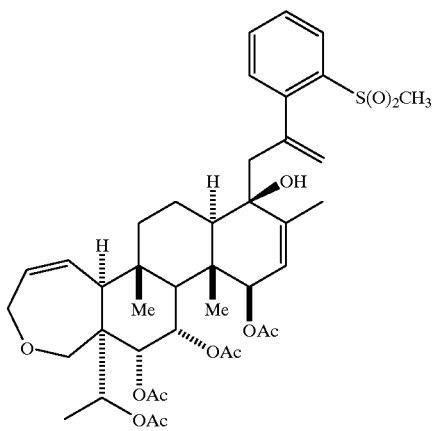

To a solution of [5-S-5aα,5aα,7aα,8α,8β,11β,11aβ,11bα, 12α,13α,13aα]-13a-(1-R-acetoxyethyl)-8-hydroxy-8-(2-(2-methylmercaptophenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin (11.0 mg, 0.015 mmol) in 2 ml of CHCl₃ was added MCPBA (0.021 mmol, 0.2 M in CH₂Cl₂) at −78° C. After 1.8 h it was poured into ether and washed with NaHCO₃ (2×), dried with MgSO₄, filtered through silica gel. The crude mixture was purified with HPLC to afford 3.7 mg, and 1.8 mg of the methylsulfinyl isomers (Examples 76 and 77) and 2.2 mg of the sulfone (Example 78).

Spectra data for Example 76: $^1$H NMR (CDCl₃) δ 8.07 (d, 2H, J=7.8 Hz), 7.71 (t, 1H, J=7.3 Hz), 7.58 (t, 1H, J=7.0 Hz), 7.23 (d, 1H, J=7.3 Hz), 5.37 (s, 1H), 5.15 (s, 1H), 5.12 (s, 1H), 4.69 (s, 1H), 2.66 (s, 3H), 1.83 (s, 3H); Mass Spectrum (APCI): m/e 772 (M+NH₄)

Spectra data for Example 77: $^1$H NMR (CDCl₃) δ 8.03 (d, 2H, J=7.8 Hz), 7.55 (t, 1H, J=7.3 Hz), 7.47 (t, 1H, J=7.37 Hz), 7.21 (d, 1H, J=7.5 Hz), 5.39 (s, 1H), 5.18 (s, 1H), 4.99 (s, 1H), 4.82 (s, 1H), 2.71 (s, 3H); Mass Spectrum (APCI): m/e 772 (M+NH₄)

Spectra data for Example 78: $^1$H NMR (CDCl₃) δ 8.09 (d, 1H, J=7.7 Hz), 7.75 (bs, 2H), 7.30 (d, 1H, J=8.7 Hz), 3.07 (s, 3H); Mass Spectrum (APCI): m/e 788 (M+NH₄)

EXAMPLE 79

[5-S-5aα,5aα,7aα,8α,8β,11β,11aβ,11bα,12α,13α,13aα]-13a-(1-R-acetoxyethyl)-8-hydroxy-8-(2-(2-ethylmercaptophenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin-3-one

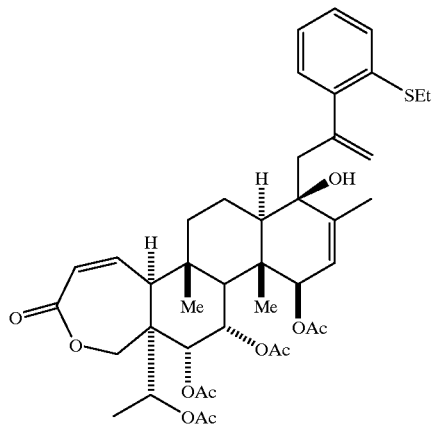

The title compound was prepared according to procedures described in Example 73, except that [5-S-5aα,5aα,7aα, 11β,11aβ,11aβ,12α,13α,13aα]-13a-(1-R-acetoxyethyl)-8-oxo-11,12,13-triacetoxy-5b,9,11a-trimethyl-1,3,5a,5b,6,7, 7a,8,11,11a,11b,12,13,13a,tetradecahydrophenanthro[2,1-c]oxepin-3-one was used as the substrate.

$^1$H NMR (CDCl₃) δ 1.38 (t, 3H, J=7 Hz), 1.69 (s,3H), 2.96 (q, 2H, J=7 Hz), 4.94 (s, 1H), 4.99 (s, 1H), 7.10–7.15 (m, 2H), 7.23–7.28 (m, 2H); Mass Spectrum (CI, NH₄OAc): m/e 785 (M+NH₄)

EXAMPLE 80

[5-S-5aα,5aα,7aα,8α,8β,11β,11aβ,11bα,12α,13α,13aα]-13a-(1-R-acetoxyethyl)-8-hydroxy-8-(2-(2-n-butylmercaptophenyl)prop-2-enyl)-11,12,13-triacetoxy-5b, 9,11a-trimethyl-1,3,5a,5b,6,7,7a,8,11,11a,11b,12,13,13a-tetradecahydrophenanthro[2,1-c]oxepin-3-one

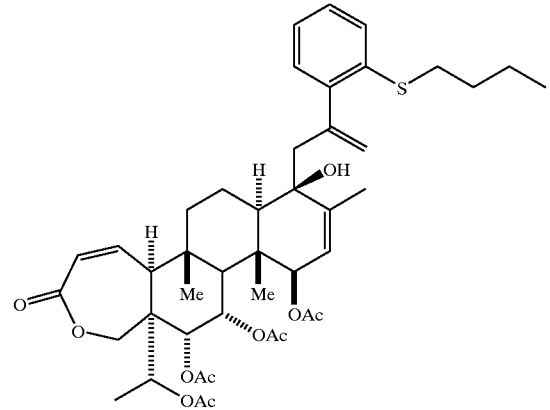

The title compound was prepared in the same manner as Example 73.

$^1$H NMR (CDCl₃) δ 1.38 (t, 3H, J=7 Hz), 0.94 (t, 3H, J=7 Hz), 1.45 (m, 2H), 1.65 (m, 2H), 1.69 (s,3H), 2.93 (m, 2H), 4.88 (s, 1H), 5.04 (s, 1H), 7.09–7.27 (m, 4H); Mass Spectrum (CI, NH₄OAc): m/e 812 (M+NH₄)

EXAMPLE 81

[5-S-5aα,5aα,7aα,8α,8β,11β,11aβ,11bα,12α,13α,13aα]-13a-(1-R-acetoxyethyl)-8-hydroxy-8-(2-(2-vinylphenyl) prop-2-enyl)-11,12,13-triacetoxy-5b,9,11a-trimethyl-1,3,5a, 5b,6,7,7a,8,11,11a,11b,12,13,13a-tetradecahydrophenanthro[2,1-c]oxepin-3-one

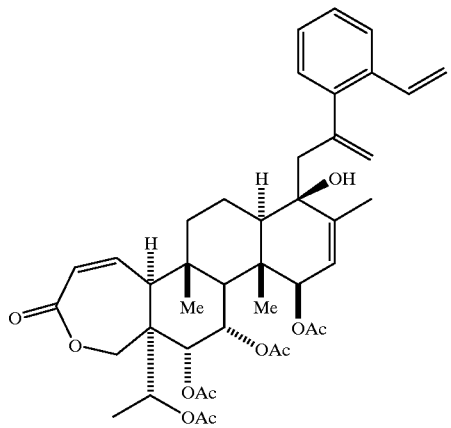

The title compound was prepared in the same manner as Example 73.

$^{1}$H NMR (CDCl$_{3}$) δ 7.63 (d, 1H, J=7.7 Hz), 7.22–7.25 (m, 2H), 7.15 (d, 1H, J=9.0 Hz), 6.96 (dd, 1H, J=17.6, 11.2 Hz), 5.86 (d, 1H, J=17.6 Hz), 5.35 (d, 1H, J=11.5 Hz), 5.33 (s, 1H), 5.08 (s, 1H), 5.06 (s, 1H), 4.91 (s, 1H) 1.74 (s, 3H); Mass Spectrum (APCI): m/e 750 (M+NH$_{4}$)

EXAMPLE 82

[5-S-5aα,5aα,7aα,8α,8β,11β,11aβ,11bα,12α,13α,13aα]-13a-(1-R-acetoxyethyl)-8-hydroxy-8-(2-(2-methoxy-5-methylphenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin-3-one

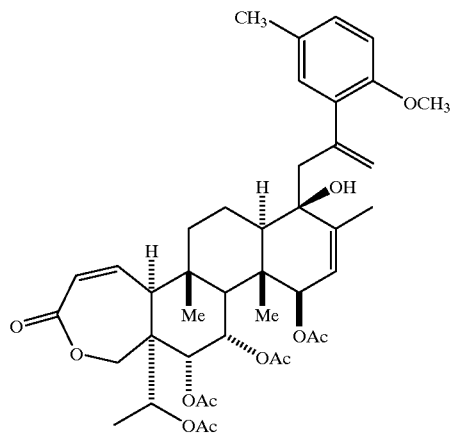

The title compound was prepared in the same manner as Example 73.

$^{1}$H NMR (CDCl$_{3}$) δ 7.03 (d, 1H, J=8.2 Hz), 6.90 (s, 1H), 6.74 (d, 1H, J=8.2 Hz), 5.12 (d, 2H, J=9.9 Hz), 4.86 (s, 1H)l, 3.78 (s, 3H), 1.87 (s, 3H); Mass Spectrum (CI, NH$_{4}$OAc): m/e 768 (M+NH$_{4}$)

EXAMPLE 83

[5-S-5aα,5aα,7aα,8α,8β,10α,11β,11aβ,11bα,12α,13α,13aα]-13a-(1-R-acetoxyethyl)-8-oxo-10-(2-(2-methoxy-5-methylphenyl)prop-2-enyl)-11,12,13-triacetoxy-5b,9,11a-trimethyl-1,3,5a,5b,6,7,7a,8,9,10,11,11a,11b,12,13,13a-hexadecahydrophenanthro[2,1-c]oxepin-3-one

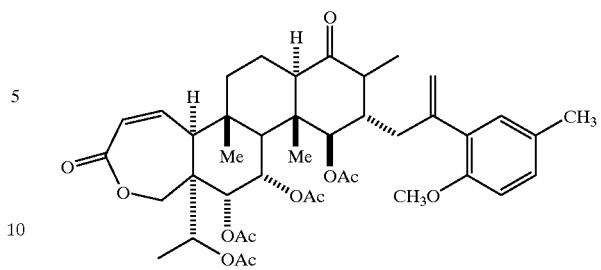

The title compound was obtained as a byproduct from Example 82.

$^{1}$H NMR (CDCl$_{3}$) δ 5.24 (s, 2H), 5.088 (s, 2H), 3.77 (s, 3H), 0.92 (d, 3H, 7.1 Hz); Mass Spectrum (CI, NH$_{4}$OAc): m/e 768 (M+NH$_{4}$)

EXAMPLE 84

[5-S-5aα,5aα,7aα,8α,8β,11β,11aβ,11bα,12α,13α,13aα]-13a-(1-R-acetoxyethyl)-8-hydroxy-8-(2-(S)-(2-ethylphenyl)propyl)-11,12,13-triacetoxy-5b,9,11a-trimethyl-1,3,5a,5b,6,7,7a,8,11,11a,11b,12,13,13a-tetradecahydrophenanthro[2,1-c]oxepin

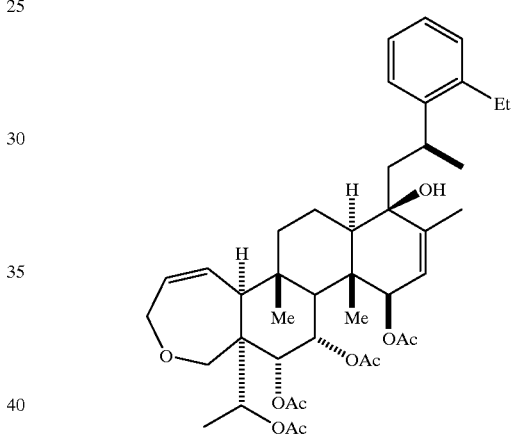

Step A: Preparation of 2-ethylphenylacetaldehyde

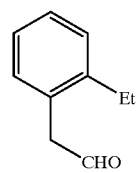

To a suspension of 8.53 g (350 mmoles) of magnesium in 270 mL in dry tetrahydrofuran was added 50 g (270 mmol) of 1-bromo-2-ethylbenzene. The temperature was maintained at 50° C. during addition, then was heated under reflux. After 1 h, the solution was cooled to −78° C. under N$_{2}$, and 54.42 g (324 mmoles) of allyl iodide was added dropwise. The mixture was allowed to warm to room temperature, stirred for an additional 2 h, then cooled to 0° C. The reaction was quenched by addtition of 2M HCl and 500 mL of ether and the layers were separated. The organic layer was washed with 30 mL of saturated NaHCO$_{3}$ solution and brine, dried over MgSO$_{4}$, and concentrated. The oily residue was filtered through silica gel with 20% ethyl acetate-hexane and the eluate was concentrated to afford the crude 1-allyl-2-ethylbenzene as a colorless oil.

A solution of 54.05 g of the crude 1-allyl-2-ethylbenzene in 500 mL of 1:1 $CH_2Cl_2$—$CH_3OH$ was cooled to −78° C. A stream of $O_3$ was bubbled through the solution for 3 h, until all of the starting material had disappeared. Then a stream of air was bubbled through the solution until the blue color had faded. A total of 25 mL of methyl sulfide was added and the solution was stirred at room temperature for 1 h. The solution was concentrated and dried under vacuum to afford the title compound as a colorless oil which was used directly in Part B.

Step B: Preprartion of (2-ethylphenyl)acetic acid

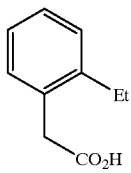

To a solution of the crude (2-ethylphenyl)acetaldehyde in 20 ml of EtOH was added a solution of 2.29 g (13.52 mmol) of $AgNO_3$ in 7.5 ml of water and a solution of 2.08 g (37.2 mmol) of KOH in 13 ml of water at 0° C. The reaction mixture was stirred at 0° C. for 2 h and was filtered to remove the solid. The filtrate was extracted with $CH_2Cl_2$ (20 ml×3) to remove impurity. The aqueous was acidified with 6N HCl to PH=1 and was extracted with $CH_2Cl_2$ (50 ml×3). The combined organic layers were dried $MgSO_4$ and concentrated to give 2-ethylphenylacetic acid.

Step C: Preparation of (R)-4-benzyl-3-[2-(2-ethylphenyl) ethyl]-oxazolidin-2-one

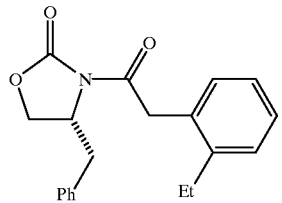

To a stirred solution of 2.16 g (13.2 mmol) of (2-ethylphenyl)-acetic acid and 1.6 g (15.84 mmol) of triethylamine in 55 ml of anhydrous tetrahydrofuran was added 1.67 g (13.86 mmol) trimethylacetyl chloride at −78° C. under $N_2$. After the resultant white suspension was stirred for 10 min. at −78° C. and 30 min. at 0° C., it was recooled to −78° C. and a −78° C. solution of metallated oxazolidinone prepared by the addition of 8.67 ml (13.86 mmol, 1.6 M in hexane) of n-butyllithium to a −78° C. solution of 2.46 g (13.86 mmol) of (R)-(+)-4-benzyl-2-oxazolidinone in 50 ml of anhydrous tetrahydrofuran was added via canula. The reaction mixture was stirred at 0° C. for an additional 30 min. and quenched by the addition of 50 ml of saturated aqueous ammonium chloride. The two layers were separated and the aqueous layer was extracted with $CH_2Cl_2$ (50 ml×3). The combined organic layers were dried over $MgSO_4$ and concentrated. The residue was purified by silica gel chromatography with 6:1 hexane/ethyl acetate to afford the title compound.

Step D: Preparation of (R),(R)-4-benzyl-3-[2-(2-ethylphenyl)-propyl]-oxazolidin-2-one

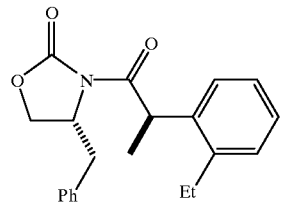

To a solution of 3.50 g (10.83 mmol) of (4R)-4-benzyl-3-[2-(2-ethyl-phenyl)-ethyl]-oxazolidin-2-one in 25 ml of tetrahydrofuran was added a solution of 13 ml (1.0 M, 13 mmol) of sodium bis(trimethylsilyl)amide at −78° C. under $N_2$. After the reaction mixture was stirred at −78° C. for 30 min., 3.29 g (9.92 mmol) of iodomethane was added at −78° C. The solution was stirred for 4 h and then quenched by the addition of 20 ml of aqueous saturated ammonium chloride solution. The two layers were separated and the aqueous was extracted with $CH_2Cl_2$ (50 ml×3). The combined organic layers were dried over $MgSO_4$ and concentrated. The residue was purified by silica gel chromatography with 500:35 hexane/ethyl acetate to afford the title compound. $[\alpha]^D=-146$ (c=1.55, $CHCl_3$).

Step E: Preparation of (R)-2-(2-ethyl-phenyl)-propanol

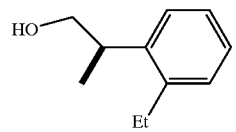

To a solution of 2.20 g (6.50 mmol) of (R),(R)-4-benzyl-3-[2-(2-ethyl-phenyl)-propyl]-oxazolidin-2-one in 20 ml of tetrahydrofuran was added 13 ml (1.0 M in THF, 13 mmol) of lithium aluminum hydride slowly at 0° C. The reaction mixture was stirred at 0° C. for 2 h and then quenched by addition of 5 ml of water. The mixture was acidified with 2N HCl to PH=1 and was extracted with $CH_2Cl_2$ (50 ml×3). The combined organic layers were dried $MgSO_4$ and concentrated. The residue was purified by silica gel chromatography with 10:1 hexane/ethyl acetate to afford the title compound. $[\alpha]^D=5.6$ (c=7.15, $CHCl_3$).

Step F: Preparation of (R)-2-(2-ethyl-phenyl)-propylbromide

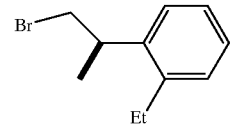

A solution of 0.93 g (6.20 mmol) of (R)-2-(2-ethyl-phenyl)-propanol in 40 ml of ether containing 2.60 g (9.92 mmol) of triphenylphosphine and 3.29 g (9.92 mmol) of carbon tetrabromide was stirred at room temperature for 3 h. It was filtered and concentrated. The residue was purified by silica gel chromatography with hexane to afford the title compound as a colorless oil. $[\alpha]^D=19.1$ (c=1.15, $CHCl_3$).

Step G: Preparation of [5-S-5aα,5aα,7aα,8α,8β,11β, 11aβ,11bα,12α,13α,13aα]-13a-(1-R-acetoxyethyl)-8-hydroxy-8-(2-(S)-(2-ethylphenyl)propyl)-11,12,13-triacetoxy-5b,9,11a-trimethyl-1,3,5a,5b,6,7,7a,8,11,11a, 11b,12,13,13a-tetradecahydrophenanthro[2,1-c]oxepin

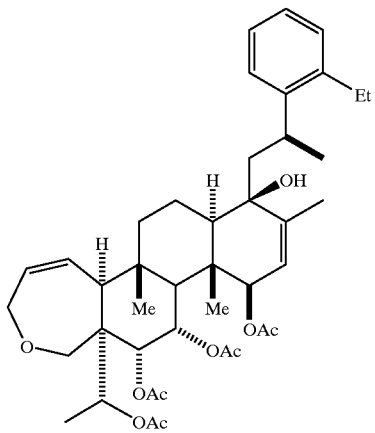

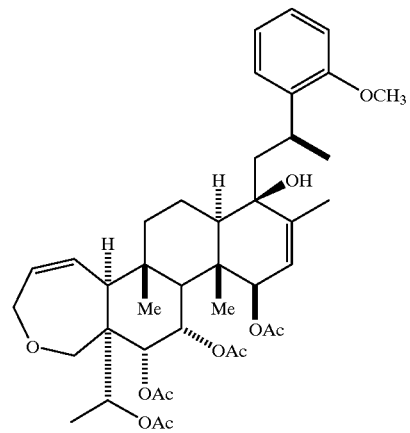

A solution of Grignard reagent (0.4M) of (R)-2-(2-ethylphenyl)-propylbromide in tetrahydrofuran was prepared in the following way: 283 mg (1.33 mmol) of (R)-2-(2-ethylphenyl)propylbromide was added into the mixture of 48.5 mg (1.99 mmol) of magnesium in 3.3 ml of anhydrous tetrehydrofuran at room temperature under $N_2$ and it was heated at reflux for 1 h.

To a solution of 20 mg (0.0348 mmol) of [5-S-5aα,5aα,7aα,11β,11aβ,11bα,12α,13α,13aα]-13a-(1-R-acetoxyethyl)-8-oxo-11,12,13-triacetoxy-5b,9,11a-trimethyl-1,3,5a,5b,6,7,7a,8,11,11a,11b,12,13,13a,tetradecahydrophenanthro[2,1-c]oxepin in 2 ml of tetrahydrofuran was added 0.53 ml (0.21 mmol) the 0.4M Grignard reagent. The mixture was stirred at room temperature under $N_2$ for 2 h. Then it was quenched with 5 drops of 0.1M phosphate buffer (pH=7). The residue was filtered through a plug of silica gel and was purified by HPLC (waters RCM,υ porosil 10 mm×10 cm) using a mixture of 3.6:8 (5:4:1 hexane/methyl tert-butyl ether/acetonitrile:hexane) to afford the title compound as a white solid.

$^1$H NMR (CDCl$_3$) δ 1.20 (d, 2H, J=7 Hz), 1.28 (t, 3H, J=7 Hz), 1.81 (s, 3H), 2.69–2.74 (m, 2H), 7.01–7.30 (m, 4H); Mass Spectrum (CI, NH$_4$OAc): m/e 740 (M+NH$_4$)

EXAMPLE 85

[5-S-5aα,5aα,7aα,8α,8β,11β,11aβ,11bα,12α,13α,13aα]-13a-(1-R-acetoxyethyl)-8-hydroxy-8-(2-(S)-(2-methoxyphenyl)propyl)-11,12,13-triacetoxy-5b,9,11a-trimethyl-1,3,5a,5b,6,7,7a,8,11,11a,11b,12,13,13a-tetradecahydrophenanthro[2,1-c]oxepin The title compound as a white solid was prepared according to procedures described in Example 84.

$^1$H NMR (CDCl$_3$) δ 1.18 (d, 2H, 7 Hz), 1.78 (s, 3H), 3.99 (s, 3H), 7.01–7.22 (m, 4H); Mass Spectrum (CI, NH$_4$OAc): m/e 742 (M+NH$_4$)

EXAMPLE 86

[5-S-5aα,5aα,7aα,8α,8β,11β,11aβ,11bα,12α,13α,13aα]-13a-(1-R-acetoxyethyl)-8-hydroxy-8-(2-methoxyphenyl)ethyl)-12,13-diacetoxy-5b,9,11a-trimethyl-1,3,5a,5b,6,7,7a,8,11,11a,11b,12,13,13a-tetradecahydrophenanthro[2,1-c]oxepin

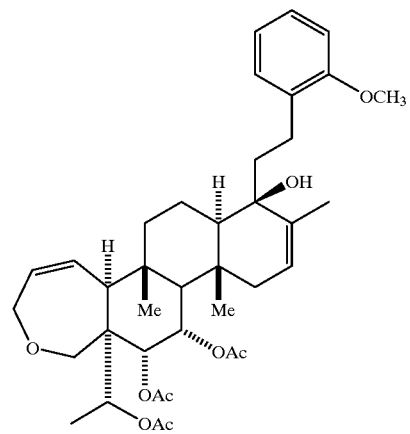

Step A: Preparation of [5-S-5aα,5aα,7aα,11β,11aβ,11bα,12α,13α,13aα]-13a-(1-R-acetoxyethyl)-8-oxo-12,13-diacetoxy-5b,9,11a-trimethyl-1,3,5a,5b,6,7,7a,8,11,11a,11b,12,13,13a,tetradecahydrophenanthro[2,1-c]oxepi

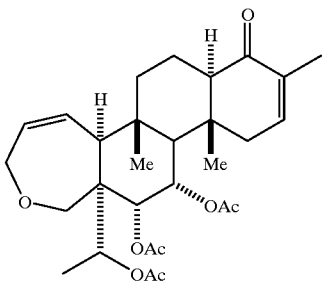

A solution of [5-S-5aα,5aα,7aα,11β,11aβ,11bα,12α,13α,13aα]-13a-(1-R-acetoxyethyl)-8-oxo-11,12,13-triacetoxy-5b,9,11a-trimethyl1,3,5a,5b,6,7,7a,8,11,11a,11b,12,13,13a,tetradecahydrophenanthro[2,1-c]oxepin (21.0 mg, 0.037 mmol) and zinc (110 mg, 1.68 mmol) in 5.0 ml of HOAc was heated at reflux for 14 h and HOAc was removed by vacuum. The residue was dissolved in CH$_2$Cl$_2$ and was filtered through a plug of silica gel. Upon removal of solvent, it was purified by HPLC to give the title compound.

$^1$H NMR (CDCl$_3$) δ 6.42 (bs, 1H), 5.72 (bs, 1H), 5.58–5.60 (m, 2H), 5.50 (d of d, 1H, J=5.0, 8.0 Hz), 5.39 (q, 1H, J=6.5 Hz), 4.33 (d, 1H, J=17 Hz), 4.18 (d, 1H, J=17 Hz), 3.70 (d, 1H, J=12 Hz), 3.65 (d, 1H, J=12 Hz), 2.08 (s, 3H), 2.06 (s, 3H), 2.03 (s, 3H), 1.76 (d, 3H, J=1.3 Hz), 1.22 (d, 3H, J=6.4 Hz), 1.11 (s, 3H), 0.95 (s, 3H); Mass Spectrum (APCI): m/e 534 (M+NH$_4$)

Step B: Preparation of [5-S-5aα,5aα,7aα,8α,8β,11β,11aβ,11bα,12α,13α,13aα]-13a-(1-R-acetoxyethyl)-8-hydroxy-8-(2-methoxyphenyl)ethyl)-12,13-diacetoxy-5b,9,11a-trimethyl-1,3,5a,5b,6,7,7a,8,11,11a,11b,12,13,13a-tetradecahydrophenanthro[2,1-c]oxepin

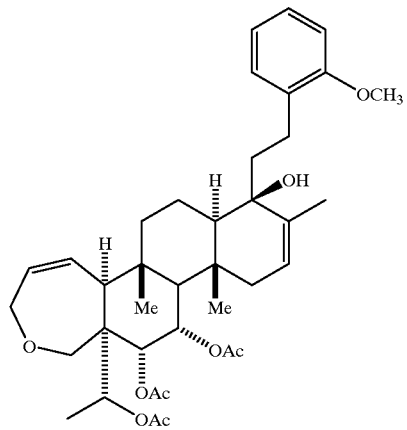

To a solution of [5-S-5aα,5aα,7aα,11β,11aβ,11bα,12α,13α,13aα]-13a-(1-R-acetoxyethyl)-8-oxo-12,13-diacetoxy-5b,9,11a-trimethyl-1,3,5a,5b,6,7,7a,8,11,11a,11b,12,13,13a-tetradecahydrophenanthro[2,1-c]oxepin (18.0 mg, 0.035 mmol) in 2.0 ml of THF at 0° C. was added 2-methoxy phenethyl magnesium bromide (0.31 mmol as a 0.4 M solution in THF). It was then warmed to rt for 100 minutes and was quenched with pH=7 buffer solution. The mixture was filtered through a plug of silica gel and purified with flash chromatography (EtOAc/hexane, 1:4) to give the title compound.

$^1$H NMR (CD$_2$Cl$_2$) δ 7.17 (t of d, 1H, J=1.5, 7.5 Hz), 7.12 (d of d, 1H, J=1.5, 7.5 Hz), 6.85–6.90 (m, 2H), 5.71 (bs, 1H), 5.62–5.66 (m, 1H), 5.76 (d, 1H, J=12 Hz), 5.48–5.51 (m, 2H), 5.37 (q, 1H, J=6.4 Hz), 4.35 (d, 1H, J=17 Hz), 4.36 (d, 1H, J=17 Hz), 3.83 (s, 3H), 3.70 (d, 1H, J=14.5 Hz), 3.68 (d, 1H, J=14.5 Hz), 2.06 (s, 3H), 1.99 (s, 3H), 1.80 (bs, 3H), 1.22 (d, 3H, J=6.4 Hz), 1.13 (s, 3H), 1.07 (s, 3H), Mass Spectrum (APCI): m/e 670 (M+NH$_4$).

EXAMPLE 87

[5-S-5aα,5aα,7aα,8α,8β,11β,11aβ,11bα,12α,13α,13aα]-13a-(1-R-acetoxyethyl)-8-hydroxy-8-(2-(2-ethylphenyl)prop-2-enyl)-11-hydroxy-12,13-diacetoxy-5b,9,11a-trimethyl-1,3,5a,5b,6,7,7a,8,11,11a,11b,12,13,13a-tetradecahydrophenanthro[2,1-c]oxepin

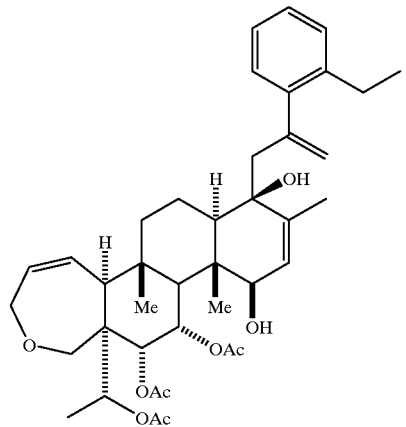

Step A: Preparation of [5-S-5aα,5aα,7aα,8α,8β,11β,11aβ,11bα,12α,13α,13aα]-13a-(1-R-hydroxyethyl)-8-hydroxy-8-(2-(2-ethylphenyl)prop-2-enyl)-11,12,13-trihydroxy-5b,9,11a-trimethyl-1,3,5a,5b,6,7,7a,8,11,11a,11b,12,13,13a-tetradecahydrophenanthro[2,1-c]oxepin

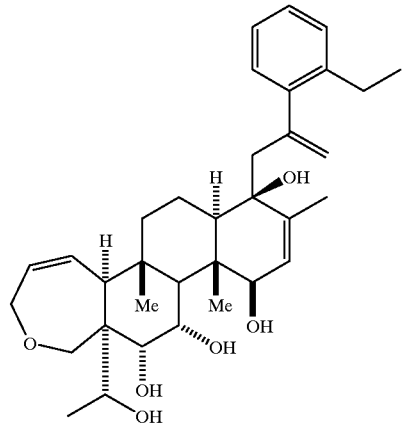

A solution of [5-S-5aα,5aα,7aα,8α,8β,11β,11aβ,11bα,12α,13α,13aα]-13a-(1-R-acetoxyethyl)-8-hydroxy-8-(2-(2-ethylphenyl)prop-2-enyl)-11,12,13-triacetoxy-5b,9,11a-trimethyl-1,3,5a,5b,6,7,7a,8,11,11a,11b,12,13,13a-tetradecahydro-phenanthro[2,1-c]oxepin (114 mg, 0.16 mmol) in 15 ml of MeOH was added K$_2$CO$_3$ (17.0 mg, 0.12 mmol) and the solution was heated at reflux for 24 h. MeOH was removed and the residue was dissolved in EtOAc and filtered through silica gel. Solvent was removed to give the title compound.

Step B: Preparation of [5-S-5aα,5aα,7aα,8α,8β,11β,11aβ,11bα,12α,13α,13aα]-13a-(1-R-acetoxyethyl)-8- hydroxy-8-(2-(2-ethylphenyl)prop-2-enyl)-11-hydroxy-12,13-diacetoxy-5b,9,11a-trimethyl-1,3,5a,5b,6,7,7a,8,11,11a,11b,12,13,13a-tetradecahydrophenanthro[2,1-c]oxepin

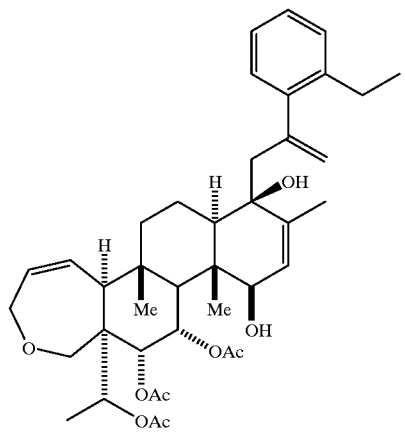

To a solution of the compound from Step A (39.7 mg, 0.072 mmol) in 6.0 ml of THF was added DMAP (2.0 mg, 0.016 mmol), pyridine (0.60 ml, 7.4 mmol) and acetic anhydride (0.30 ml, 3.2 mmol) at rt. After it was stirred for 20 h, the solution was removed of solvents, redissolved in $CH_2Cl_2$ and filtered through a plug of silica gel. Upon removal of $CH_2Cl_2$, the residue was purified by HPLC to give the title compound.

$^1$H NMR (CDCl$_3$) δ 7.22–7.28 (m, 2H), 7.14 (t, 1H, J=8.0 Hz), 7.06 (d, 1H, J=7.5 Hz), 2.79 (d, 1H, J=4.5 Hz), 5.60 (dd, 1H, J=4.5, 6.0 Hz), 5.45–5.52 (m, 2 H), 5.37 (q, 1H, J=6.5 Hz), 5.26 (s, 1H), 5.12 (s, 1H), 5.06 (bs, 1H), 4.35 (d, 1H, J=17.5 Hz), 4.14 (d, 1H, J=17.5 Hz), 7.75 (d, 1H, J=10 Hz), 3.70 (d, 1H, J=12 Hz), 3.65 (d, 1H, J=12 Hz), 2.83 (d, 1H, J=14.1 Hz), 2.71 (d, 1H, J=14.1 Hz), 2.66 (q, 2H, J=7.3 Hz), 2.14 (s, 3H), 2.05 (s, 3H), 2.00 (s, 3H), 1.26 (t, 1H, J=7.5 Hz); Mass Spectrum (APCI): m/e 696 (M+NH$_4$).

EXAMPLE 88

[5-S-5aα,5aα,7aα,8α,8β,11β,11aβ,11bα,12α,13α,13aα]-13a-(1-R-acetoxyethyl)-8-hydroxy-8-(2-(2-ethylphenyl)prop-2-enyl)-11,13-diacetoxy-12-hydroxy-5b,9,11a-trimethyl-1,3,5a,5b,6,7,7a,8,11,11a,11b,12,13,13a-tetradecahydrophenanthro[2,1-c]oxepin

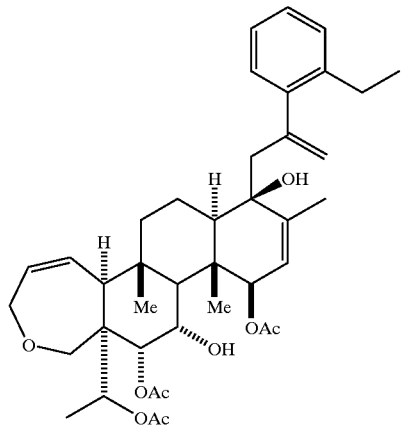

The title compound was isolated as a byproduct in the reaction that produced Example 87.

$^1$H NMR (CDCl$_3$) δ 7.25 (t, 1H, J=7.5 Hz), 7.21 (d, 1H, J=7.5 Hz), 7.16 (t, 1H, J=7.5 Hz), 7.11 (d, 1H, J=7.0 Hz), 5.71 (d, 1H, J=4.5 Hz), 5.45–5.51 (m, 2 H), 5.31 (q, 1H, J=6.0 Hz), 5.17 (s, 1H), 5.06 (bs, 1H), 5.04 (s, 1H), 4.36 (d, 1H, J=17 Hz), 4.31 (bs, 1H), 4.16 (d, 1H, J=17 Hz), 3.60 (d, 1H, J=12.5 Hz), 3.56 (d, 1H, J=12.5 Hz), 2.85 (d, 1H, J=15 Hz), 2.73 (d, 1H, J=15 Hz), 2.69 (q, 2 H, J=7.3 Hz), 2.11 (s, 3H), 2.13 (s, 3H), 1.95 (s, 3H) 1.25 (t, 3H, J=7.3 Hz); Mass Spectrum (APCI): m/e 696 (M+NH$_4$).

EXAMPLE 89

[5-S-5aα,5aα,7aα,8α,8β,11β,11aβ,11bα,12α,13α,13aα]-13a-(1-R-acetoxyethyl)-8-hydroxy-8-(2-(2-ethylphenyl)prop-2-enyl)-11-oxo-12,13-diacetoxy-5b,9,11a-trimethyl-1,3,5a,5b,6,7,7a,8,11,11a,11b,12,13,13a-tetradecahydrophenanthro[2,1-c]oxepin

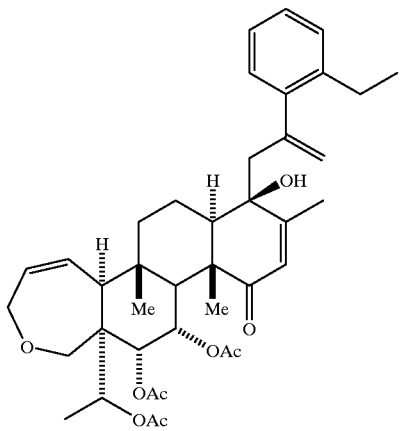

To a solution of [5-S-5aα,5aα,7aα,8α,8β,11β,11aβ,11bα,12α,13α,13aα]-13a-(1-R-acetoxyethyl)-8-hydroxy-8-(2-(2-ethylphenyl)prop-2-enyl)-11-hydroxy-12,13-diacetoxy-5b,9,11a-trimethyl-1,3,5a,5b,6,7,7a,8,11,11a,11b,12,13,13a-tetradecahydrophenanthro[2,1-c]oxepin (8.9 mg, 0.013 mmol) in 5 ml of acetone was added 2 drops of 8 N Jones reagent at 0° C. After 30 minutes, it was poured into ether and was washed with brine, dried with Na$_2$SO$_4$. The residue was purified with HPLC to give the title compound.

$^1$H NMR (CDCl$_3$) δ 7.23–7.25 (m, 2H), 7.11–7.14 (m, 1H), 6.96 (d, 1H, J=7.8 Hz), 5.75 (bd, 1H, J=11.4 Hz), 5.60 (s, 1H), 5.50–5.60 (m, 1H), 5.47 (q, 1H, J=6.7 Hz), 5.30 (bs, 1H), 5.24 (s, 1H), 5.20 (bd, 1H, J=9.2 Hz), 5.07 (s, 1H), 4.23 (bs, 2H), 3.91 (d, 1H, J=13 Hz), 3.71 (d, 1 H, J=13 Hz), 2.90 (d, 1H, J=13.9 Hz), 2.78 (d, 1H, J=13.9 Hz), 2.57–2.63 (m, 2H), 2.26 (s, 2H), 2.03 (s, 3H), 1.92 (s, 3H), 1.68 (s, 3H); Mass Spectrum (APCI): m/e 694 (M+NH$_4$).

EXAMPLE 90

[5-S-5aα,5aα,7aα,8α,8β,11β,11aβ,11bα,12α,13α,13aα]-13a-(1-R-acetoxyethyl)-8-hydroxy-8-allyl-11,12,13-triacetoxy-5b,9,11a-trimethyl-1,3,5a,5b,6,7,7a,8,11,11a,11b,12,13,13a-tetradecahydrophenanthro[2,1-c]oxepin-3-one

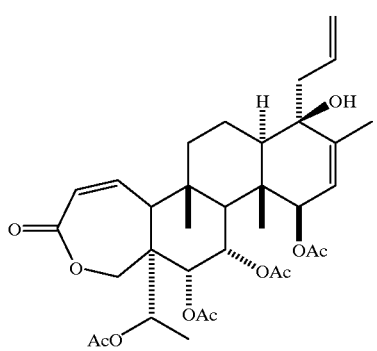

To a solution of 100 mg of [5-S-5aα,5aα,7aα,11β,11aβ, 11bα,12α,13α,13aα]-13a-(1-R-acetoxyethyl)-8-oxo-11,12, 13-triacetoxy-5b,9,11a-trimethyl-1,3,5a,5b,6,7,7a,8,11,11a, 11b,12,13,13a, tetradecahydrophenanthro[2,1-c]oxepin-3-one (0.17 mmole) in 5 ml of CH$_2$Cl$_2$ was added 1.0 ml of a 1M solution of TiCl$_4$ (6 eq.) in CH$_2$Cl$_2$ at −20° C. The resulting yellow suspension was stirred for 20 minutes then 0.3 ml of allyl trimethylsilane (10 eq.) was added. Stirring was continued at −20° C. until TLC control showed no remaining starting material (approx. 65 h). 20 ml of water were then added, and the mixture was extracted with ethyl acetate and the organic phase was washed with aqueous sodium chloride then was dried over MgSO$_4$ and concentrated. The residue was first filtered through a plug of silica gel and then purified by HPLC (Waters RCM, Prep Nova-Pak HR Silica, 2 25×100 mm cartridges) to afford the title compound as an oil.

$^1$H NMR (CDCl$_3$) δ 4.16 and 4.48 (AB, 2H, J=12.5 Hz, C24-H), 5.10 (dd, 1H, J$_1$=1.5 Hz, J$_2$=25.0 Hz, =CH$_2$), 5.13 (d, 1H, J=19.5 Hz, =CH$_2$), 5.42 (m, 1H, CH=CH$_2$), 6.08 (d, 1H, J=12.0 Hz, C2-H), 6.38 (dd, 1H, J$_1$=9.0 Hz, J$_2$=12.0 Hz, C1-H); $^{13}$C NMR (CDCl$_3$) δ 118.4, 123.0, 125.1, 133.0, 137.3, 142.7, 168.9, 169.7, 169.9, 170.3, 172.1; Mass Spectrum (APCI): m/e 648 (M+NH$_4$).

The following two examples were obtained as a minor products from the previous example:

EXAMPLE 91
[5-S-5aα,5aα,7aα,10α,11β,11aβ,11bα,12α,13α,13aα]-13a-(1-R-acetoxyethyl)-8-oxo-10α-(3-trimethylsilylpropyl)-11, 12,13-triacetoxy-5b,9β,11a-trimethyl-1,3,5a,5b,6,7,7a,8,9, 10,11,11a,11b,12,13,13a-hexadecahydrophenanthro[2,1-c] oxepin-3-one

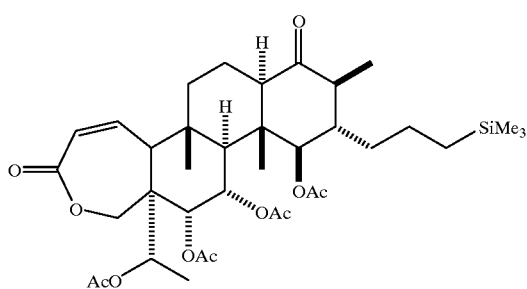

$^1$H NMR (CDCl$_3$) δ −0.02 (s, 9H, SiMe$_3$), 4.13 and 4.46 (AB, 2H, J=12.5 Hz, C24-H), 6.08 (d, 1H, J=12.5 Hz, C2-H), 6.38 (dd, 1H, J$_1$=8.5 Hz, J$_2$=12.0 Hz, C1-H); $^{13}$C NMR (CDCl$_3$) δ −3.2 (SiMe$_3$), 66.2 (C24), 123.3 (C2), 142.4 (C1), 168.6, 169.4, 170.1, 170.7, 171.7, 215.6 (C18); Mass Spectrum (APCI): m/e 720 (M+NH$_4$).

EXAMPLE 92
[5-S-5aα,5aα,7aα,10α,11β,11aβ,11bα,12α,13α,13aα]-13a-(1-R-acetoxyethyl)-8-oxo-10α-(allyl)-11,12,13-triacetoxy-5b,9β,11a-trimethyl-1,3,5a,5b,6,7,7a,8,9,10,11,11a,11b,12, 13,13a-hexadecahydrophenanthro[2,1-c]oxepin-3-one

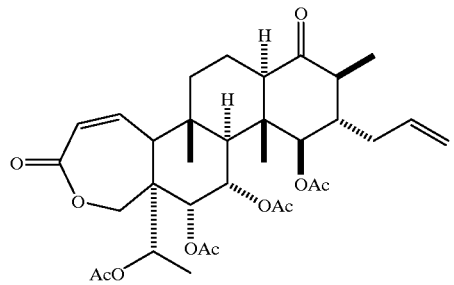

$^1$H NMR (CDCl$_3$) δ 4.16 and 4.45 (AB, 2H, J=12.5 Hz, C24-H), 5.11 (d, 1H, J=14.0 Hz, =CH$_2$), 5.18 (d, 1H, J=10.0 Hz, =CH$_2$), 5.93 (m, 1H, CH=CH$_2$), 6.07 (d, 1H, J=12.5 Hz, C2-H), 6.37 (dd, J$_1$=9.0 Hz, J$_2$=12.0 Hz, C1-H); Mass Spectrum (APCI): m/e 648 (M+NH$_4$).

EXAMPLE 93
[5-S-5aa,5aa,7aa,8a,8b,10a,11b,11ab,11ba,12a,13a,13aa]-13a-(1-R-acetoxyethyl)-8-oxo-10-cyano-11,12,13-triacetoxy-5b,9,11a-trimethyl-1,3,5a,5b,6,7,7a,8,9,10,11, 11a,11b,12,13,13a-hexadecahydrophenanthro[2,1-c]oxepin

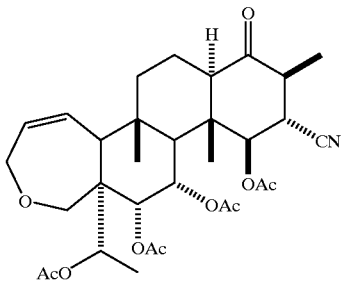

To a solution of 65 mg of [5-S-5aα,5aα,7aα,11β,11aβ, 11bα,12α,13α,13aα]-13a-(1-R-acetoxyethyl)-8-oxo-11,12, 13-triacetoxy-5b,9,11a-trimethyl1,3,5a,5b,6,7,7a,8,11,11a, 11b,12,13,13a,tetradecahydrophenanthro[2,1-c]oxepin (0.113 mmole) in 0.5 ml of toluene were added 2 ml of a 1M solution of diethylaluminum cyanide in toluene. The mixture was warmed to 40° C. for 3 h and poured into 10 ml of cold 1N hydrochloric acid. 20 ml of dichloromethane was added and the layers were separated. The organic phase was washed with aqueous sodium chloride then was dried over MgSO$_4$ and concentrated. The residue was first filtered through a plug of silica gel and then purified by HPLC (Waters RCM, Prep Nova-Pak HR Silica, 2 25×100 mm cartridges) to afford the title compound as a white solid.

$^1$H NMR (CDCl$_3$) δ 1.22 (d, 3H, J=6.4 Hz, C17-CH$_3$), 2.77 (dq, 1H, J$_1$=10.9 Hz, J$_2$=6.4 Hz, C17-H), 2.84 (dd, 1H, J$_1$=10.9 Hz, J$_2$=7.9 Hz, C16-H), 3.64 and 3.69 (AB, 2H, J=12.0 Hz, C24-H), 4.16 and 4.35 (AB, 2H, J=17.5 Hz, C3-H); $^{13}$C NMR (CDCl$_3$) δ 118.5 (CN), 126.3, 128.7, 170.2, 170.3, 171.0, 171.1, 206.5; Mass Spectrum (APCI): m/e 619 (M+NH$_4$).

EXAMPLE 94
[5-S-5aα,5aα,7aα,8α,8β,11β,11aβ,11bα,12α,13α,13aα]-13a-(1-R-acetoxyethyl)-8-hydroxy-8-allyl-11,12,13- triacetoxy-5b,9,11a-trimethyl-1,3,5a,5b,6,7,7a,8,11,11a, 11b,12,13,13a-tetradecahydrophenanthro[2,1-c]oxepin

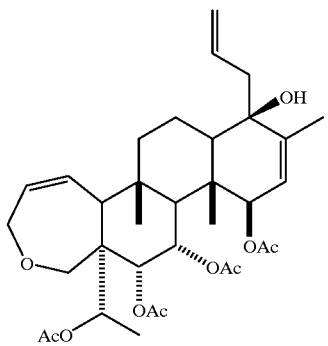

The title compound was prepared according to procedures described in Example 90 using [5-S-5aα,5aα,7aα,11β,11aβ, 11bα,12α,13α,13aα]-13a-(1-R-acetoxyethyl)-8-oxo-11,12, 13-triacetoxy-5b,9,11a-trimethyl1,3,5a,5b,6,7,7a,8,11,11a, 11b,12,13,13a, tetradecahydrophenanthro[2,1-c]oxepin.

$^1$H NMR (CDCl$_3$) δ 3.63–3.67 (AB 2H, J=12 Hz), δ 4.11–4.30 (AB, 2H, J=17 Hz ); δ 5.0–5.1 (m, 2H, CH=C H+b 2); δ 5.36 (m, 1H, CH=CH2); $^{13}$C NMR (CDCl$_3$) δ 172.2, 170.6, 170.5, 170.4, 137.4, 133.3, 128.1, 126.7, 118.5 Mass Spectrum (APCI): m/e 634(M+NH$_4$).

EXAMPLE 95

[5-S-5aα,5aα,7aα,8α,8β,11β,11aβ,11bα,12α,13α,13aα]-13a-(1-R-acetoxyethyl)-8-hydroxy-8-(2-oxoethyl)-11,12, 13-triacetoxy-5b,9,11a-trimethyl-1,3,5a,5b,6,7,7a,8,11,11a, 11b,12,13,13a-tetradecahydrophenanthro[2,1-c]oxepin

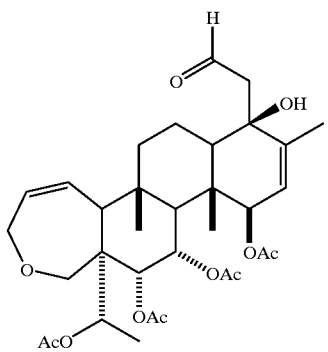

To a solution of 50 mg (0.080 mmole) of [5-S-5aα,5aα, 7aα,8α,8β,11β,11aβ,11bα,12α,13α,13aα]-13a-(1-R-acetoxyethyl)-8-hydroxy-8-allyl-11,12,13-triacetoxy-5b,9, 11a-trimethyl-1,3,5a,5b,6,7,7a,8,11,11a,11b,12,13,13a-tetradecahydrophenanthro[2,1-c]oxepin in 5 mL THF was added 18 mg (0.16 mmole) N methyl morpholine N oxide and 2.0 mg (0.008 mmole) of osmium tetroxide. The solution was stirred at room temperature for 4 hours, then was treated with a saturated NaHSO$_3$ solution and stirred for 30 minutes. The reaction was partitioned between 50 ml ether and 10 ml water and separated. The aqueous was washed with 20 ml ether and the organic layers were combined and washed with brine and dryed over Na$_2$SO$_4$ and evaporated. The residue was then dissolved in 4 ml THF and treated with 35 mg (0.16 mmole) of sodium periodate in 2 ml of water and allowed to stir 3 hrs. The reaction was concentrated under reduced pressure and partitioned between 40 ml ether and 20 ml water. The layers were separated and dryed over MgSO$_4$ and evaporated. The residue was first filtered through a plug of silica gel and then purified by HPLC (Prep NovaPAK HR Silica, 10 mm×10 cm) using a mixture of 1:1 (5:4:1 hexane-methyl tert-butyl ether-acetonitrile:hexane) to afford the title compound as a white solid.

$^1$H NMR (CDCl$_3$) δ 9.63 (t, 1H, 2.5 Hz); 2.18 (d, 2H, J=2.5 Hz); Mass Spectrum (CI, NH$_4$OAc): m/e 636 (M+NH$_4$).

EXAMPLE 96

[5-S-5aα,5aα,7aα,8α,8β,11β,11aβ,11bα,12α,13α,13aα]-13a-(1-R-acetoxyethyl)-8-hydroxy-8-(2-(2-methoxyphenyl)-2-hydroxyethyl)-11,12,13-triacetoxy-5b,9, 11a-trimethyl-1,3,5a,5b,6,7,7a,8,11,11a,11b,12,13,13a-tetradecahydrophenanthro[2,1-c]oxepin

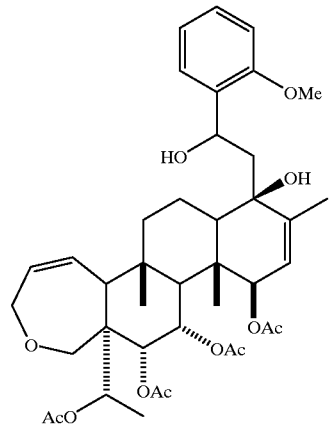

To a solution of 112 mg (0.6 mmole) of 2-bromoanisole in 3 ml THF at −78° C. was added 352 μl (0.6 mmole) of 1.7M t-BuLi in pentane. The solution was allowed to stir for 45 minutes and the treated with 190 mg (0.6 mmole) of CuI and stirred for 30 minutes. A solution of 126 mg (0.20 mmole) of [5-S-5aα,5aα,7aα,8α,8β,11β,11aβ,11bα,12α, 13α,13aα]-13a-(1-R-acetoxyethyl)-8-hydroxy-8-(2-oxoethyl)-11,12,13-triacetoxy-5b,9,11a-trimethyl-1,3,5a,5b, 6,7,7a,8,11,11a,11b,12,13,13a-tetradecahydrophenanthro[2, 1-c]oxepin in 2 mL THF was then added and allowed to stir at −20° C. for 4 hours. The reaction was quenched with NH$_4$Cl(sat) and was partitioned between 20 ml ether and 5 ml water and separated. The aqueous was washed with 10 ml ether and the organic layers were combined and washed with brine and dryed over Na$_2$SO$_4$ and evaporated. The residue was first filtered through a plug of silica gel and then purified by HPLC (Waters RCM, Prep NovaPAK HR Silica, 10 mm×10 cm) using a mixture of 1:1 (5:4:1 hexane-methyl tert-butyl ether-acetonitrile:hexane) to afford the title compound as a white solid.

$^1$H NMR (CDCl$_3$) δ 3.78, 3.92 (s, 3H), 5.22 (m, 1H), 6.80–7.00 (m, 3H), 7.25 (m, 1H); Mass Spectrum (CI, NH$_4$OAc): m/e 762 (M+NH$_4$).

EXAMPLE 97

[5-S-5aα,5aα,7aα,8α,8β,11β,11aβ,11bα,12α,13α,13aα]-13a-(1-R-acetoxyethyl)-8-hydroxy-8-(2-(pyrid-3-yl)-2-hydroxyethyl)-11,12,13-triacetoxy-5b,9,11a-trimethyl-1,3, 5a,5b,6,7,7a,8,11,11a,11b,12,13,13a-tetradecahydrophenanthro[2,1-c]oxepin

103

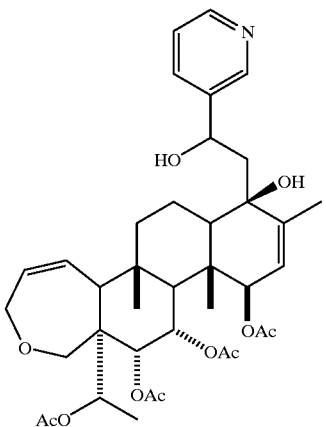

104

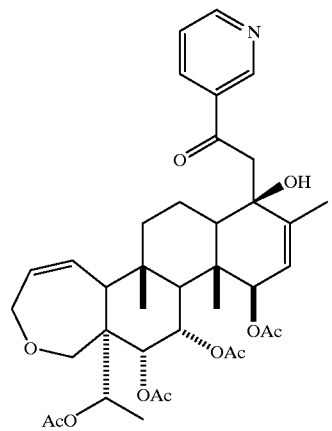

To a solution of 158 mg (0.6 mmole) of 3-bromopyridine in 3 ml THF at −78° C. was added 352 μl (0.6 mmole) of 1.7M BuLi in pentane. The solution was allowed to stir for 1 hour and then treated with 600 μl (0.6 mmole) of 1M TiCl(i-PrO)₃ in hexane and stirred for 30 minutes. A solution of 126 mg (0.20 mmole) of [5-S 5aα,5aα,7aα,8α,8β,11β,11aβ,11bα,12α,13α,13aα]-13a-(1-R-acetoxyethyl)-8-hydroxy-8-(2-oxoethyl)- 11,12,13-triacetoxy-5b,9,11a-trimethyl-1,3,5a,5b,6,7,7a,8,11,11a,11b,12,13,13a-tetradecahydrophenanthro[2,1-c]oxepin in 2 mL THF was then added and allowed to stir at −20° C. for 6 hours. The reaction was quenched with NH₄Cl(sat) and was partitioned between 20 ml ether and 5 ml water and separated. The aqueous was washed with 10 ml ether and the organic layers were combined and washed with brine and dryed over Na₂SO₄ and evaporated. The residue was first filtered through a plug of silica gel and then purified by HPLC (Waters RCM, Prep NovaPAK HR Silica, 10 mm×10 cm) using a mixture of 3:1 (5:4:1 hexane-methyl tert-butyl ether-acetonitrile:hexane) to afford the title compound as a white solid.

¹H NMR (CDCl₃) δ 4.53 (m, 1H), 7.25 (m, 2H), 7.83 (m, 1H): Mass Spectrum (CI, NH₄OAc): m/e 733(M+NH₄).

EXAMPLE 98

[5-S-5aα,5aα,7aα,8α,8β,11β,11aβ,11bα,12α,13α,13aα]-13a-(1-R-acetoxyethyl)-8-hydroxy-8-(2-(pyrid-3-yl)-2-oxoethyl)-11,12,13-triacetoxy-5b,9,11a-trimethyl-1,3,5a,5b,6,7,7a,8,11,11a,11b,12,13,13a-tetradecahydrophenanthro[2,1-c]oxepin To a solution of 10.0 mg (0.020 mmole) of [5-S-5aα,5aα,7aα,8α,8β,11β,11aβ,11bα,12α,13α,13aα]-13a-(1-R-acetoxyethyl)-8-hydroxy-8-(2-(pyrid-3-yl)-2-hydroxyethyl)-11,12,13-triacetoxy-5b,9,11a-trimethyl-1,3,5a,5b,6,7,7a,8,11,11a,11b,12,13,13a-tetradecahydrophenanthro[2,1-c]oxepin in 5 mL dichloromethane was added powdered sieves and 10 mg (0.05 mmole) pyridinium chlorochromate. The solution was stirred at room temperature for 4 hours, then added 10 ml ether and filtered. The filtrate was partitioned with water and separated. The aqueous was washed with 10 ml ether and the organic layers were combined and washed with brine and dryed over Na₂SO₄ and evaporated. The residue was first filtered through a plug of silica gel and then purified by HPLC (Waters RCM, m Porosil, 10 mm×10 cm) using a mixture of 2:1 (5:4:1 hexane-methyl tert-butyl ether-acetonitrile:hexane) to afford the title compound as a white solid.

¹H NMR (CDCl₃) δ 3.23–3.35 (d of d, 18 Hz, 2H), 7.52 (s,broad 1H), 8.28 (s,broad 1H), 8.84 (s,broad 1H), 9.19 (s,broad 1H); Mass Spectrum (CI, NH₄OAc): m/e 760 (M+NH₄).

What is claimed is:

1. A compound of structural Formula I:

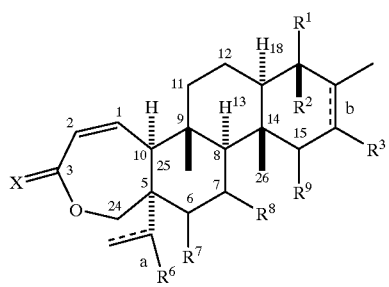

I or a pharmaceutically acceptable salt, crystal form, or hydrate, wherein:

X is: O, S, NH, or a and b are independently a single bond or a double bond, and represented by = in the structure above;

n is: 0, 1 or 2;

r is: 0 or 1;

s is: 0 or 1;

$R^1$ is:
- (1) H,
- (2) =O, when $R^2$ is absent,
- (3) $(C_1-C_{10})$-alkyl, wherein alkyl is unsubstituted or substituted with one or two of the substituents selected from the group consisting of:
  - (a) halo, wherein halo is fluoro, chloro, bromo, or iodo,
  - (b) hydroxy,
  - (c) oxo,
  - (d) $(C_1-C_6)$-alkyloxy,
  - (e) $(C_1-C_6)$—$S(O)_n$—,
  - (f) aryl-$(C_1-C_6)$-alkyloxy,
  - (g) cyano,
  - (h) nitro,
  - (i) vinyl,
  - (j) $NR^4R^5$,
  - (k) $NR^4COC_1-C_6$-alkyl,
  - (l) CHO,
  - (m) $CO_2H$,
  - (n) $COC_1-C_6$-alkyl,
  - (o) $CO_2C_1-C_6$-alkyl,
  - (p) $CONR^4R^5$,
  - (q) aryl, wherein aryl is defined as phenyl or naphthyl, unsubstituted or substituted with one, two or three of the substituents selected from the group consisting of:
    - (a') halo, as defined above,
    - (b') hydroxy,
    - (c') $(C_1-C_6)$-alkyl,
    - (d') (C1–C4)-perfluoroalkyl,
    - (e') $(C_1-C_6)$-alkenyl,
    - (f') $(C_1-C_6)$-alkynyl,
    - (g') $(C_1-C_6)$-alkyloxy,
    - (h') $(C_1-C_6)$-alkyl-$S(O)_n$—,
    - (i') phenyl,
    - (j') phenoxy,
    - (k') cyano,
    - (l') nitro,
    - (m') $CO_2H$,
    - (n') $COC_1-C_6$-alkyl,
    - (o') $CO_2C_1-C_6$-alkyl,
    - (p') $CONR^4R^5$,
    - (q') $NR^4R^5$,
    - (r') $NR^4COC_1-C_6$-alkyl,
    - (s') $(C_1-C_6)$-alkenyloxy, and
    - (t') benzyloxy;
  - (r) heteroaryl, wherein heteroaryl is defined as an unsubstituted, monosubstituted, or disubstituted five or six membered aromatic heterocycle containing from 1 to 3 heteroatoms selected from the group consisting of O, N and S and wherein the substituents are selected from the group consisting of:
    - (a') halo, as defined above,
    - (b') hydroxy,
    - (c') $(C_1-C_6)$-alkyl,
    - (d') (C1–C4)-perfluoroalkyl,
    - (e') $(C_1-C_6)$-alkenyl,
    - (f') $(C_1-C_6)$-alkynyl,
    - (g') $(C_1-C_6)$-alkyloxy,
    - (h') $(C_1-C_6)$-alkyl-$S(O)_n$—,
    - (i') phenyl,
    - (j') phenoxy,
    - (k') cyano,
    - (l') nitro,
    - (m') $CO_2H$,
    - (n') $COC_1-C_6$-alkyl,
    - (o') $CO_2C_1-C_6$-alkyl,
    - (p') $CONR^4R^5$,
    - (q') $NR^4R^5$,
    - (r') $NR^4COC_1-C_6$-alkyl,
    - (s') fused benzo, and
    - (t') fused pyridyl group,
  - (s) heterocyclyl, wherein heterocyclyl is defined as a cyclic, non-aromatic substituent containing from 1 to 3 heteroatoms selected from the group consisting of O, N, and S, said heterocycle being unsubstituted or substituted with one, two or three substituents selected from the group consisting of
    - (a') halo, as defined above,
    - (b') hydroxy,
    - (c') $(C_1-C_6)$-alkyl,
    - (d') (C1–C4)-perfluoroalkyl,
    - (e') $(C_1-C_6)$-alkenyl,
    - (f') $(C_1-C_6)$-alkynyl,
    - (g') $(C_1-C_6)$-alkyloxy,
    - (h') $(C_1-C_6)$-alkyl-$S(O)_n$—,
    - (i') phenyl,
    - (j') phenoxy,
    - (k') cyano,
    - (l') nitro,
    - (m') $CO_2H$,
    - (n') $COC_1-C_6$-alkyl,
    - (o') $CO_2C_1-C_6$-alkyl,
    - (p') $CONR^4R^5$,
    - (q') $NR^4R^5$,
    - (r') NR4COC1-C6-alkyl,
    - (s') oxo,
    - (t') fused benzo, and
    - (u') fused pyridyl group;
- (4) $(C_2-C_{10})$-alkenyl, wherein alkenyl is unsubstituted or substituted with one or two of the substituents selected from the group consisting of:
  - (a) halo, wherein halo is fluoro, chloro, bromo, or iodo,
  - (b) hydroxy,
  - (c) oxo,
  - (d) $(C_1-C_6)$-alkyloxy,
  - (e) $(C_1-C_6)$—$S(O)_n$—,
  - (f) phenyl-$(C_1-C_6)$-alkyloxy,
  - (g) cyano,
  - (h) nitro,
  - (i) vinyl,
  - (j) $NR^4R^5$,
  - (k) $NR^4COC_1-C_6$-alkyl,
  - (l) CHO,
  - (m) $CO_2H$,
  - (n) $COC_1-C_6$-alkyl,
  - (o) $CO_2C_1-C_6$-alkyl,
  - (p) $CONR^4R^5$,
  - (q) aryl, wherein aryl is as defined above,
  - (r) heteroaryl, wherein heteroaryl is as defined above, and
  - (s) heterocycle, wherein the heterocycle is as defined above,
- (5) $(C_2-C_{10})$-alkynyl, wherein alkynyl is unsubstituted or substituted with one or two of the substituents selected from the group consisting of:
  - (a) halo, wherein halo is fluoro, chloro, bromo, or iodo,
  - (b) hydroxy,
  - (c) oxo, (d) $(C_1-C_6)$-alkyloxy,
(e) $(C_1-C_6)-S(O)_n-$,
(f) phenyl-$(C_1-C_6)$-alkyloxy,
(g) cyano,
(h) nitro,
(i) vinyl,
(j) $NR^4R^5$,
(k) $NR^4COC_1-C_6$-alkyl,
(l) CHO,
(m) $CO_2H$,
(n) $COC_1-C_6$-alkyl,
(o) $CO_2C_1-C_6$-alkyl,
(p) $CONR^4R^5$,
(q) aryl, wherein aryl is as defined above,
(r) heteroaryl, wherein heteroaryl is as defined above,
(s) heterocycle, wherein heterocycle is as defined above, and
(t) $Si(R^4)_3$,
(6) an exo-methylene group, when $R^2$ is absent, or
(7) aryl, wherein aryl is defined as phenyl or naphthyl, unsubstituted or substituted with one, two or three of the substituents selected from the group consisting of:
(a') halo, as defined above,
(b') hydroxy,
(c') $(C_1-C_6)$-alkyl,
(d') (C1–C4)-perfluoroalkyl,
(e') $(C_1-C_6)$-alkenyl,
(f') $(C_1-C_6)$-alkynyl,
(g') $(C_1-C_6)$-alkyloxy,
(h') $(C_1-C_6)$-alkyl-$S(O)_n-$,
(i') phenyl,
(j') phenoxy,
(k') cyano,
(l') nitro,
(m') $CO_2H$,
(n') $COC_1-C_6$-alkyl,
(o') $CO_2C_1-C_6$-alkyl,
(p') $CONR^4R^5$,
(q') $NR^4R^5$,
(r') $NR^4COC_1-C_6$-alkyl,
(s') $(C_1-C_6)$-alkenyloxy, and
(t') benzyloxy;
$R^2$ is:
(1) H,
(2) absent when $R^1$ is oxo,
(3) absent when $R^1$ is an exo-methylene group, or
(4) OH,
$R^3$ is:
(1) H, or
(2) $(C_1-C_{10})$-alkyl, wherein alkyl is unsubstituted or substituted with one or two of the substituents selected from the group consisting of:
(a) halo, wherein halo is fluoro, chloro, bromo, iodo,
(b) hydroxy,
(c) oxo,
(d) $(C_1-C_6)$-alkyloxy,
(e) $(C_1-C_6)-S(O)_n-$,
(f) aryl-$(C_1-C_6)$-alkyloxy,
(g) cyano,
(h) nitro,
(i) vinyl,
(j) $NR^4R^5$,
(k) $NR^4COC_1-C_6$-alkyl,
(l) CHO,
(m) $CO_2H$,
(n) $COC_1-C_6$-alkyl,
(o) $CO_2C_1-C_6$-alkyl,
(p) $CONR^4R^5$,
(q) aryl, wherein aryl is defined as phenyl or naphthyl, unsubstituted or substituted with one, two or three of the substituents selected from the group consisting of:
(a') halo, as defined above,
(b') hydroxy,
(c') $(C_1-C_6)$-alkyl,
(d') (C1–C4)-perfluoroalkyl,
(e') $(C_1-C_6)$-alkenyl,
(f') $(C_1-C_6)$-alkynyl,
(g') $(C_1-C_6)$-alkyloxy,
(h') $(C_1-C_6)$-alkyl-$S(O)_n-$,
(i') phenyl,
(j') phenoxy,
(k') cyano,
(l') nitro,
(m') $CO_2H$,
(n') $COC_1-C_6$-alkyl,
(o') $CO_2C_1-C_6$-alkyl,
(p') $CONR^4R^5$,
(q') $NR^4R^5$, and
(r') $NR^4COC_1-C_6$-alkyl,
(r) heteroaryl, wherein heteroaryl is defined as an unsubstituted, monosubstituted, or disubstituted five or six membered aromatic heterocycle containing from 1 to 3 heteroatoms selected from the group consisting of O, N and S and wherein the substituents are members selected from the group consisting of:
(a') halo, as defined above,
(b') hydroxy,
(c') $(C_1-C_6)$-alkyl,
(d') (C1–C4)-perfluoroalkyl,
(e') $(C_1-C_6)$-alkenyl,
(f') $(C_1-C_6)$-alkynyl,
(g') $(C_1-C_6)$-alkyloxy,
(h') $(C_1-C_6)$-alkyl-$S(O)_n-$,
(i') phenyl,
(j') phenoxy,
(k') cyano,
(l') nitro,
(m') $CO_2H$,
(n') $COC_1-C_6$-alkyl,
(o') $CO_2C_1-C_6$-alkyl,
(p') $CONR^4R^5$,
(q') $NR^4R^5$,
(r') $NR^4COC_1-C_6$-alkyl, and
(s') fused benzo or pyridyl group,
(s) heterocyclyl, wherein heterocyclyl is defined as a cyclic, non-aromatic substituent containing from 1 to 3 heteroatoms selected from the group consisting of O, N, and S, said heterocycle being unsubstituted or substituted with one, two or three substituents selected from the group consisting of:
(a') halo, as defined above,
(b') hydroxy,
(c') $(C_1-C_6)$-alkyl,
(d') (C1–C4)-perfluoroalkyl,
(e') $(C_1-C_6)$-alkenyl,
(f') $(C_1-C_6)$-alkynyl,
(g') $(C_1-C_6)$-alkyloxy,
(h') $(C_1-C_6)$-alkyl-$S(O)_n-$,
(i') phenyl,
(j') phenoxy,
(k') cyano,
(l') nitro, (m') $CO_2H$,
(n') $COC_1-C_6$-alkyl,
(o') $CO_2C_1-C_6$-alkyl,
(p') $CONR^4R^5$,
(q') $NR^4R^5$,
(r') $NR4COC1-C6$-alkyl,
(s') oxo,
(t') fused benzo, and
(u') fused pyridyl group;
(t) $Si(R^4)_3$,
(3) $(C_2-C_{10})$-alkenyl, wherein alkenyl is unsubstituted or substituted with one or two of the substituents selected from the group consisting of:
(a) halo, wherein halo is fluoro, chloro, bromo, or iodo,
(b) hydroxy,
(c) oxo,
(d) $(C_1-C_6)$-alkyloxy,
(e) $(C_1-C_6)-S(O)_n-$,
(f) phenyl-$(C_1-C_6)$-alkyloxy,
(g) cyano,
(h) nitro,
(i) vinyl,
(j) $NR^4R^5$,
(k) $NR^4COC_1-C_6$-alkyl,
(l) CHO,
(m) $CO_2H$,
(n) $COC_1-C_6$-alkyl,
(o) $CO_2C_1-C_6$-alkyl,
(p) $CONR^4R^5$,
(q) aryl, wherein aryl is as defined above,
(r) heteroaryl, wherein heteroaryl is as defined above, and
(s) heterocyclyl, wherein heterocyclyl is as defined above;
(4) $(C_2-C_{10})$-alkynyl, wherein alkynyl is unsubstituted or substituted with one or two of the substituents selected from the group consisting of:
(a) halo, wherein halo is fluoro, chloro, bromo, or iodo,
(b) hydroxy,
(c) oxo,
(d) $(C_1-C_6)$-alkyloxy,
(e) $(C_1-C_6)-S(O)_n-$,
(f) phenyl-$(C_1-C_6)$-alkyloxy,
(g) cyano,
(h) nitro,
(i) vinyl,
(j) $NR^4R^5$,
(k) $NR^4COC_1-C_6$-alkyl,
(l) CHO,
(m) $CO_2H$,
(n) $COC_1-C_6$-alkyl,
(o) $CO_2C_1-C_6$-alkyl,
(p) $CONR^4R^5$,
(q) aryl, wherein aryl is as defined above,
(r) heteroaryl, wherein heteroaryl is as defined above, and
(s) heterocyclyl, wherein heterocyclyl is as defined above; or
(5) cyano;
$R^4$ and $R^5$ are independently:
(1) hydrogen,
(2) C1–C6 alkyl, or
(3) aryl, wherein aryl is defined above,
$R^6$ is:
(1) hydrogen,
(2) oxo and a is a single bond,
(3) $O[(C=O)O_r]_sR^{11}$,
(4) $O[(C=O)O_r]_s$aryl, aryl as defined above,
(5) $O[(C=O)O_r]_s$heteroaryl, heteroaryl as defined above,
(6) $OC(=O)NR^{11}R^{12}$,
(7) $NR^{11}R^{12}$, or
(8) absent when a is a double bond;
$R^7$, $R^8$ and $R^9$ are independently selected from the group consisting of:
(1) hydrogen,
(2) oxo,
(3) $O[(C=O)O_r]_sR^{11}$,
(4) $O[(C=O)O_r]_s$aryl, aryl as defined above,
(5) $O[(C=O)O_r]_s$heteroaryl, heteroaryl as defined above,
(6) $OC(=O) NR^{11}R^{12}$, and
(7) $NR^{11}R^{12}$; and
$R^{10}$, $R^{11}$ and $R^{12}$ are independently chosen from the group consisting of:
(1) H, and
(2) $(C_1-C_6)$-alkyl, wherein alkyl is unsubstituted or substituted with one, two or three substituents selected from the group consisting of: Br, Cl, F, I, $(C_1-C_6)$-alkoxy, vinyl, cyano, oxo, nitro, hydroxy, CHO, $CO_2H$, $COC_1-C_6$-alkyl, $CO_2C_1-C_6$-alkyl, $CONR^4R^5$, $NR^4R^5$, $NR^4COC_1-C_6$-alkyl, aryl, wherein aryl is defined as phenyl or naphthyl, unsubstituted or substituted with one, two or three substituents selected from the group consisting of: Br, Cl, F, I, $(C_1-C_6)$-alkoxy, phenyl, phenoxy, cyano, oxo, nitro, hydroxy, CHO, $CO_2H$, $COC_1-C_6$-alkyl, $CO_2C_1-C_6$-alkyl, $CONR^4R^5$, $NR^4R^5$, $NR^4COC_1-C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, $(C_1-C_6)$-alkoxy, cyano, oxo, nitro, hydroxy, CHO, $CO_2H$, $COC_1-C_6$-alkyl, $CO_2C_1-C_6$-alkyl, CON $R^4R^5$, $NR^4R^5$, $NR^4COC_1-C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring.

2. The compound of structural Formula I as recited in claim 1, wherein X is defined as O.

3. The compound of structural Formula I as recited in claim 1, wherein.

4. The compound of structural Formula I as recited in claim 1, wherein:
X is: O or
$R^3$ is:
(1) H, or
(2) $(C_1-C_3)$-alkyl, wherein alkyl is unsubstituted or substituted with one or two of the substituents selected from the group consisting of:
(a) halo, wherein halo is fluoro, chloro, bromo, iodo,
(b) hydroxy,
(c) oxo,
(d) $(C_1-C_6)$-alkyloxy,
(e) $(C_1-C_6)-S(O)_n-$,
(f) aryl-$(C_1-C_6)$-alkyloxy,
(g) cyano, (h) nitro,
(i) vinyl,
(j) NR$^4$R$^5$,
(k) NR$^4$COC$_1$–C$_6$-alkyl,
(l) CHO,
(m) CO$_2$H,
(n) COC$_1$–C$_6$-alkyl,
(o) CO$_2$C$_1$–C$_6$-alkyl,
(p) CONR$^4$R$^5$,
(q) aryl, wherein aryl is defined as phenyl or naphthyl, unsubstituted or substituted with one, two or three of the substituents selected from the group consisting of:
 (a') halo, as defined above,
 (b') hydroxy,
 (c') (C$_1$–C$_6$)-alkyl,
 (d') (C1–C4)-perfluoroalkyl,
 (e') (C$_1$–C$_6$)-alkenyl,
 (f') (C$_1$–C$_6$)-alkynyl,
 (g') (C$_1$–C$_6$)-alkyloxy,
 (h') (C$_1$–C$_6$)-alkyl-S(O)$_n$—,
 (i') phenyl,
 (j') phenoxy,
 (k') cyano,
 (l') nitro,
 (m') CO$_2$H,
 (n') COC$_1$–C$_6$-alkyl,
 (o') CO$_2$C$_1$–C$_6$-alkyl,
 (p') CONR$^4$R$^5$,
 (q') NR$^4$R$^5$, and
 (r') NR$^4$COC$_1$–C$_6$-alkyl,
(r) Si(R$^4$)$_3$, (3) (C$_2$–C$_3$)-alkenyl, wherein alkenyl is unsubstituted or substituted with one or two of the substituents selected from the group consisting of:
 (a) halo, wherein halo is fluoro, chloro, bromo, or iodo,
 (b) hydroxy,
 (c) oxo,
 (d) (C$_1$–C$_6$)-alkyloxy,
 (e) (C$_1$–C$_6$)—S(O)$_n$—,
 (f) phenyl-(C$_1$–C$_6$)-alkyloxy,
 (g) cyano,
 (h) nitro,
 (i) vinyl,
 (j) NR$^4$R$^5$,
 (k) NR$^4$COC$_1$–C$_6$-alkyl,
 (l) CHO,
 (m) CO$_2$H,
 (n) COC$_1$–C$_6$-alkyl,
 (o) CO$_2$C$_1$–C$_6$-alkyl,
 (p) CONR$^4$R$^5$,
 (q) aryl, wherein aryl is as defined above,
 (r) heteroaryl, wherein heteroaryl is as defined above, and
 (s) heterocyclyl, wherein heterocyclyl is as defined above;

(4) (C$_2$–C$_3$)-alkynyl, wherein alkynyl is unsubstituted or substituted with one or two of the substituents selected from the group consisting of:
 (a) halo, wherein halo is fluoro, chloro, bromo, or iodo,
 (b) hydroxy,
 (c) oxo,
 (d) (C$_1$–C$_6$)-alkyloxy,
 (e) (C$_1$–C$_6$)—S(O)$_n$—,
 (f) phenyl-(C$_1$–C$_6$)-alkyloxy,
 (g) cyano,
 (h) nitro,
 (i) vinyl,
 (j) NR$^4$R$^5$,
 (k) NR$^4$COC$_1$–C$_6$-alkyl,
 (l) CHO,
 (m) CO$_2$H,
 (n) COC$_1$–C$_6$-alkyl,
 (o) CO$_2$C$_1$–C$_6$-alkyl,
 (p) CONR$^4$R$^5$,
 (q) aryl, wherein aryl is as defined above,
 (r) heteroaryl, wherein heteroaryl is as defined above, and
 (s) heterocyclyl, wherein heterocyclyl is as defined above; or (5) cyano;

R$^4$ and R$^5$ are independently:
 (1) hydrogen,
 (2) C$_1$–C$_3$ alkyl, or
 (3) phenyl, R$^6$ is:
 (1) hydrogen,
 (2) oxo and a is a single bond,
 (3) O(C=O)R$^{11}$, or
 (4) absent when a is a double bond;

R$^7$, R$^8$ and R$^9$ are independently selected from the group consisting of:
 (1) hydrogen,
 (2) oxo,
 (3) O(C=O)R$^{11}$; and R$^{10}$, R$^{11}$ and R$^{12}$ are independently chosen from the group consisting of:
 (1) H, and
 (2) (C$_1$–C3)-alkyl.

5. The compound of structural Formula I as recited in claim 1, wherein:
X is: O, or
R$^1$ is:
 (1) H,
 (2) =O, when R$^2$ is absent,
 (3) (C$_1$–C$_8$)-alkyl, wherein alkyl is unsubstituted or substituted with one or two of the substituents selected from the group consisting of:
  (a) halo, wherein halo is fluoro, chloro, bromo, or iodo,
  (b) hydroxy,
  (c) oxo,
  (d) (C$_1$–C$_3$)-alkyloxy,
  (e) CHO,
  (g) CO(C$_1$–C$_3$)-alkyl,
  (i) aryl, wherein aryl is defined as phenyl or naphthyl, unsubstituted or substituted with one, two or three of the substituents selected from the group consisting of:
   (a') halo, as defined above,
   (b') hydroxy,
   (c') (C$_1$–C$_6$)-alkyl,
   (d') (C1–C4)-perfluoroalkyl,
   (e') (C$_1$–C$_6$)-alkenyl,
   (f') (C$_1$–C$_6$)-alkynyl,
   (g') (C$_1$–C$_6$)-alkyloxy,
   (h') (C$_1$–C$_6$)-alkyl-S(O)$_n$—,
   (i') phenyl,
   (j') phenoxy,
   (k') cyano,
   (l') nitro,
   (m') CO$_2$H, (n') COC$_1$–C$_6$-alkyl,
(o') CO$_2$C$_1$–C$_6$-alkyl,
(p') CONR$^4$R$^5$,
(q') NR$^4$R$^5$,
(r') NR$^4$COC$_1$–C$_6$-alkyl,
(s') (C$_1$–C$_6$)-alkenyloxy, and
(t') benzyloxy;
(j) heteroaryl, wherein heteroaryl is defined as pyridyl or thienyl,
(4) (C$_2$–C$_6$)-alkenyl, wherein alkenyl is unsubstituted or substituted with aryl, wherein aryl is as defined above; and
(5) (C$_2$–C$_3$)-alkynyl, wherein alkynyl is unsubstituted or substituted with phenyl or Si(R$^4$)$_3$, or
(6) an exo-methylene group, when R$^2$ is absent;
R$^3$ is:
(1) H, or
(2) (C$_1$–C$_3$)-alkyl, wherein alkyl is unsubstituted or substituted with phenyl or Si(R$^4$)$_3$,
(3) (C$_2$–C$_3$)-alkenyl, wherein alkenyl is unsubstituted or substituted with aryl, wherein aryl is defined as phenyl or naphthyl, unsubstituted or substituted with one, two or three substituents selected from the group consisting of:
(a') halo, as defined above,
(b') hydroxy,
(c') (C$_1$–C$_6$)-alkyl,
(d') (C1–C4)-perfluoroalkyl,
(e') (C$_1$–C$_6$)-alkenyl,
(f') (C$_1$–C$_6$)-alkynyl,
(g') (C$_1$–C$_6$)-alkyloxy,
(h') (C$_1$–C$_6$)-alkyl-S(O)$_n$—,
(i') phenyl,
(j') phenoxy,
(k') cyano,
(l') nitro,
(m') CO$_2$H,
(n') COC$_1$–C$_6$-alkyl,
(o') CO$_2$C$_1$–C$_6$-alkyl,
(p') CONR$^4$R$^5$,
(q') NR$^4$R$^5$,
(r') NR$^4$COC$_1$–C$_6$-alkyl,
(s') (C$_1$–C$_6$)-alkenyloxy, and
(t') benzyloxy;
(4) cyano;
R$^4$ and R$^5$ are independently:
(1) hydrogen,
(2) C$_1$–C$_3$ alkyl, or
(3) phenyl,
R$^6$ is:
(1) hydrogen,
(2) oxo and a is a single bond,
(3) O(C=O)R$^{11}$, or
(4) absent when a is a double bond;
R$^7$, R$^8$ and R$^9$ are independently selected from the group consisting of:
(1) hydrogen,
(2) oxo,
(3) O(C=O)R$^{11}$; and
R$^{10}$, R$^{11}$ and R$^{12}$ are independently chosen from the group consisting of:
(1) H, and
(2) (C$_1$–C$_3$)-alkyl.

6. A compound selected from the group consisting of:
[5-S-5aα,5aα,7aα,8α,8β,11β,11aβ, 11bα,12α,13α,13aα]-13a-(1-R-acetoxyethyl)-8-hydroxy-8-(2-(2-ethoxyphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin;
[5-S-5aα,5aα,7aα,8α,8β,11β,11aβ,11bα,12α,13α,13aα]-13a-(1-R-acetoxyethyl)-8-hydroxy-8-(2-(2-n-butyloxyphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin;
[5-S-5aα,5aα,7aα,8α,8β,11β,11aβ,11bα,12α,13α,13aα]-13a-(1-R-acetoxyethyl)-8-hydroxy-8-(2-(2-n-allyloxyphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin;
[5-S-5aα,5aα,7aα,8α,8β,11β,11aβ,11bα,12α,13α,13aα]-13a-(1-R-acetoxyethyl)-8-hydroxy-8-(2-phenylethyl)-11,12,13-triacetoxy-5b,9,11a-trimethyl-1,3,5a,5b,6,7,7a,8,11,11a,11b,12,13,13a-tetradecahydrophenanthro[2,1-c]oxepin;
[5-S-5aα,5aα,7aα,8α,8β,11β,11aβ,11bα,12α,13α,13aα]-13a-(1-R-acetoxyethyl)-8-hydroxy-8-(but-3-en-1-yl)-11,12,13-triacetoxy-5b,9,11a-trimethyl-1,3,5a,5b,6,7,7a,8,11,11a,11b,12,13,13a-tetradecahydrophenanthro[2,1-c]oxepin;
[5-S-5aα,5aα,7aα,8α,8β,11β,11aβ,11bα,12α,13α,13aα]-13a-(1-R-acetoxyethyl)-8-hydroxy-8-(4,4-dimethylbut-3-en-1-yl)-11,12,13-triacetoxy-5b,9,11a-trimethyl-1,3,5a,5b,6,7,7a,8,11,11a,11b,12,13,13a-tetradecahydrophenanthro[2,1-c]oxepin;
[5-S-5aα,5aα,7aα,8α,8β,11β,11aβ,11bα,12α,13α,13aα]-13a-(1-R-acetoxyethyl)-8-hydroxy-8-(2-(2-methylphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin;
[5-S-5aα,5aα,7aα,8α,8β,11β,11aβ,11bα,12α,13α,13aα]-13a-(1-R-acetoxyethyl)-8-hydroxy-8-(2-(2-methoxyphenyl)ethyl)-11,12,13-triacetoxy-5b,9,11a-trimethyl-1,3,5a,5b,6,7,7a,8,11,11a,11b,12,13,13a-tetradecahydrophenanthro[2,1-c]oxepin;
[5-S-5aα,5aα,7aα,8α,8β,11β,11aβ,11bα,12α,13α,13aα]-13a-(1-R-acetoxyethyl)-8-hydroxy-8-(S-2-(phenyl)propyl)-11,12,13-triacetoxy- 5b,9,11a-trimethyl-1,3,5a,5b,6,7,7a,8,11,11a,11b,12,13,13a-tetradecahydrophenanthro[2,1-c]oxepin;
[5-S-5aa,5aa,7aa,8a,8b,11b,11ab,11ba,12a,13a,13aa]-13a-(1-R-acetoxyethyl)-8-hydroxy-8-(2-(phenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin;
[5-S-5aa,5aa,7aa,8a,8b,11b,11ab,11ba,12a,13a,13aa]-13a-(1-R-acetoxyethyl)-8-hydroxy-8-(R-2-phenylpropyl)-11,12,13-triacetoxy-5b,9,11a-trimethyl-1,3,5a,5b,6,7,7a,8,11,11a,11b,12,13,13a-tetradecahydrophenanthro[2,1-c]oxepin;
[5-S-5aα,5aα,7aα,8α,8β,11β,11aβ,11bα,12α,13α,13aα]-13a-(1-R-acetoxyethyl)-8-hydroxy-8-(2-(phenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin-3-one;
[5-S-5aa,5aa,7aa,8a,8b,11b,11ab,11ba,12a,13a,13aa]-13a-(1-R-acetoxyethyl)-8-hydroxy-8-(2-(2-methoxyphenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin;
[5-S-5aα,5aα,7aα,8α,8β,11β,11aβ,11bα,12α,13α,13aα]-13a-(1-R-acetoxyethyl)-8-hydroxy-8-(2-(2- ethylmercaptophenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin;

[5-S-5aα,5aα,7aα,8α,8β,11β,11aβ,11bα,12α,13α,13aα]-13a-(1-R-acetoxyethyl)-8-hydroxy-8-(2-(2-ethylphenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin;

[5-S-5aα,5aα,7aα,8α,8β,11β,11aβ,11bα,12α,13α,13aα]-13a-(1-R-acetoxyethyl)-8-hydroxy-8-(2-(2-methylmercaptophenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin;

[5-S-5aα,5aα,7aα,8α,8β,11β,11aβ,11bα,12α,13α,13aα]-13a-(1-R-acetoxyethyl)-8-hydroxy-8-(2-(2-ethylmercaptophenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin-3-one;

[5-S-5aα,5aα,7aα,8α,8β,11β,11aβ,11bα,12α,13α,13aα]-13a-(1-R-acetoxyethyl)-8-hydroxy-8-(2-(2-n-butylmercaptophenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin-3-one;

[5-S-5aα,5aα,7aα,8α,8β,11β,11aβ,11bα,12α,13α,13aα]-13a-(1-R-acetoxyethyl)-8-hydroxy-8-(2-(2-vinylphenyl)prop-2-enyl)-11,12,13-triacetoxy-5b,9,11a-trimethyl-1,3,5a,5b,6,7,7a,8,11,11a,11b,12,13,13a-tetradecahydrophenanthro[2,1-c]oxepin-3-one; and

[5-S-5aα,5aα,7aα,8α,8β,11β,11aβ,11bα,12α,13α,13aα]-13a-(1-R-acetoxyethyl)-8-hydroxy-8-(2-(S)-(−)-(2-ethylphenyl)propyl)-11,12,13-triacetoxy-5b,9,11a-trimethyl-1,3,5a,5b,6,7,7a,8,11,11a,11b,12,13,13a-tetradecahydrophenanthro[2,1-c]oxepin.

7. A method of treating a condition in a mammal, the treatment of which is effected or facilitated by $K_v1.3$ inhibition, comprising the administration, in an amount that is effective at inhibiting $K_v1.3$, of a compound of Formula I, as recited in claim 1.

8. A method of preventing or treating the resistance to transplantation or transplantation rejection of organs or tissues into a patient in need thereof, which comprises the administration of therapeutically effective amount of a compound of claim 1.

9. A method of suppressing the immune system in a subject in need thereof, which comprises the administration to the subject of an immune suppressing amount of a compound of Formula I, as recited in claim 1.

10. A pharmaceutical formulation comprising a pharmaceutically acceptable carrier and a therapeutically effective amount of the compound of Formula I, as recited in claim 1 or a pharmaceutically acceptable crystal form or hydrate thereof.

11. The pharmaceutical formulation of claim 10, comprising in addition, a second immunosuppressive agent comprising azathioprine, brequinar sodium, deoxyspergualin, mizaribine, mycophenolic acid morpholino ester, cyclosporin, FK-506 and rapamycin.

12. The method of claim 8, comprising the coadministration of a second immunosuppressive agent.

13. A method of treating a condition in a mammal, the treatment of which is effected or facilitated by $K_v1.3$ inhibition, comprising the administration of a pharmaceutical formulation comprising a pharmaceutical carrier and a compound of Formula I, as recited in claim 1, in an amount that is effective at inhibiting $K_v1.3$.

14. A method of treating a condition in a mammal, the treatment of which is effected or facilitated by $K_v1.3$ inhibition, comprising the coadministration of a therapeutically effective amount of a compound of Formula I, as recited in claim 1, with a second immunosuppressive agent.

* * * * *